(12) United States Patent
Sakon et al.

(10) Patent No.: US 12,403,179 B2
(45) Date of Patent: Sep. 2, 2025

(54) RELEASE OF GROWTH FACTORS AT WOUND HEALING STAGES

(71) Applicants: THE BOARD OF TRUSTEES OF THE UNIVERSITY OF ARKANSAS, Little Rock, AR (US); NATIONAL UNIVERSITY CORPORATION OKAYAMA UNIVERSITY, Okayama (JP)

(72) Inventors: Joshua Sakon, Fayetteville, AR (US); Robert Beitle, Fayetteville, AR (US); Hazim Aljewari, Fayetteville, AR (US); Osamu Matsushita, Okayama (JP); Stephanie Beitle, Fayetteville, AR (US)

(73) Assignees: THE BOARD OF TRUSTEES OF THE UNIVERSITY OF ARKANSAS, Little Rock, AR (US); NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 66 days.

(21) Appl. No.: 17/675,762

(22) Filed: Feb. 18, 2022

(65) Prior Publication Data
US 2022/0257715 A1 Aug. 18, 2022

Related U.S. Application Data

(60) Provisional application No. 63/151,023, filed on Feb. 18, 2021.

(51) Int. Cl.
| | | |
|---|---|---|
| *A61K 38/00* | (2006.01) | |
| *A61K 38/16* | (2006.01) | |
| *A61K 38/17* | (2006.01) | |
| *A61K 38/18* | (2006.01) | |
| *A61L 31/10* | (2006.01) | |
| *A61L 31/16* | (2006.01) | |

(52) U.S. Cl.
CPC ........ *A61K 38/1825* (2013.01); *A61K 38/164* (2013.01); *A61K 38/1709* (2013.01); *A61L 31/10* (2013.01); *A61L 31/16* (2013.01)

(58) Field of Classification Search
CPC ............ A61K 38/1709; A61K 38/1825; A61K 38/164; A61L 31/10; A61L 31/16; A61L 2300/25; A61P 1/00; C07K 14/475; C07K 14/50; C07K 14/575
See application file for complete search history.

(56) References Cited

U.S. PATENT DOCUMENTS

| | | | |
|---|---|---|---|
| 5,914,126 A | 6/1999 | Li et al. | |
| 6,077,692 A * | 6/2000 | Ruben | C07H 21/00 435/320.1 |
| 6,362,163 B1 | 3/2002 | Gardella et al. | |
| 7,167,059 B2 | 1/2007 | Abraham et al. | |
| 7,396,664 B2 | 7/2008 | Daly | |
| 7,465,537 B2 | 12/2008 | Raney et al. | |
| 8,030,448 B2 | 10/2011 | Koide et al. | |
| 8,450,273 B2 | 5/2013 | Sakon et al. | |
| 8,488,203 B2 | 7/2013 | Higashyyama et al. | |
| 8,617,543 B2 | 12/2013 | Huang et al. | |
| 9,062,300 B2 | 6/2015 | Gensure et al. | |
| 9,248,164 B2 | 2/2016 | Uchida et al. | |
| 9,354,240 B2 | 5/2016 | Yamagata et al. | |
| 9,526,765 B2 | 12/2016 | Ponnapakkam et al. | |
| 9,528,099 B2 | 12/2016 | Gensure et al. | |
| 9,579,273 B2 | 2/2017 | Ponnapakkam et al. | |
| 9,757,435 B2 | 9/2017 | Herber | |
| 10,046,040 B2 | 8/2018 | Galen | |
| 10,047,404 B2 | 8/2018 | Bergeron | |
| 10,111,983 B2 | 10/2018 | Shimp | |
| 10,202,434 B2 | 2/2019 | Gensure et al. | |
| 10,213,488 B2 | 2/2019 | Ponnapakkam et al. | |
| 10,358,471 B2 | 7/2019 | Gensure et al. | |
| 10,364,278 B2 | 7/2019 | Mohammadi et al. | |
| 10,385,113 B2 | 8/2019 | Thallapuranam et al. | |
| 10,442,842 B2 | 10/2019 | Beitle et al. | |
| 10,507,230 B2 | 12/2019 | Yamamoto | |
| 10,519,213 B2 | 12/2019 | Gensure et al. | |

(Continued)

FOREIGN PATENT DOCUMENTS

| | | |
|---|---|---|
| EP | 0207751 A1 | 1/1987 |
| JP | 2002-58485 | 2/2002 |

(Continued)

OTHER PUBLICATIONS

Vartak et al. Matrix metalloproteases: Underutilized targets for drug delivery. J Drug Target. Jan. 2007 ; 15(1): 1-20 (Year: 2007 ).*
Schmitt, C.P. et al., "Intermittent administration of parathyroid hormone (1-37) improves growth and bone mineral density in uremic rats," Kidney Int. (2000) 57(4):1484-92.
Schmitt, C.P. et al., "Structural organization and biological relevance of oscillatory parathyroid hormone secretion," Pediatr Nephrol. (2005) 20(3):346-51. Epub Feb. 8, 2005.

(Continued)

*Primary Examiner* — Lianko G Garyu
*Assistant Examiner* — Mercy H Sabila
(74) *Attorney, Agent, or Firm* — Quarles & Brady, LLP

(57) ABSTRACT

The present invention provides collagen-binding agents that can be used to treat wounds, ischemic heart disease, and other conditions. The collagen-binding agents comprise a therapeutic agent, a protease cleavage site, and a collagen-binding domain. The present invention further provides pharmaceutical compositions and biomedical devices comprising the disclosed collagen-binding agents, as well as methods for treating a condition using the collagen-binding agents.

6 Claims, 7 Drawing Sheets
Specification includes a Sequence Listing.

(56) References Cited

U.S. PATENT DOCUMENTS

| | | | |
|---|---|---|---|
| 10,519,236 | B2 | 12/2019 | Koide et al. |
| 11,001,820 | B2 | 5/2021 | Ponnapakkam et al. |
| 11,279,922 | B2 | 3/2022 | Ponnapakkam et al. |
| 11,624,060 | B2 * | 4/2023 | Sakon .................. C07K 14/635 424/85.1 |
| 2002/0102709 | A1 | 8/2002 | Ishikawa et al. |
| 2002/0164719 | A1 | 11/2002 | Hall et al. |
| 2003/0187232 | A1 | 10/2003 | Hubbell et al. |
| 2004/0053368 | A1 | 3/2004 | Ishikawa et al. |
| 2004/0220094 | A1 | 11/2004 | Skinner et al. |
| 2005/0119183 | A1 | 6/2005 | Wells et al. |
| 2005/0124537 | A1 | 6/2005 | Kostenuik et al. |
| 2005/0180986 | A1 | 8/2005 | Rich et al. |
| 2006/0014687 | A1 | 1/2006 | Crine et al. |
| 2006/0257376 | A1 | 11/2006 | Scadden et al. |
| 2006/0258569 | A1 | 11/2006 | McTavish |
| 2007/0224119 | A1 | 9/2007 | McTavish |
| 2008/0108562 | A1 | 5/2008 | Riviere et al. |
| 2009/0305352 | A1 | 12/2009 | Dai et al. |
| 2010/0129341 | A1 | 5/2010 | Sakon et al. |
| 2010/0159564 | A1 | 6/2010 | Dwulet et al. |
| 2013/0287759 | A1 | 10/2013 | Muñoz Montano |
| 2013/0337017 | A1 | 12/2013 | Gensure et al. |
| 2014/0335146 | A1 | 11/2014 | Uchida et al. |
| 2014/0377215 | A1 | 12/2014 | Ponnapakkam et al. |
| 2015/0038423 | A1 | 2/2015 | Ponnapakkam et al. |
| 2015/0284701 | A1 | 10/2015 | Gensure et al. |
| 2016/0339078 | A1 | 11/2016 | Hamill et al. |
| 2017/0101457 | A1 | 4/2017 | Gensure et al. |
| 2017/0106093 | A1 | 4/2017 | Ponnapakkam et al. |
| 2018/0055918 | A1 | 3/2018 | Herber |
| 2018/0140742 | A1 | 5/2018 | Uchida et al. |
| 2019/0284252 | A1 | 9/2019 | Thallapuranam et al. |
| 2019/0376053 | A1 * | 12/2019 | Sakon .................... C07K 14/50 |
| 2020/0023041 | A1 | 1/2020 | Holten-Andersen et al. |

FOREIGN PATENT DOCUMENTS

| | | | |
|---|---|---|---|
| JP | 2003/284553 | 10/2003 | |
| JP | 2004-500838 | 1/2004 | |
| WO | 2000/006195 | 2/2000 | |
| WO | 2000/049159 | 8/2000 | |
| WO | 2003/052091 | 6/2003 | |
| WO | 2004/071543 | 8/2004 | |
| WO | 2005/082941 | 9/2005 | |
| WO | 2006/072623 | 7/2006 | |
| WO | 2008/067199 | 5/2008 | |
| WO | 2008/124166 | 10/2008 | |
| WO | 2009/014854 | 1/2009 | |
| WO | 2010/087397 | 8/2010 | |
| WO | WO-2010091251 A2 * | 8/2010 | .......... C07K 14/195 |
| WO | 2011/142425 | 11/2011 | |
| WO | 2012/124338 | 9/2012 | |
| WO | 2012/157339 | 11/2012 | |
| WO | 2016/060252 | 4/2016 | |
| WO | 2016/142146 | 9/2016 | |
| WO | 2017/216620 | 12/2017 | |
| WO | 2019/113123 | 6/2019 | |
| WO | 2019/173829 | 12/2019 | |
| WO | WO-2020068261 A1 * | 4/2020 | ............. A61K 38/00 |

OTHER PUBLICATIONS

Schwartz, R.S., et al., Drug-eluting stents in preclinical studies: updated consensus recommendations for preclinical evaluation. Circ Cardiovasc Interv, 2008. 1(2): p. 143-53.

Seeman, E. et al., "Reconstructing the skeleton with intermittent parathyroid hormone," Trends Endocrinol Metab. (2001) 12(7):281-3.

Sekiguchi, H. et al., "Acceleration of bone formation during fracture healing by poly(pro-hyp-gly)10 and basic fibroblast growth factor containing polycystic kidney disease and collagen-binding domains from Clostridium histolyticum collagenase" J. Biomed Mater Res A. (2016) 104(6):1372-1378.

Sekiguchi, H., et al. "Basic fibroblast growth factor fused with tandem collagen-binding domains from Clostridium histolyticum collagenase ColG increases bone formation." BioMed research international 2018 (2018).

Sheikh, F., et al., Overexpression of FGF-2 increases cardiac myocyte viability after injury in isolated mouse hearts. Am J Physiol Heart Circ Physiol, 2001. 280(3): p. H1039-50.

Shen, V. et al., "Skeletal effects of parathyroid hormone infusion in ovariectomized rats with or without estrogen repletion," J Bone Miner Res. (2000) 15(4):740-6.

Shimizu, N. et al., "Novel parathyroid hormone (PTH) antagonists that bind to the juxtamembrane portion of the PTH/PTH-related protein receptor," J Biol Chem (2005) 280(3):1797-1807.

Shin, H., et al. Efficacy of Interventions for Prevention of Chemotherapy-Induced Alopecia: A systematic review and meta-analysis. International Journal of Cancer. 2015. 136: E442-E454.

Shinoda, Y. et al., "Mechanisms underlying catabolic and anabolic functions of parathyroid hormone on bone by combination of culture systems of mouse cells," J. of Cellular Biology (2010) 109(4):755-63.

Sides, C. R., et al.(2012). "Probing the 3-D Structure, Dynamics, and Stability of Bacterial Collagenase Collagen Binding Domain (apo- versus holo-) by Limited Proteolysis MALDI-TOF MS." Journal of the American Society for Mass Spectrometry 23(3): 505-519.

Silver, J. et al., "Harnessing the parathyroids to create stronger bones," Curr Opin Nephrol Hypertens. (2004) 13(4):471-6.

Silverberg, S.J.et al., "Skeletal disease in primary hyperparathyroidism," J Bone Miner Res., (1989) 4(3):283-91.

Skripitz, R. et al., "Parathyroid hormone—a drug for orthopedic surgery?," Acta Orthop Scand. (2004) 75(6):654-62.

Skripitz, R. et al., "Stimulation of implant fixation by parathyroid hormone (1-34)—A histomorphometric comparison of PMMA cement and stainless steel," J Orthop Res. (2005) 23(6):1266-70. Epub Jun. 16, 2005.

Smajilovic, S. et al., "Effect of intermittent versus continuous parathyroid hormone in the cardiovascular system of rats," Open Cardiovasc. Med. J. (2010) 4:110-6.

Spadaccio, C., et al., Drug releasing systems in cardiovascular tissue engineering. J Cell Mol Med, 2009. 13(3): p. 422-39.

Spiriti, J. et al (2010). "Mechanism of the calcium-induced trans-cis isomerization of a non-prolyl peptide bond in Clostridium histolyticum collagenase." Biochemistry 49(25): 5314-5320.

Stewart, A.F., "PTHrP(1-36) as a skeletal anabolic agent for the treatment of osteoporosis," Bone (1996) 19(4):303-306.

Stracke, S. et al., "Long-term outcome after total parathyroidectomy for the management of secondary hyperparathyroidism," Nephron Clin Pract. (2009) 111(2):c102-9. Epub Jan. 13, 2009.

Stratford, R., Jr., et al.(2014). "Pharmacokinetics in rats of a long-acting human parathyroid hormone-collagen binding domain peptide construct." J Pharm Sci 103(2): 768-775.

Strewler, G.J., "Local and systemic control of the osteoblast," J. of Clin. Invest. (2001) 107:271-272.

Suttamanatwong, S. et al., "Regulation of matrix Gla protein by parathyroid hormone in MC3T3-E1 osteoblast-like cells involves protein kinase A and extracellular signal-regulated kinase pathways," J Cell Biochem. (2007) 102(2):496-505.

Suttamanatwong, S. et al., "Sp proteins and Runx2 mediate regulation of matrix gla protein (MGP) expression by parathyroid hormone," J Cell Biochem. (2009) 107(2):284-92.

Suzuki, A. et al., "PTH/cAMP/PKA signaling facilitates canonical Wnt signaling via inactivation of glycogen synthase kinase-3beta in osteoblastic Saos-2 cells," J Cell Biochem. (2008) 104(1):304-17.

Swarthout, J.T. et al., "Parathyroid hormone-dependent signaling pathways regulating genes in bone cells," Gene (2002) 282(1-2):1-17.

Swarthout, J.T. et al., "Stimulation of extracellular signal-regulated kinases and proliferation in rat osteoblastic cells by parathyroid hormone is protein kinase C-dependent," J Biol Chem. (2001) 276(10):7586-92. Epub Dec. 6, 2000.

Takada, H. et al., "Response of parathyroid hormone to anaerobic exercise in adolescent female athletes," Acta Paediatr Jpn. (1998) 40(1):73-7.

(56) References Cited

OTHER PUBLICATIONS

Takasu, H. et al., "Dual signaling and ligand selectivity of the human PTH/PTHrP receptor," J Bone Miner Res. (1999) 14(1):11-20.
Talmage, R.V. et al., "Calcium homeostasis: reassessment of the actions of parathyroid hormone," Gen Comp Endocrinol. (2008) 156(1):1-8. Epub Nov. 12, 2007.
Tam, C.S. et al., "Parathyroid hormone stimulates the bone apposition rate independently of its resorptive action: differential effects of intermittent and continuous administration," Endocrinology (1982) 110(2):506-12.
Tawfeek, H. et al., "Disruption of PTH receptor 1 in T cells protects against PTH-induced bone loss," PLoS (2010) 5(8):e12290.
Ten Dijke, P. et al., "Characterization of type I receptors for transforming growth factor-β and Activin," Science (1994) 264:101-104.
Ten Dijke, P. et al., "Identification of type I receptors for osteogenic Protein-1 and bone morphogenetic Protein-4," J. of Biological Chem. (1994) 269(25):16985-16988.
Tokumoto, M. et al., "Parathyroid cell growth in patients with advanced secondary hyperparathyroidism: vitamin D receptor, calcium sensing receptor, and cell cycle regulating factors," Ther Apher Dial. (2005) 9(Suppl 1):S27-34.
Tollin, S.R. et al., "Serial changes in bone mineral density and bone turnover after correction of secondary hyperparathyroidism in a patient with pseudohypoparathyroidism type Ib," J Bone Miner Res. (2000) 15(7):1412-6.
Toyoshima, T. et al., "Collagen-binding domain of a Clostridium histolyticum collagenase exhibits a broad substrate spectrum both in vitro and in vivo," Connective Tissue Research (2001) 42(4):281-290.
Uchida K, et al: Acceleration of periosteal bone formation by human basic fibroblast growth factor containing a collagen-binding domain from Clostridium histolyticum collagenase. J Biomed Mater Res A 2014;102:1737-1743.
Uchida, K. et al. "Enhancement of periosteal bone formation by basic fibroblast-derived growth factor containing polycystic kidney disease and collagen-binding domains from Clostridium histolyticum collagenase" J. Tissue Eng Regen Med (2017) 11(4):1165-1172.
Ueno M, et al: Influence of internal fixator stiffness on murine fracture healing: two types of fracture healing lead to two distinct cellular events and FGF-2 expressions. Exp Anim 2011;60:79-87.
Ueno, M., et al (2014). "Acceleration of bone union after structural bone grafts with a collagen-binding basic fibroblast growth factor anchored-collagen sheet for critical-size bone defects." Biomed Mater 9(3): 035014.
United States Patent Office Action for U.S. Appl. No. 12/594,547 dated Aug. 6, 2012 (12 pages).
United States Patent Office Action for U.S. Appl. No. 14/365,226 dated Nov. 24, 2015 (8 pages).
United States Patent Office Action for U.S. Appl. No. 14/365,226 dated Jun. 10, 2016 (9 pages).
United States Patent Office Action for U.S. Appl. No. 14/378,067 dated Feb. 17, 2016 (16 pages).
United States Patent Office Action for U.S. Appl. No. 15/407,589 dated Jun. 26, 2018 (44 pages).
United States Patent Office Action for U.S. Appl. No. 15/407,589 dated Jun. 26, 2019 (7 pages).
Uzawa, T. et al., "Comparison of the effects of intermittent and continuous administration of human parathyroid hormone(1-34) on rat bone," Bone (1995) 16(4):477-84.
Vanstone, M.B. et al., "Rapid correction of bone mass after parathyroidectomy in an adolescent with primary hyperparathyroidism," J. Clin. Endocrinol. Metab. (2011) 96(2): E347-50. Epub Nov. 24, 2010.
Davis, J.E., A. Alghanmi, R. K. Gundampati, S.Jayanthi, E. Fields, M. Armstrong, V. Weidling, V. Shah, S. Agrawal, B. P.Koppolu, D. A. Zaharoff, and S. K. Thallapuranam (2018) Probing the role of proline-135 on the structure, stability, and cell proliferation activity of human acidic fibroblast growth factor. Arch. Biochem. Biophys., 654, 115-125.
Davis, J.E., R. K. Gundampati, S. Jayanthi, J. Anderson, A. Pickhardt, B.P. Koppolu, D.A. Zaharoff, and S. K. Thallapuranam (2018) Effect of extension of the heparin binding pocket on the structure, stability, and cell proliferation activity of the human acidic fibroblast growth factor. Biochem. Biophys. Rep., 13, 45-57. PMCID:#: 5857160.
Deal, C., "The use of intermittent human parathyroid hormone as a treatment for osteoporosis," Curr Rheumatol Rep. (2004) 6(1): 49-58.
Demiralp, B. et al., "Anabolic actions of parathyroid hormone during bone growth are dependent on c-fos," Endocrinology (2002) 143(10):4038-47.
Derner, R. et al., "The bone morphogenic protein," Clin. Podiatr. Med. Surg. (2005) 22(4):607-618.
Dobnig, H. et al., "The effects of programmed administration of human parathyroid hormone fragment (1-34) on bone histomorphometry and serum chemistry in rats," Endocrinology (1997) 138(11):4607-12.
Drake, M.T. et al., "Parathyroid hormone increases the expression of receptors for epidermal growth factor in UMR 106-01 cells," Endocrinology (1994) 134(4):1733-7.
Eckhard, U. et al.(2011). "Polycystic kidney disease-like domains of clostridial collagenases and their role in collagen recruitment." Biol Chem 392(11): 1039-1045.
Eckhard, U., et al.(2011). "Structure of collagenase G reveals a chew-and-digest mechanism of bacterial collagenolysis." Nat Struct Mol Biol 18(10): 1109-1114. Published online Sep. 25, 2011. Final edited version published Apr. 1, 2012.
Endo, K. et al., "1,25-dihydroxyvitamin D3 as well as its analogue OCT lower blood calcium through inhibition of bone resorption in hypercalcemic rats with continuous parathyroid hormone-related peptide infusion," J Bone Miner Res. (2000) 15(1):175-81.
Etoh, M. et al., "Repetition of continuous PTH treatments followed by periodic withdrawals exerts anabolic effects on rat bone," J Bone Miner Metab. (2010) 28(6):641-649.
Extended European Search Report for Application No. 08742686.2 dated Aug. 4, 2010 (8 pages).
Extended European Search Report for Application No. 12857691.5 dated Feb. 8, 2016 (16 pages).
Farhanigan, M.E., et al. Treatment of Alopecia Areata in the United States: A Retrospective Cross-Sectional Study. J Drugs Dermatology. 2015 14(9):1012-4.
Fitzpatrick, L.A. et al., "Acute primary hyperparathyroidism," Am J Med. (1987) 82(2):275-82.
Fleming, A. et al., "High-throughput in vivo screening for bone anabolic compounds with zebrafish," J Biomol Screen. (2005) 10(8):823-31. Epub Oct. 18, 2005.
Fouda, M.A., "Primary hyperparathyroidism: King Khalid University Hospital Experience," Ann Saudi Med. (1999) 19 (2):110-5.
Fox, J. et al., "Effects of daily treatment with parathyroid hormone 1-84 for 16 months on density, architecture and biomechanical properties of cortical bone in adult ovariectomized rhesus monkeys," Bone (2007) 41(3):321-330.
Fraher, L.J. et al., "Comparison of the biochemical responses to human parathyroid hormone-(1-31)NH2 and hPTH-(1-34) in healthy humans," J Clin Endocrinol Metab. (1999) 84(8):2739-43.
Franzen, P. et al., "Cloning of a TGFβ type I receptor that forms a heteromeric complex with the TGFβ type II receptor," Cell (1993) 75:681-692.
Frolik, C.A. et al., "Anabolic and catabolic bone effects of human parathyroid hormone (1-34) are predicted by duration of hormone exposure," Bone (2003) 33(3):372-379.
Fruchtl M, Sakon J, Beitle R. Expression of a collagen-binding domain fusion protein: effect of amino acid supplementation, inducer type, and culture conditions. Biotechnol Prog. Mar.-Apr. 2015;31(2):503-9. PubMed PMID: 25641757.
Fruchtl, M., J. Sakon and R. Beitle (2016). "Alternate carbohydrate and nontraditional inducer leads to increased productivity of a collagen binding domain fusion protein via fed-batch fermentation." Journal of Biotechnology 226: 65-73.

(56) References Cited

OTHER PUBLICATIONS

Fuentes, J. et al., "A PTH/PTHrP receptor antagonist blocks the hypercalcemic response to estradiol-17beta," Am. J. Physiol. Regul. Integr. Comp. Physiol. (2007) 293(2):R956-960.
Wong, V.W., et al., Surgical approaches to create murine models of human wound healing. J Biomed Biotechnol, 2011. 2011: p. 969618.
Fujimaki, H., et al (2016). "Oriented collagen tubes combined with basic fibroblast growth factor promote peripheral nerve regeneration in a 15 mm sciatic nerve defect rat model." J Biomed Mater Res A.
Fujita, T., "Parathyroid hormone in the treatment of osteoporosis," BioDrugs (2001) 15(11):721-728.
Fukayama, S. et al., "New insights into interactions between the human PTH/PTHrP receptor and agonist/antagonist binding," Am. J. Physiol. Endocrinol. Metab. (1998) 274:297-303.
Gao, Y. et al., "T cells potentiate PTH-induced cortical bone loss through CD40L signaling," Cell Metab. (2008) 8(2):132-45.
Gardella, T.J. et al., "Converting Parathyroid Hormone-related Peptide (PTHrP) into a Potent PTH-2 Receptor Agonist," J. of Biological Chemistry, (1996) 271(33):19888-19893.
Gaston, R. G., et al.(2015). "The Efficacy and Safety of Concurrent Collagenase Clostridium Histolyticum Injections for 2 Dupuytren Contractures in the Same Hand: A Prospective, Multicenter Study." J Hand Surg Am 40(10):1963-1971.
Gensure, R.C. et al., "Parathyroid hormone and parathyroid hormone-related peptide, and their receptors," Biochem Biophys Res Commun. (2005) 328(3):666-78.
Gensure, R.C. et al., "Parathyroid hormone without parathyroid glands," Endocrinology (2005) 146(2):544-546.
Gensure, R.C. et al., "Parathyroid hormone-related peptide and the hair cycle—is it the agonists or the antagonists that cause hair growth?" (2014) Experimental Dermatology, 23(12):865-867.
Gevers, E.F. et al., "Bone marrow adipocytes: a neglected target tissue for growth hormone," Endocrinology (2002) 143(10):4065-73.
Goltzman, D., "Studies on the mechanisms of the skeletal anabolic action of endogenous and exogenous parathyroid hormone," Arch Biochem Biophys. (2008) 473(2):218-24. Epub Mar. 10, 2008.
Gopalakrishnan, R. et al., "Role of matrix Gla protein in parathyroid hormone inhibition of osteoblast mineralization," Cells Tissues Organs (2005) 181(3-4):166-75.
Gosavi, A. et al., "An unusual presentation of parathyroid adenoma—a case report," Indian J Pathol Microbiol. (2005) 48(2):208-10.
Gu, W.X. et al., "Mutual up-regulation of thyroid hormone and parathyroid hormone receptors in rat osteoblastic osteosarcoma 17/2.8 cells," Endocrinology (2001) 142(1):157-64.
Guise, T.A., "Parathyroid hormone-related protein and bone metastases," Cancer (1997) 80(8 Supp):1572-1580.
Hall, A.K. et al., "The effects of parathyroid hormone on osteoblast-like cells from embryonic chick calvaria," Acta Endocrinol (Copenh). (1985) 108(2):217-23.
Han X, et al: Accelerated postero-lateral spinal fusion by collagen scaffolds modified with engineered collagen-binding human bone morphogenetic protein-2 in rats. PLoS One 2014;9:e98480.
Han, B. et al., "Collagen-targeted BMP3 fusion proteins arrayed on collagen matrices or porous ceramics impregnated with Type I collagen enhance osteogenesis in a rat cranial defect model," J Orthopaedic Research (2002) 20:747-755.
Han, B. et al., "Refolding of a recombinant collagen-targeted TGF-beta2 fusion protein expressed in *Escherichia coli*," Protein Expr. Purif. (1997) 11(2):169-178.
Hashimoto, et al., Sequential treatment with intermittent low-dose human parathyroid hormone (1-34) and bisphosphonate enhances large-size skeletal reconstruction by vascularized bone transplantation. Calcif. Tissue Int. (2007) 232-239.
Hausenloy, D.J. and D.M. Yellon, New directions for protecting the heart against ischaemia-reperfusion injury: targeting the Reperfusion Injury Salvage Kinase (RISK)-pathway. Cardiovasc Res, 2004. 61(3): p. 448-60.

Hausenloy, D.J. and D.M. Yellon, Reperfusion injury salvage kinase signalling: taking a RISK for cardioprotection. Heart Fail Rev, 2007. 12(3-4): p. 217-34.
Headley, C.M., "Hungry bone syndrome following parathyroidectomy," Anna J., (1998) 25(3):283-9; quiz 290-1.
Heath, H., 3rd, "Clinical spectrum of primary hyperparathyroidism: evolution with changes in medical practice and technology," J Bone Miner Res. (1991) 6(Suppl 2):S63-70; discussion S83-4.
Henderson, M.A. et al., "Parathyroid hormone-related protein localization in breast cancers predict improved prognosis," Cancer Res. (2006) 66(4):2250-2256.
Orloff, J.J. et al., Parathyroid hormone-related protein as a prohormone: posttranslational processing and receptor interactions. Endocrine Rev (1994) 15:40-60.
Owens, R.J. et al., "Mapping the collagen-binding site of human fibronectin by expression in *Escherichia coli*," The EMBO Journal (1986) 5(11)2825-2830.
Padua, R.R., et al., FGF-2-induced negative inotropism and cardioprotection are inhibited by chelerythrine: involvement of sarcolemmal calcium-independent protein kinase C. J Mol Cell Cardiol, 1998. 30(12): p. 2695-709.
Paillard, M. et al., "Determinants of parathormone secretion in primary hyperparathyroidism," Horm Res. (1989) 32(1-3):89-92.
Palmen, M., et al., Fibroblast growth factor-1 improves cardiac functional recovery and enhances cell survival after ischemia and reperfusion: a fibroblast growth factor receptor, protein kinase C, and tyrosine kinase dependent mechanism. J Am Coll Cardiol, 2004. 44(5): p. 1113-23.
Parfitt, A.M. et al., "Hypercalcemia due to constitutive activity of the parathyroid hormone (PTH)/PTH-related peptide receptor: comparison with primary hyperparathyroidism," J Clin Endocrinol Metab. (1996) 81(10):3584-8.
Parfitt, A.M., "The actions of parathyroid hormone on bone: relation to bone remodeling and turnover, calcium homeostasis, and metabolic bone disease. Part IV of IV parts: The state of the bones in uremic hyperaparathyroidism—the mechanisms of skeletal resistance to PTH in renal failure and pseudohypoparathyroidism and the role of PTH in osteoporosis, osteopetrosis, and osteofluorosis," Metabolism. (1976) 25(10):1157-88.
Partial Supplementary European Search Report dated Oct. 1, 2015 (7 pages).
Perbellini, F., et al., Investigation of cardiac fibroblasts using myocardial slices. Cardiovasc Res, 2018. 114(1): p. 77-89.
Peters, E.M.J. et al., "A new strategy for modulating chemotherapy-induced alopecia, using PTH/PTHrP receptor agonist and antagonist," J Invest Dermatol (2001) 117(2):173-178.
Pettway, et al., "Anabolic actions of PTH (1-34): Use of a novel tissue engineering model to investigate temporal effects on bone," Bone (2005) 36(6):959-970.
Phatharajaree, W., A. Phrommintikul, and N. Chattipakorn, Matrix metalloproteinases and myocardial infarction. Can J Cardiol, 2007. 23(9): p. 727-33.
Phelps, E. et al., "Parathyroid hormone induces receptor activity modifying protein-3 (RAMP3) expression primarily via 3',5'-cyclic adenosine monophosphate signaling in osteoblasts," Calcif Tissue Int. (2005) 77(2):96-103. Epub Aug. 11, 2005.
Philominathan et al., "Bacterial collagen-binding domain targets undertwisted regions of collagen," Protein Sci. (2012) 21(10):1554-65.
Philominathan et al., "Unidirectional binding of Clostridial Colleagenase to Triple Helical Substrates," Journal of Biological Chemistry (2009) 284(16):10868-10876.
Philominathan, S. T., et al.(2009). "Ca2+-induced linker transformation leads to a compact and rigid collagen-binding domain of Clostridium histolyticum collagenase." FEBS J 276(13): 3589-3601.
Pirih, F.Q. et al., "Parathyroid hormone induces the NR4A family of nuclear orphan receptors in vivo," Biochem Biophys Res Commun. (2005) 332(2):494-503.
Podbesek, R. et al., "Effects of two treatment regimes with synthetic human parathyroid hormone fragment on bone formation and the tissue balance of trabecular bone in greyhounds," Endocrinology (1983) 112(3):1000-6.

(56) References Cited

OTHER PUBLICATIONS

Ponnapakkam T, Katikaneni R, Sakon J, Stratford R, Gensure RC. Treating osteoporosis by targeting parathyroid hormone to bone. Drug Discov Today. Mar. 2014; 19(3):204-8. PubMed PMID: 23932952; PubMed Central PMCID: PMC3979969.
Ponnapakkam, T. et al., "A fusion protein of parathyroid hormone (PTH) and a collagen binding domain shows superior efficacy and longer duration of action compared to PTH(1-34) as an anabolic bone agent in normal female mice," Bone (2009) 44:S35-S36.
Ponnapakkam, T. et al., "A Single Injection of the Anabolic Bone Agent, Parathyroid Hormone-Collagen Binding Domain (PTH-CBD), Results in Sustained Increases in Bone Mineral Density for up to 12 Months in Normal Female Mice" Calcified Tissue (2012) 91(30:196-203.
Ponnapakkam, T., et al.(2011). "Prevention of chemotherapy-induced osteoporosis by cyclophosphamide with a long-acting form of parathyroid hormone." J Endocrinol Invest 34(11): e392-397.
Ponnapakkam, T., et al., "Monthly administration of a novel PTH-collagen binding domain fusion protein is anabolic in mice," Calcif Tissue Int.2011;88:511-520.
Poole, K.E. et al., "Parathyroid hormone—a bone anabolic and catabolic agent," Curr Opin Pharmacol. (2005) 5(6):612-7. Epub Sep. 21, 2005.
Potter, L.K. et al., "Response to continuous and pulsatile PTH dosing: a mathematical model for parathyroid hormone receptor kinetics," Bone (2005) 37(2):159-169.
Potts, J.T., "Parathyroid hormone: past and present," J Endocronology (2005) 187:311-325.
Qin, L. et al., "Parathyroid hormone: a double-edged sword for bone metabolism," Trends Endocrinol Metab. (2004) 15(2):60-5.
Ragab, D., D.M. Abdallah, and H.S. El-Abhar, Cilostazol renoprotective effect: modulation of PPAR-gamma, NGAL, KIM-1 and IL-18 underlies its novel effect in a model of ischemia-reperfusion. PLoS One, 2014. 9(5): p. e95313.
Rattanakul, C. et al., "Modeling of bone formation and resorption mediated by parathyroid hormone: response to estrogen/PTH therapy" Biosystems (2003) 70(1):55-72.
Reboucas, J.S., N.S. Santos-Magalhaes, and F.R. Formiga, Cardiac Regeneration using Growth Factors: Advances and Challenges. Arq Bras Cardiol, 2016. 107(3): p. 271-275.
Restriction Requirement for U.S. Appl. No. 14/365,226 dated Jun. 22, 2015 (8 pages).
Restriction Requirement for U.S. Appl. No. 14/378,067 dated Oct. 23, 2015 (9 pages).
Restriction requirement for U.S. Appl. No. 14/743,629 dated Apr. 20, 2016 (8 pages).
Restriction requirement for U.S. Appl. No. 15/407,589 dated Jan. 8, 2018 (5 pages).
Richardson, M.L. et al., "Bone mineral changes in primary hyperparathyroidism," Skeletal Radiol. (1986) 15(2):85-95.
Rickard, D.J. et al., "Intermittent treatment with parathyroid hormone (PTH) as well as a non-peptide small molecule agonist of the PTH1 receptor inhibits adipocyte differentiation in human bone marrow stromal cells," Bone (2006) 39(6):1361-1372. Epub Aug. 10, 2006.
Rixon, R.H. et al., "Parathyroid hormone fragments may stimulate bone growth in ovariectomized rats by activating adenylyl cyclase," J Bone Miner Res. (1994) 9(8):1179-89.
Robinson, J.A. et al., "Identification of a PTH regulated gene selectively induced in vivo during PTH-mediated bone formation," J Cell Biochem. (2006) 98(5):1203-20.
Rosen, C.J., "The cellular and clinical parameters of anabolic therapy for osteoporosis," Crit Rev Eukaryot Gene Expr. (2003) 13(1):25-38.
Rubin, M. et al., "The anabolic effects of parathyroid hormone therapy," Osteoporosis International (2002) 13(4):267-277.
Rubin, M.R. et al., "The anabolic effects of parathyroid hormone therapy," Clin Geriatr Med. (2003) 19(2):415-32.
Rubin, M.R. et al., "The potential of parathyroid hormone as a therapy for osteoporosis," Int J Fertil Womens Med. (2002) 47(3):103-15.
Safer, J.D. et al., "A topical parathyroid hormone/parathyroid hormone-related peptide receptor antagonist stimulates hair growth in mice," Endocrinology (2007)148:1167-1170.
Saito W, et al: Acceleration of bone formation during fracture healing by injectable collagen powder and human basic fibroblast growth factor containing a collagen-binding domain from Clostridium histolyticum collagenase. J Biomed Mater Res A 2014;102:3049-3055.
Saito W, et al: Acceleration of callus formation during fracture healing using basic fibroblast growth factor-kidney disease domain-collagen-binding domain fusion protein combined with allogenic demineralized bone powder. J Orthop Surg Res 2015;10:59.
Sakon, Joshua (2020) 12P Presentation, Preventing Heart Failure with Site-specific Growth Factor.
Schaefer, F., "Pulsatile parathyroid hormone secretion in health and disease," Novartis Found Symp. (2000) 227:225-39; discussion 239-43.
Schilli, M.B. et al., "Control of hair growth with parathyroid hormone (7-34)," J Invest Dermatol (1997) 108:928-932.
Schluter, K.-D. et al., "A N-terminal PTHrP peptide fragment void of a PTH/PTHrP-receptor binding domain activates cardiac ETA receptors," British Journal of Pharmacology (2001) 132:427-432.
Schluter, K.-D. et al., "Stem cell mobilization versus stem cell homing: potential role for parathyroid hormone?" Cardiovasc Res. (2008) 77(4):612-613.
Abdelhadi, M. et al., "Bone mineral recovery after parathyroidectomy in patients with primary and renal hyperparathyroidism," J Clin Endocrinol Metab. (1998) 83(11):3845-51.
Abe, Y. et al., "Enhancement of graft bone healing by intermittent administration of human parathyroid hormone (1-34) in a rat spinal arthrodesis model," Bone (2007) 41(5):775-785.
Abraham, M. et al., "Enhanced unique pattern of hematopoietic cell mobilization induced by the CXCR4 antagonist 4F-Benzoyl-TN14003," Stem Cells (2007) 25:2158-2166.
Abshirini, H. et al., "Pathologic fractures: a neglected clinical feature of parathyroid adenoma," Case (2010) p. 357029. Epub Nov. 29, 2010.
Akimoto, M. et al., "Effects of CB-VEGF-A injection in rat flap models for improved survival," (2013) Plast. Reconstr. Surg. 131(4):717-725.
Aleksyniene, R. et al., "Parathyroid hormone—possible future drug for orthopedic surgery," Medicina (Kaunas) (2004) 40(9):842-9.
Andrade, M.C., et al., "Bone mineral density and bone histomorphometry in children on long-term dialysis," Pediatr Nephrol. (2007) 22(10):1767-72. Epub Aug. 7, 2007.
Andrades, J.A. et al., "A recombinant human TGF-beta1 fusion protein with collagen-binding domain promotes migration, growth, and differentiation of bone marrow mesenchymal cells," Exp. Cell Res. (1999) 250(2):485-498.
Arunkumar, A. I., S. K. Thallapuranam, K. M. Kathir, S. Srisailam, H. M. Wang, P. S. T. Leena, Y. H. Chi, C. H. Wu, R. T. Wu, I. M. Chiu and C. Yu. Oligomerization of acidic fibroblast growth factor is not a prerequisite for its cell proliferation activity (2002) Protein Science, 11, 1050-1061.
Balachandran K, Alford PW, Wylie-Sears J, Goss JA, Grosberg A, Aikawa E, Bischoff J, Levine RA, Parker KK. Cyclic Strain Induces Dual-Mode Endothelial-Mesenchymal Transformation of the Cardiac Valve. Proceedings of the National Academy of Sciences. 2011;108(50):19943-8.
Balachandran K, Bakay M, Connolly JM, Zhang, X, Yoganathan AP, Levy RJ. Aortic Valve Cyclic Stretch Causes Increased Remodeling Activity and Enhanced Serotonin Receptor Responsiveness. Annals of Thoracic Surgery. Jul. 2011;92(1):147-53.
Ballen, K., "Targeting the stem cell niche: squeezing blood from bones," (2007) Bone Marrow Transplantation 39:655-660.
Ballen, K.K. et al., "Phase I trial of parathyroid hormone to facilitate stem cell mobilization," Biology of Blood and Marrow Transplantation (2007) 13:838-843.
Barros, S.P., et al., "Parathyroid hormone protects against periodontitis-associated bone loss," J Dent Res. (2003) 82(10):791-5.

(56) References Cited

OTHER PUBLICATIONS

Bauer, et al.: Structures of three polycystic kidney disease-like domains from Clostridium histolyticum collagenases ColG and ColH. Acta Crystallogr D Biol Crystallogr 2015;71:565-577.

Bedi, B., et al., "Inhibition of antigen presentation and T cell costimulation blocks PTH-induced bone loss," Ann N Y Acad Sci. (2010) 1192:215-21.

Belinsky, G.S. et al., "Direct measurement of hormone-induced acidification in intact bone," J Bone Miner Res., (2000) 15(3):550-6.

Bellido, T., et al., "Chronic elevation of parathyroid hormone in mice reduces expression of sclerostin by osteocytes: a novel mechanism for hormonal control of osteoblastogenesis," Endocrinology (2005) 146(11):4577-83. Epub Aug. 4, 2005.

Bergenstock, M.K. et al., "Parathyroid hormone stimulation of noncanonical Wnt signaling in bone," Ann N Y Acad Sci. (2007) 1116:354-9.

Bergwitz, C. et al., "Rapid desensitization of parathyroid hormone dependent adenylate cyclase in perifused human osteosarcoma cells (SaOS-2)," Biochem Biophys Acta. (1994) 1222(3):447-56.

Bianchi, E.N. et al., "Beta-arrestin2 regulates parathyroid hormone effects on a p38 MAPK and NFkappaB gene expression network in osteoblasts" Bone (2009) 45(4):716-25. Epub Jun. 26, 2009.

Bilezikian, J.P. et al., "Asymptomatic primary hyperparathyroidism: new issues and new questions—bridging the past with the future," J Bone Miner Res. (2002) 17(Suppl 2):N57-67.

Bilezikian, J.P. et al., "Characterization and evaluation of asymptomatic primary hyperparathyroidism," J Bone Miner Res. (1991) 6(Suppl 2):S85-9; discussion S121-4.

Blachowicz, A. et al., "Serum 1-84 and 7-84 parathyroid hormone concentrations and bone in patients with primary hyperparathyroidism," Langenbecks Arch Surg. (2008) 393(5):709-13. Epub Jul. 11, 2008.

Blair, H. et al., "Recent advances in osteoclast biology and pathological bone resorption," Histology and Histopathology (2004) 19(1):189-199.

Broadus, A.E. et al., Humoral hypercalcemia of cancer. Identification of a novel parathyroid hormone-like peptide. N Engl J Med (1988) 319:556-563.

Buargub, M.A. et al., "Prevalence and pattern of renal osteodystrophy in chronic hemodialysis patients: a cross sectional study of 103 patients," Saudi J Kidney Dis Transpl. (2006) 17(3):401-7.

Calvi, L.M. et al., "Activated parathyroid hormone/parathyroid hormone-related protein receptor in osteoblastic cells differentially affects cortical and trabecular bone," J. Clin. Invest. (2001)107:277-286.

Calvi, L.M. et al., "Osteoblastic cells regulate the haematopoietic stem cell niche," Nature (2003) 425:841-846.

Canalis, E. et al., "Insulin-like growth factor I mediates selective anabolic effects of parathyroid hormone in bone cultures," J Clin Invest. (1989) 83(1):60-5.

Canalis, E., "Effect of hormones and growth factors on alkaline phosphatase activity and collagen synthesis in cultured rat calvariae," Metabolism (1983) 32(1): 14-20.

Carter, P.H. et al., "Discovery of a small molecule antagonist of the parathyroid hormone receptor by using an N-terminal parathyroid hormone peptide probe," Proc Natl Acad Sci U.S.A. (2007) 104(16):6846-6851.

Carter, P.H. et al., "Selective and Nonselective Inverse Agonists for Constitutively Active Type-1 Parathyroid Hormone Receptors: Evidence for Altered Receptor Conformations," Endocrinology (2001) 142(4):1534-1545.

Caviness P, Bauer R, Tanaka K, Janowska K, Roeser JR, Harter D, Sanders J, Ruth C, Matsushita O, Sakon J. $Ca^{2+}$-induced orientation of tandem collagen binding domains from clostridial collagenase ColG permits two opposing functions of collagen fibril formation and retardation. FEBS J. Sep. 2018;285(17):3254-3269. PubMed PMID: 30035850; PubMed Central PMCID: PMC6126967.

Chan, H.W. et al., "Prospective study on dialysis patients after total parathyroidectomy without autoimplant," Nephrology (2009) 15(4):441-7.

Chen, B. et al., "Homogeneous osteogenesis and bone regeneration by demineralized bone matrix loading with collagen-targeting bone morphogenetic protein-2," Biomaterials (2007) 28:1027-1035.

Chen, D. et al., "Bone morphogenetic proteins," Growth Factors (2004) 22(4):233-241.

Chen, Q. et al., "Effects of an excess and a deficiency of endogenous parathyroid hormone on volumetric bone mineral density and bone geometry determined by peripheral quantitative computed tomography in female subjects," J Clin Endocrinol Metab. (2003) 88(10):4655-8.

Cherian, P.P. et al., "Role of gap junction, hemichannels, and connexin 43 in mineralizing in response to intermittent and continuous application of parathyroid hormone," Cell Commun Adhes. (2008) 15(1):43-54.

Chevalley, T. et al., "Bone and hormones. Effects of parathyroid hormone on the bone," Presse Med. (1999) 28(10):547-53.

Choi, U.S., K.W. Leong, and H.S. Yoo, In vivo wound healing of diabetic ulcers using electrospun nanofibers immobilized with human epidermal growth factor (EGF). Biomaterials, 2008. 29(5): p. 587-96.

Cleutjens, J.P., et al., Collagen remodeling after myocardial infarction in the rat heart. Am J Pathol, 1995. 147(2): p. 325-38.

Cohen, A. et al., "Osteoporosis in adult survivors of adolescent cardiac transplantation may be related to hyperparathyroidism, mild renal insufficiency, and increased bone turnover," J Heart Lung Transplant. (2005) 24(6):696-702.

Compston, J.E., "Skeletal actions of intermittent parathyroid hormone: effects on bone remodelling and structure," Bone (2007) 40(6):1447-1452.

Cormier, C., "Parathyroid hormone in osteoporosis," Presse Med. (2006) 35(3 Pt 2):495-501.

Corsi, A. et al., "Osteomalacic and hyperparathyroid changes in fibrous dysplasia of bone: core biopsy studies and clinical correlations," J Bone Miner Res. (2003) 18(7):1235-46.

Cosman, F., "Anabolic therapy for osteoporosis: parathyroid hormone," Current Osteoporosis Reports (2005) 3(4):143-149.

Cosman, F., "Parathyroid hormone treatment for osteoporosis," Current Opinion in Endocrinology, Diabetes & Obesity (2008) 15:495-501.

Cundy, T. et al., "Hyperparathyroid bone disease in chronic renal failure," Ulster Med J. (1985) 54(Suppl):S34-43.

Datta, N.S. et al., "Distinct roles for mitogen-activated protein kinase phosphatase-1 (MKP-1) and ERK-MAPK in PTH1R signaling during osteoblast proliferation and differentiation," Cell (2010) 22(3):457-66. Epub.

Hoare, S.R. et al., "Specificity and stability of a new PTH1 receptor antagonist, mouse TIP(7-39)," Peptides (2002) 23(5):989-998.

Hock, J.M. et al., "Effects of continuous and intermittent administration and inhibition of resorption on the anabolic response of bone to parathyroid hormone," J Bone Miner Res. (1992) 7(1):65-72.

Hock, J.M. et al., "Human parathyroid hormone-(1-34) increases bone mass in ovariectomized and orchidectomized rats," Endocrinology (1988) 122(6):2899-2904.

Holick, M.F. et al., "Topical PTH (1-34) is a novel, safe and effective treatment for psoriasis: a randomized self-controlled trial and an open trial," (2003) British J. Dermatology 149:370-376.

Homme, M. et al., "Differential regulation of RGS-2 by constant and oscillating PTH concentrations," Calcif Tissue Int. (2009) 84(4):305-12. Epub Feb. 20, 2009.

Horwitz, M.J. et al., "Continuous PTH and PTHrP infusion causes suppression of bone formation and discordant effects on 1,25(OH)2 vitamin D," J Bone Miner Res. (2005) 20(10):1792-803. Epub Jun. 6, 2005.

Horwitz, M.J. et al., "Parathyroid hormone-related protein for the treatment of postmenopausal osteoporosis: defining the maximal tolerable dose," J Clin Endocrinol Metab. (2010) 95(3):1279-87.

Hruska, K.A. et al., "Regulation of skeletal remodeling by parathyroid hormone," Contrib Nephrol. (1991) 91:38-42.

(56) References Cited

OTHER PUBLICATIONS

Huang, Z., et al., Uncoupling the Mitogenic and Metabolic Functions of FGF1 by Tuning FGF1-FGF Receptor Dimer Stability. Cell Rep, 2017. 20(7): p. 1717-1728.
Hui, Q., et al., FGF Family: From Drug Development to Clinical Application. Int J Mol Sci, 2018. 19(7).
Hunter, G.K. et al., "Induction of collagen mineralization by a bone sialoprotein-decorin chimeric protein," J. Biomed. Mater. Res. (2001) 55(4):496-502.
Ichikawa, S., et al., High dietary phosphate intake induces development of ectopic calcifications in a murine model of familial tumoral calcinosis. J Bone Miner Res, 2014. 29(9): p. 2017-23.
Iida-Klein, A. et al., "Short-term continuous infusion of human parathyroid hormone 1-34 fragment is catabolic with decreased trabecular connectivity density accompanied by hypercalcemia in C57BL/J6 mice," J Endocrinol. (2005) 186(3):549-57.
International Search Report and Written Opinion of the International Searching Authority for Application No. PCT/US08/004589 dated Oct. 28, 2008 (17 pages).
International Search Report and Written Opinion of the International Searching Authority for Application No. PCT/ US12/69831 dated Mar. 14, 2013 (12 pages).
International Search Report and Written Opinion of the International Searching Authority for Application No. PCT/ US2013/25541 dated Jun. 17, 2013 (16 pages).
International Search Report and Written Opinion of the International Searching Authority for Application No. PCT/ US2018/ 017665 dated May 7, 2018 (11 pages).
Ishii, H. et al., "Daily intermittent decreases in serum levels of parathyroid hormone have an anabolic-like action on the bones of uremic rats with low-turnover bone and osteomalacia," Bone (2000) 26(2):175-82.
Ishikawa, T. et al., "Delivery of a growth factor fusion protein having collagen-binding activity to wound tissues," Artif. Organs (2003) 27(2):147-154.
Ishikawa, T. et al., "Establishment of a functionally active collagen-binding vascular endothelial growth factor fusion protein in situ," Arterioscler. Thromb. Vasc. Biol. (Sep. 2006):1-7.
Ishikawa, T. et al., "Production of a biologically active epidermal growth factor fusion protein with high collagen affinity," J. Biochem. (2001) 129(4)627-633.
Ishizuya, T. et al., "Parathyroid hormone exerts disparate effects on osteoblast differentiation depending on exposure time in rat osteoblastic cells," J Clin Invest. (1997) 99(12):2961-70.
Ito, M., "Parathyroid and bone: Effect of parathyroid hormone on bone quality," Clin Calcium. (2007) 17(12):1858-64.
Ito, M., "Parathyroid hormone and bone quality," Clin Calcium. (2005) 15(12):31-7.
Jeon, E. et al., "Engineering and application of collagen-binding fibroblast growth factor 2 for sustained release," (2013) J. of Biomed. Materials Research: Part A.
Jilka, R.L. et al., "Continuous elevation of PTH increases the number of osteoblasts via both osteoclast-dependent and -independent mechanisms," J Bone Miner Res. (2010) 25(11):2427-37.
Jilka, R.L., "Molecular and cellular mechanisms of the anabolic effect of intermittent PTH," Bone (2007) 40(6):1434-1446. Epub Apr. 6, 2007.
Jonsson, K.B. et al., "Tuberoinfundibular peptide 39 binds to the parathyroid hormone (PTH)/PTH-related peptide receptor, but functions as an antagonist," Endocrinology (2001) 142(2):704-709.
Kaji, H., "Parathyroid and bone: Effects of parathyroid hormone on bone resorption and formation: differences between intermittent and continuous treatment," Clin Calcium., (2007) 17(12):1836-42.
Katikaneni et al., "Therapy for alopecia areata in mice using parathyroid hormone agonists and antagonists, linked to a collagen-binding domain," J. of Investigative Dermatology Symposium Proceedings, (2013) 16(1):S61-S62.
Katikaneni et al., "Treatment for chemotherapy-induced alopecia in mice using parathyroid hormone agonists and antagonists linked to coolagen binding domain," Int. J. Cancer (2012) 131(5):E813-821.
Katikaneni R., et al. Parathyroid hormone linked to a collagen binding domain (PTH-CBD) promotes hair growth in a mouse model of chemotherapy-induced alopecia in a dose-dependent manner. Anticancer Drugs. 2014. 25(7):819-825.
Katikaneni, R. et al. Therapy for alopecia Areata in Mice by Stimulating the Hair Cycle with Parathyroid Hormone Agonists Linked to a Collagen-Binding Domain. The Journal of Investigative Dermatology Symposium. 2015. 17: 13-15.
Katikaneni, R. et al. Treatment and Prevention of Chemotherapy-induced alopecia with PTH-CBD, a collagen targeted parathyroid hormone analog, in a non-depilated mouse model. Anticancer Drugs. 2014. 25(1): 30-38.
Kato T, et al: Single local injection of recombinant fibroblast growth factor-2 stimulates healing of segmental bone defects in rabbits. J Orthop Res 1998;16:654-659.
Kawaguchi H, et al: A local application of recombinant human fibroblast growth factor 2 for tibial shaft fractures: A randomized, placebo-controlled trial. J Bone Miner Res 2010;25:2735-2743.
Kawaguchi H, et al: Local application of recombinant human fibroblast growth factor-2 on bone repair: a dose-escalation prospective trial on patients with osteotomy. J Orthop Res 2007;25:480-487.
Kawaguchi H, et al: Stimulation of fracture repair by recombinant human basic fibroblast growth factor in normal and streptozotocin-diabetic rats. Endocrinology 1994;135:774-781.
Kaye, M. et al., "Elective total parathyroidectomy without autotransplant in end-stage renal disease," Kidney Int. (1989) 35(6):1390-9.
Kerr, R., S. Agrawal, S. Maity, B. Koppulu, S. Jayanthi, G. S. Kumar, R. K. Gundampati, D. S. McNabb, D. A. Zaharoff, and S. K. Thallapuranam (2019) Design of thrombin resistant acidic human fibroblast growth factor (hFGF1) that exhibits enhanced cell proliferation activity. Biochem. Biophys. Res. Commun., 518, 191-196. PMID-31420170.
Khan, A. et al., "Primary hyperparathyroidism: pathophysiology and impact on bone," Cmaj. (2000) 163(2):184-7.
Kido, S. et al., "Mechanism of PTH actions on bone," Clin Calcium. (2003) 13(1):14-8.
Kistler, H., "Primary hyperparathyroidism: An analysis of 152 patients with special references to acute life threatening complications (acute hyperparathyroidism)," Schweiz Med Wochenschr. (1976) 106(Suppl 3):1-61.
Kitazawa, R. et al., "Effects of continuous infusion of parathyroid hormone and parathyroid hormone-related peptide on rat bone in vivo: comparative study by histomorphometry," Bone Miner. (1991) 12(3):157-66.
Klempa, I., "Treatment of secondary and tertiary hyperparathyroidism—surgical viewpoints," Chirurg. (1999) 70(10):1089-101.
Koh, A.J. et al., "3',5'-Cyclic adenosine monophosphate activation in osteoblastic cells: effects on parathyroid hormone-1 receptors and osteoblastic differentiation in vitro," Endocrinology (1999) 140(7):3154-62.
Komarova, S.V., "Mathematical model of paracrine interactions between osteoclasts and osteoblasts predicts anabolic action of parathyroid hormone on bone," Endocrinology. (2005) 146(8):3589-95. Epub Apr. 28, 2005.
Kousteni, S. et al., "The cell biology of parathyroid hormone in osteoblasts," Curr Osteoporos. Rep. (2008) 6(2):72-6.
Kroll, M.H., "Parathyroid hormone temporal effects on bone formation and resorption," Bull Math Biol. (2000) 62(1):163-88.
Kubler, N.R. et al., "Inductive properties of recombinant human BMP-2 produced in a bacterial expression system," Int. J. Oral Maxillofac. Surg. (1998) 27:305-309.
Wan, Q. et al., "Intra-articular injection of parathyroid hormone in the temporomandibular joint as a novel therapy for mandibular asymmetry," Med Hypotheses (2009) 74(4):685-7.
Wang, C.A. et al., "Natural history of parathyroid carcinoma. Diagnosis, treatment, and results," Am J Surg. (1985) 149(4):522-7.
Wang, E. et al., "Recombinant human bone morphogenetic protein induces bone formation," Proc. Natl. Acad. Sci. USA (1990) 87:2220-2224.
Wang, Y. et al., "A theoretical model for simulating effect of parathyroid hormone on bone metabolism at cellular level," Mol Cell Biomech. (2009) 6(2):101-12.

(56) References Cited

OTHER PUBLICATIONS

Wang, Y. et al., "Gender differences in the response of CD-1 mouse bone to parathyroid hormone: potential role of IGF-I," J Endocrinol. (2006) 189(2):279-87.
Watanabe-Nakayama, T., et al (2016). "High-speed atomic force microscopy reveals strongly polarized movement of clostridial collagenase along collagen fibrils." Sci Rep 6: 28975.
Watson, P.H. et al., "Enhanced osteoblast development after continuous infusion of hPTH(1-84) in the rat," Bone (1999) 24(2):89-94.
Weber, M., et al., Blood-Contacting Biomaterials: In Vitro Evaluation of the Hemocompatibility. Front Bioeng Biotechnol, 2018. 6: p. 99.
Weir, E.C. et al., "Synthetic parathyroid hormone-like protein (1-74) is anabolic for bone in vivo," Calcif Tissue Int. (1992) 51(1):30-4.
Wesche, J., J. Malecki, A. Wiedlocha, C. S. Skjerpen, P. Claus and S. Olsnes (2006). "FGF-1 and FGF-2 require the cytosolic chaperone Hsp90 for translocation into the cytosol and the cell nucleus." J Biol Chem 281(16): 11405-11412.
Whitfield, J.F., "Taming Psoriatic Keratinocytes-PTHs' uses go up another notch," J. Cell. Biochem. (2004) 93:251-256.
Wilson, J.J. et al., "A bacterial collagen-binding domain with novel calcium-binding motif controls domain orientation," EMBO Journal (2003) 22(8)1743-1752.
Wuthrich, R.P. et al., "The role of calcimimetrics in the treatment of hyperparathyroidism," Eur. J. Clin. Invest. (2007) 37(12):915-922.
Xu, M. et al., "Basal bone phenotype and increased anabolic responses to intermittent parathyroid hormone in healthy male COX-2 knockout mice," Bone (2010) 47(2):341-52. Epub May 13, 2010.
Yang, C. et al., "Effects of continuous and pulsatile PTH treatments on rat bone marrow stromal cells," Biochem Biophys Res Commun. (2009) 380(4):791-6. Epub Feb. 3, 2009.
Yoshihara, K. et al., "Cloning and nucleotide sequence analysis of the colH gene from Clostridium histolyticum encoding a collagenase and a gelatinase," J Bacteriol (1994) 176:6489-6496.
Younes, N.A. et al., "Laboratory screening for hyperparathyroidism," Clin Chim Acta. (2005) 353(1-2):1-12.
Zakrzewska, M., D. Krowarsch, A. Wiedlocha, S. Olsnes and J. Otlewski (2006). "Structural requirements of FGF-1 for receptor binding and translocation into cells." Biochemistry 45(51): 15338-15348.
Zang, X.Y. et al., "Effects of parathyroid hormone and estradiol on proliferation and function of human osteoblasts from fetal long bone: An in vitro study," Chin Med J (Engl). (1994) 107(8):600-3.
Zaruba, M.M. et al., "Parathyroid hormone treatment after myocardial infarction promotes cardiac repair by enhanced neovascularization and cell survival," Cardiovasc Res (2008) 77(4):722-731.
Zhou, H. et al., "Anabolic action of parathyroid hormone on cortical and cancellous bone differs between axial and appendicular skeletal sites in mice," Bone (2003) 32(5):513-520.
Swencki-Underwood, B. et al., "Expression and characterization of a human BMP-7 variant with improved biochemical properties," Protein Expr. Purif. (2008) 57(2): 312-319.
An, B., et al.(2015). "Collagen interactions: Drug design and delivery." Adv Drug Deliv Rev. Feb. 1, 2016:97:69-84. Epub Nov. 26, 2015.
Duijvelshoff, R., et al., Host Response and Neo-Tissue Development during Resorption of a Fast Degrading Supramolecular Electrospun Arterial Scaffold. Bioengineering (Basel), 2018. 5(3).
Dunn, L., et al., Murine model of wound healing. J Vis Exp, 2013(75): p. e50265.
Fields, G. B. (2013). "Interstitial collagen catabolism" J Biol Chem 288(13): 8785-8793.
Galiano, R.D., et al., Quantitative and reproducible murine model of excisional wound healing. Wound Repair Regen, 2004. 12(4): p. 485-92.
Gao, F., A.D. Kight, Ad, R. Henderson, S. Jayanthi, P. Patel, M. Murchison, R. L. Goforth, S. K. Thallapuranam, R. L. Henry, and C. D. Heyes (2015). Regulation of Structural Dynamics within a Signal Recognition Particle Promotes Binding of Protein Targeting Substrates. J. Biol. Chem., 290, 15462-15474.
Gho, J., et al., Heart failure following STEMI: a contemporary cohort study of incidence and prognostic factors. Open Heart, 2017. 4(2): p. e000551.
Irwin D, Shin DH, Zhang S, Barr BK, Sakon J, Karplus PA, Wilson DB. Roles of the catalytic domain and two cellulose binding domains of Thermomonospora fusca E4 in cellulose hydrolysis. J Bacteriol. Apr. 1998;180(7):1709-14. PubMed PMID: 9537366; PubMed Central PMCID: PMC107081.
Jansen, P.L. et al., "Hernia disease and collagen gene regulation: are there clues for intervention?" Hernia (2006) 10:486-491.
Khan SN, et al.: Bone growth factors. Orthop Clin North Am 2000;31:375-388.
Kuwaba, K., et al.(2001). "Elongated dermatan sulphate in post-inflammatory healing skin distributes among collagen fibrils separated by enlarged interfibrillar gaps." Biochem J 358(Pt 1): 157-163.
Lam NT, Lam H, Sturdivant NM, Balachandran K. Fabrication of a matrigel-collagen semi-interpenetrating scaffold for use in dynamic valve interstitial cell culture. Biomedical Materials. 2017. 12(4):045013.
Lam NT, Muldoon TJ, Quinn KP, Rajaram N, Balachandran K. Valve interstitial cell contractile strength and metabolic state are dependent on its shape. Integrative Biology (Cambridge). 2016;8(10):1079-1089).
"Liang, C.C., A.Y. Park, and J.L. Guan, In vitro scratch assay: a convenient andinexpensive method for analysis of cell migration in vitro. Nat Protoc, 2007. 2(2): p. 329-33.".
Lu JZ, Fujiwara T, Komatsuzawa H, Sugai M, Sakon J. Cell wall-targeting domain of glycylglycine endopeptidase distinguishes among peptidoglycan cross-bridges. J Biol Chem. Jan. 6, 2006;281(1):549-58. PubMed PMID: 16257954.
Malyszko, J. et al., "Markers of bone metabolism in hemodialyses and hemodiafiltration," Ren. Fail. (2007) 29(5):595-601.
Miyachi, Y. et al., "Long-term safety and efficacy of high-concentration (20 mug/g) tacalcitol ointment in psoriasis vulgaris," Eur J Dermatol (2002) 12(5):463-468.
Perez J, Diaz N, Tandon I, Plate R, Martindale C, Balachandran K. Elevated serotonin interacts with angiotensin-II to result in altered valve interstitial cell contractility and remodeling. Cardiovascular Engineering and Technology. 2018;9(2):168-180.
Proesmans, W. & Van Dyck, M. "Enalapril in children with Alport syndrome" Pediatr Nephrol (2004) 19:271-275.
Ruppert, R. et al., "Human bone morphogenetic protein 2 contains a heparin-binding site which modifies its biological activity," Eur. J. Biochem. (1996) 237:295-302.
Schneider, A. et al., "Skeletal homeostasis in tissue-engineered bone," J Orthop Res. (2003) 21(5):859-64.
Spurney, R.F. et al., "Anabolic effects of a G protein-coupled receptor kinase inhibitor expressed in osteoblasts," J Clin Invest. (2002) 109(10):1361-71.
Lam NT, Tandon I, Balachandran K. The role of fibroblast growth factor 1 and 2 on the pathological behavior of valve interstitial cells in a three-dimensional mechanically-conditioned model. Journal of Biological Engineering. 2019;13(1), 45.
Lane, J.M., "Bone morphogenic protein science and studies," J. Orthop. Trauma (2005) 19(10 Supp.):S17-22.
Lemaire, V. et al., "Modeling the interactions between osteoblast and osteoclast activities in bone remodeling," J Theor Biol. (2004) 229(3):293-309.
Li, X. et al., "Determination of dual effects of parathyroid hormone on skeletal gene expression in vivo by microarray and network analysis," J Biol Chem. (2007) 282(45):33086-97. Epub Aug. 9, 2007.
Li, X. et al., "In vivo parathyroid hormone treatments and RNA isolation and analysis," Methods Mol Biol. (2008) 455:79-87.
Liu, J. et al., "Intermittent PTH administration: a novel therapy method for periodontitis-associated alveolar bone loss," Med Hypotheses. (2009) 72(3):294-6. Epub Nov. 30, 2008.
Locklin, R.M. et al., "Mediators of the biphasic responses of bone to intermittent and continuously administered parathyroid hormone," J Cell Biochem. (2003) 89(1):180-90.
Locus BAA06251 (GI 710023), Collagenase precursor from Clostridium histolyticum, Jan. 30, 2003. This amino acid sequence is disclosed

(56) References Cited

OTHER PUBLICATIONS in this application as Seq ID No. 6. The sequence of residues 901-1021 of BAA06251 corresponds to the collagen binding domain included in the fusion protein of Seq ID No. 1.
Locus EAW68494 (GI 119588900), Parathyroid hormone isoform from *Homo sapiens*, Dec. 18, 2006. Residues 64-147 of EAW68494 correspond to the PTH of Seq ID No. 7.
Lotinun, S. et al., "Differential effects of intermittent and continuous administration of parathyroid hormone on bone histomorphometry and gene expression," Endocrine. (2002) 17(1):29-36.
Lotinun, S. et al., "Triazolopyrimidine (trapidil), a platelet-derived growth factor antagonist, inhibits parathyroid bone disease in an animal model for chronic hyperparathyroidism," Endocrinology. (2003) 144(5):2000-7.
Lumachi, F. et al., "Lumbar spine bone mineral density changes in patients with primary hyperparathyroidism according to age and gender," Ann N Y Acad Sci. (2007) 1117:362-6. Epub Jul. 26, 2007.
Ma, Y.L. et al., "Catabolic effects of continuous human PTH (1--38) in vivo is associated with sustained stimulation of RANKL and inhibition of osteoprotegerin and gene-associated bone formation," Endocrinology (2001) 142(9):4047-54.
Machado Do Reis, L. et al., "Accentuated osteoclastic response to parathyroid hormone undermines bone mass acquisition in osteonectin-null mice," Bone (2008) 43(2):264-73. Epub Apr. 13, 2008.
Malluche, H.H. et al., "Effects of long-term infusion of physiologic doses of 1-34 PTH on bone" Am J Physiol. (1982) 242(2):F197-201.
Malluche, H.H. et al., "Endogenous calcitonin does not protect against hyperparathyroid bone disease in renal failure," Miner. Electrolyte Metab. (1986) 12(2):113-8.
Malluche, H.H. et al., "Influence of the parathyroid glands on bone metabolism," Eur J Clin Invest. (2006) 36(Suppl 2):23-33.
Malluche, H.H. et al., "Osteomalacia and hyperparathyroid bone disease in patients with nephrotic syndrome," J Clin Invest. (1979) 63(3):494-500.
Marcinkowska, E., K. Superat and A. Wiedlocha (2006). "FGF-1 as a possible carrier for targeted drug delivery." Oncol Res 16(1): 27-34.
Masi, L. et al., "Molecular, biochemical and cellular biology of PTH anabolic action," J Endocrinol Invest. (2005) 28(8 Suppl):37-40.
Mathias, R. et al., "Renal bone disease in pediatric and young adult patients on hemodialysis in a children's hospital," J Am Soc Nephrol. (1993) 3(12):1938-46.
Matsushita, O. et al., "A study of the collagen-binding domain of a 116-kDa Clostridium histolyticum collagenase," J Biological Chem (1998) 273(6):3643-3648.
Matsushita, O. et al., "Gene duplication and multiplicity of C. Histolyticum collagenases," J. Bacteriol. (1999) 181:923-933.
Matsushita, O. et al., "Substrate recognition by the collagen-binding domain of Clostridium histolyticum class I collagenase," J of Biological Chem (2001) 276(12):8761-8770.
Mccauley, L.K. et al., "Parathyroid hormone stimulates fra-2 expression in osteoblastic cells in vitro and in vivo," Endocrinology (2001) 142(5):1975-81.
McCauley, L.K. et al., "Proto-oncogene c-fos is transcriptionally regulated by parathyroid hormone (PTH) and PTH-related protein in a cyclic adenosine monophosphate-dependent manner in osteoblastic cells," Endocrinology (1997) 138(12):5427-33.
McCauley, L.K et al., "PTH/PTHrP receptor is temporally regulated during osteoblast differentiation and is associated with collagen synthesis," J Cell Biochem (1996) 61:638-647.
McDonald, I.M. et al., "Discovery and characterization of novel, potent, non-peptide parathyroid hormone-1 receptor antagonists," J. Med. Chem. (2007) 50(20):4789-4792.

Minisola, S. et al., "Trabecular bone mineral density in primary hyperparathyroidism: relationship to clinical presentation and biomarkers of skeletal turnover," Bone Miner. (1993) 20(2):113-23.
Minisola, S. et al., "Uneven deficits in vertebral bone density in postmenopausal patients with primary hyperparathyroidism as evaluated by posterior-anterior and lateral dual-energy absorptiometry," Osteoporos Int. (2002) 13(8):618-23.
Mitlak, B.H. et al., "Asymptomatic primary hyperparathyroidism," J Bone Miner Res. (1991) 6(Suppl 2):S103-10; discussion S121-4.
Morley, P. et al., "Anabolic effects of parathyroid hormone on bone," Trends Endocrinol. Metab. (1997) 8(6):225-31.
Morley, P. et al., "Parathyroid hormone: an anabolic treatment for osteoporosis," Curr Pharm Des. (2001) 7(8):671-87.
Murray, E.J. et al., "E64d, a membrane-permeable cysteine protease inhibitor, attenuates the effects of parathyroid hormone on osteoblasts in vitro," Metabolism (1997) 46(9):1090-4.
Nagase, H., Substrate Specificity of MMPs, in Matrix Metalloproteinase Inhibitors in Cancer Therapy, N.J. Clendeninn and K. Appelt, Editors. 2001, Springer-Science-Business Media, LLC. p. 39-66.
Nasu, M. et al., "Stimulatory effects of parathyroid hormone and 1,25-dihydroxyvitamin D3 on insulin-like growth factor-binding protein-5 mRNA expression in osteoblastic UMR-106 cells: the difference between transient and continuous treatments," FEBS Lett. (1997) 409(1):63-6.
Neer, R.M. et al., "Effect of parathyroid hormone (1-34) on fractures and bone mineral density in postmenopausal women with osteoporosis," N. Engl. J. Med. (2001) 344(19):1434-1441.
Nemeth, E.F., "Pharmacological regulation of parathyroid hormone secretion," Curr Pharm. Des. (2002) 8(23):2077-87.
Nilsson, P., "Bone disease in renal failure. Clinical and histomorphometric studies," Scand J Urol Nephrol Suppl. (1984) 84:1-68.
Nishi, N. et al., "A novel drug delivery system with a collagn-binding domain derived from Clostridium histolyticum collagnase" Connective Tissue (1998) 30(1):37-42.
Nishi, N. et al., "Collagen-binding growth factors: Production and characterization of functional fusion proteins having a collagen-binding domain," PNAS (1998) 95(12):7018-7023.
Nishida, N. et al."Collagen-binding mode of Vwf-a3 domain determined by a transferred cross-saturation experiment" (Natl. Struct. Biol. (2003) 10(1):53-58.
Nomura, R. et al., "Contribution of the Collagen-Binding Proteins of Streptococcus mutans to Bacterial Colonization of Inflamed Dental Pulp" PLoS One (2016) 11(7):e0159613.
O'Brien, C.A. et al., "IL-6 is not required for parathyroid hormone stimulation of RANKL expression, osteoclast formation, and bone loss in mice," Am J Physiol Endocrinol Metab. (2005) 289(5):E784-93. Epub Jun. 14, 2005.
Office Action for U.S. Appl. No. 15/407,589 dated Mar. 19, 2020.
Office Action for U.S. Appl. No. 16/485,290 dated Jun. 24, 2021.
Ohbayashi, N., et al.(2013). "Solution structure of clostridial collagenase h and its calcium-dependent global conformation change." Biophys J 104(7): 1538-1545.
Okazaki, R., "Parathyroid hormone—its mechanisms of action and issues on clinical application," Clin Calcium. (2005) 15(5):845-51.
Olgaard, K. et al., "Can hyperparathyroid bone disease be arrested or reversed?," Clin J Am Soc Nephrol. (2006) 1(3):367-73. Epub Mar. 29, 2006.
Onyia, J.E. et al., "Molecular profile of catabolic versus anabolic treatment regimens of parathyroid hormone (PTH) in rat bone: an analysis by DNA microarray," J Cell Biochem. (2005) 95(2):403-18.

\* cited by examiner

RELEASE OF GROWTH FACTORS AT WOUND HEALING STAGES

CROSS-REFERENCE TO RELATED APPLICATIONS

This application claims priority to U.S. Provisional Application No. 63/151,023 filed on Feb. 18, 2021, the contents of which are incorporated by reference in their entireties.

STATEMENT REGARDING FEDERALLY SPONSORED RESEARCH

This invention was made with government support under grant numbers GM130174 and GM103429 awarded by the National Institutes of Health. The government has certain rights in this invention.

SEQUENCE LISTING

A Sequence Listing accompanies this application and is submitted as an ASCII text file of the sequence listing named "169879_00150_ST25.txt" which is 80,841 bytes in size and was created on Feb. 4, 2022. The sequence listing is electronically submitted via EFS-Web with the application and is incorporated herein by reference in its entirety.

BACKGROUND

Rapid diagnosis and percutaneous coronary intervention after a coronary blockage improve patient survival. Nonetheless, one in four patients develop heart failure within four years of a first heart attack. The American Heart Association reports that 635,000 Americans have a new myocardial infarction each year with 275,000 deaths attributable to heart failure (2009 data). Healthcare costs and productivity losses due to cardiovascular disease cost the U.S. $273-$320 billion annually according to the American Heart Association. Assurant Employee Benefits, an insurance provider, reported that the lifetime cost of treating less severe heart attacks is $760,000 per person, which represents a substantial burden on heart patients and their families. For a severe heart attack, the cost can reach $1 million.

One in four first-time heart attack victims will experience some measure of heart failure within four years of the initial episode. Currently, there are no therapeutics available that can promote regeneration of the heart. While available treatments reduce the symptoms of myocardial ischemia-induced injury and delay the onset of heart failure, they are unable to reverse cardiac damage. Accordingly, there remains a need in the art for improved therapeutics that promote regeneration of heart tissue.

SUMMARY

In a first aspect, the present invention provides collagen-binding agents comprising a therapeutic agent, a protease cleavage site, and a collagen-binding domain. The collagen-binding domain is a polypeptide selected from the group consisting of SEQ ID NOs:6-53, a polypeptide having at least 90% sequence identity to SEQ ID NOs:6-53, and a fragment of at least 8 consecutive amino acids of SEQ ID NOs:6-53. In some embodiments, the therapeutic agent is a fibroblast growth factor (FGF) polypeptide. In some embodiments, the protease cleavage site is the cleavage site of a matrix metalloproteinase (MMP).

In a second aspect, the present invention provides pharmaceutical compositions comprising the collagen-binding agents disclosed herein and a pharmaceutically acceptable carrier.

In a third aspect, the present invention provides biomedical devices comprising a coating that comprises a collagen-binding agent disclosed herein.

In a fourth aspect, the present invention provides methods of treating a condition. In a first embodiment, the methods comprise administering a collagen-binding agent or a pharmaceutical composition disclosed herein to a subject in an amount effective to treat the condition. In a second embodiment, the methods comprise administering a biomedical device disclosed herein to a subject in need of treatment with the therapeutic agent.

DETAILED DESCRIPTION

Figure 1:
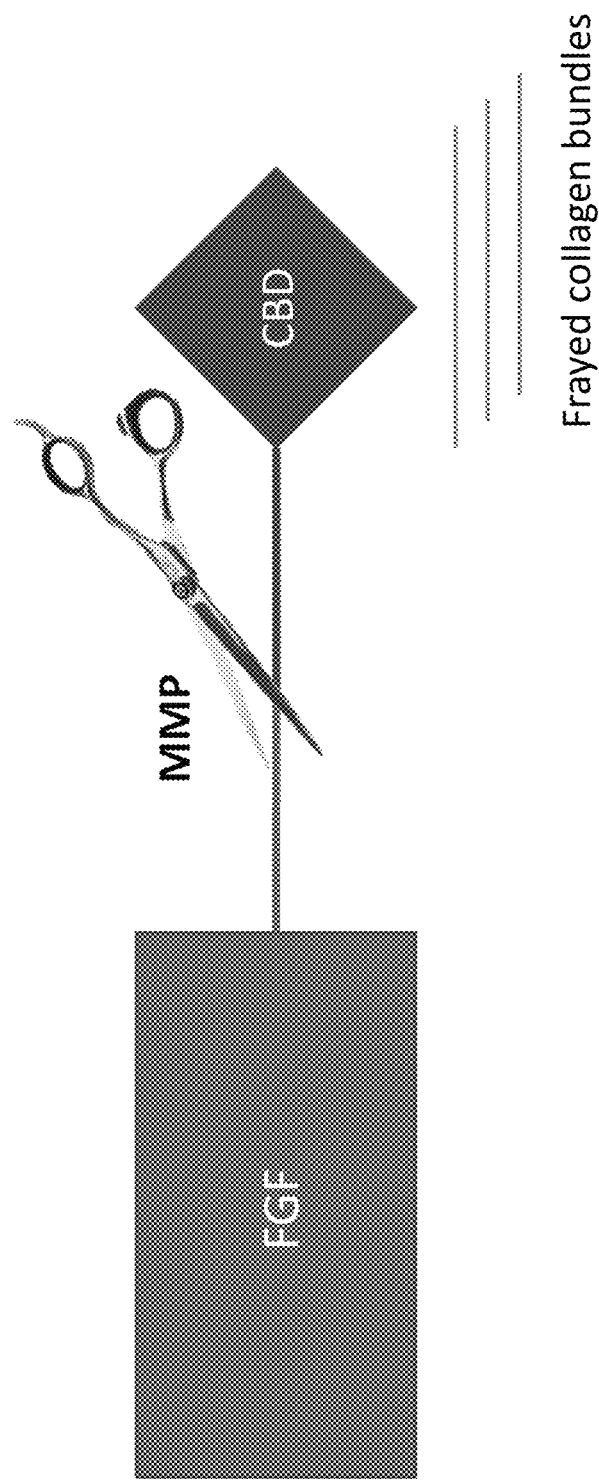
FIG. 1 is a schematic of the collagen-binding fusion protein disclosed herein. The fusion protein comprises a fibroblast growth factor (FGF) protein fused to a collagen-binding domain (CBD) via a linker peptide that comprises a matrix metalloproteinases (MMP) cleavage site.
Figure 2:
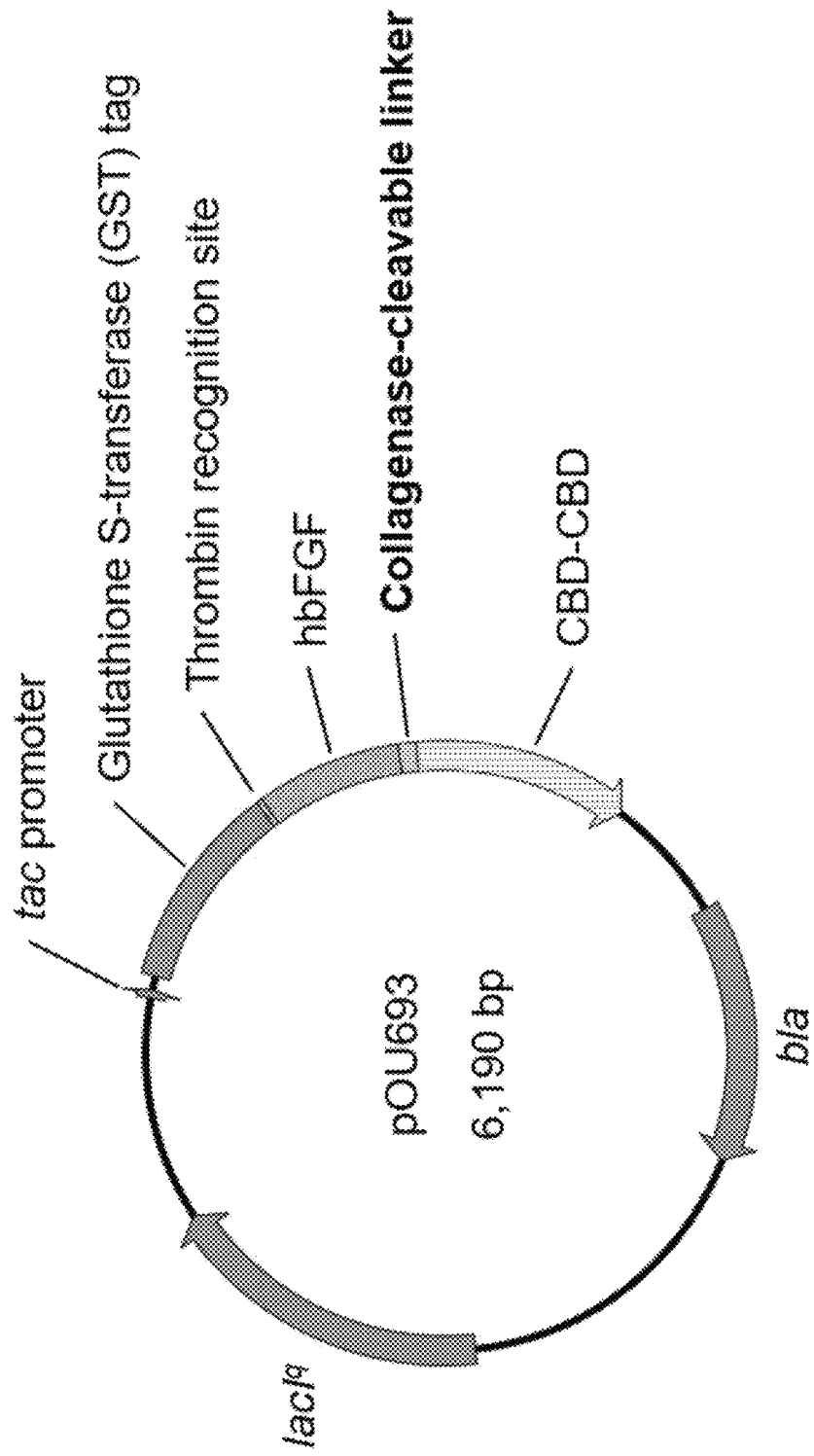
FIG. 2 is a vector map of the pCHG112-bFGF (pOU693) plasmid described in Example 3. This plasmid encodes a fusion protein in which human basic FGF (hbFGF) and a tandem CBD (CBD-CBD) are separated by a collagenase-cleavable linker such that these portions of the fusion protein can be cleaved apart by a collagenase. On the N-terminus, the fusion protein comprises (1) a glutathione S-transferase (GST) tag for affinity purification with glutathione-Sepharose beads, and (2) a thrombin recognition site that allows the GST tag to be removed via thrombin cleavage following affinity purification. Fusion protein expression is driven by the tac promoter. Inclusion of a lacI$^q$ repressor makes this expression inducible via addition of isopropyl-β-D-thiogalactopyranoside (IPTG). Finally, the plasmid includes a bla gene, which encodes β-lactamase, making transformants resistant to ampicillin.

The present invention provides collagen-binding agents that can be used to treat wounds, ischemic heart disease, and other conditions. The collagen-binding agents comprise a therapeutic agent, a protease cleavage site, and a collagen-binding domain. The present invention further provides pharmaceutical compositions and biomedical devices comprising the disclosed collagen-binding agents, as well as methods for treating a condition using the collagen-binding agents.

Growth factors enhance regeneration. As a result, growth factor-based treatments that promote regeneration of heart tissue following a heart attack have long been desired. However, the challenges associated with targeted delivery of growth factors and off-target effects of the growth factors have severely limited their clinical use. To overcome these challenges, the collagen-binding agents of the present invention have been designed to be both spatially and temporally regulated. Inclusion of a collagen-binding domain causes the collagen-binding agents to be lesion-seeking, targeting them to exposed collagen fibrils. Further, the collagen-binding agents are designed such that upregulation of a protease that cleaves the protease cleavage site temporally controls the release of the therapeutic agent from the collagen-binding domain.

In some embodiments, the collagen-binding agents are fusion proteins. For instance, in Example 1, the inventors describe the generation of a fusion protein that comprises a non-mitogenic fibroblast growth factor (FGF) protein as a therapeutic agent. This protein was selected because it is known to accelerate fibroblast cell migration and is hypothesized to have cardioprotective effects and to promote cardiac regeneration. The inventors' fusion protein comprises an FGF protein linked to a collagen-binding domain via a linker peptide that comprises an MMP cleavage site. The MMP cleavage site allows FGF to be released from the fusion protein when the cognate MMP is upregulated during the inflammatory phase of the wound healing process. While FGF is known to be effective for the treatment of acute wounds, its clinical use has been severely limited by its ability to promote tumorigenesis. Thus, controlling the delivery of FGF, both spatially and temporally, will allow it to aid in a critical phase of wound healing, while reducing its off-target effects and improving its clinical safety.

The inventors envision that their collagen-binding fusion proteins could be used to promote heart regeneration following myocardial ischemia-induced injury. Specifically, they imagine that their fusion protein could be delivered within the proximity of the heart via inclusion in the coating of a stent. Because stent placement is part of the standard treatment regimen, administration of the fusion protein in this manner would not significantly change the typical clinical workflow. Initially, to avoid excess fibrin formation, the fusion protein is not released from the stent and remains inactive, reducing the risk for in-stent restenosis. Once the fusion protein is released from the stent, the collagen-binding domain will target it to sites of exposed collagen fibers that accumulate during post-myocardial infarction remodeling. MMP upregulation during adverse ventricular remodeling would then release FGF from the fusion protein, allowing it to aid in the remodeling of the fibrin clot into new extracellular matrix (ECM). Importantly, release of FGF would occur during the stage of wound healing at which FGF will be most beneficial to patients. Thus, this collagen-binding agent represents a promising means to promote heart tissue remodeling and prevent a heart failure.

Collagen-Binding Agents:

In a first aspect, the present invention provides therapeutic collagen-binding agents. The collagen-binding agents comprise a therapeutic agent, a protease cleavage site, and a collagen-binding domain. Specifically, the collagen-binding domain is a polypeptide selected from the group consisting of SEQ ID NOs:6-53, a polypeptide having at least 90% sequence identity to SEQ ID NOs:6-53, and a fragment of at least 8 consecutive amino acids of SEQ ID NOs:6-53 capable of binding collagen.

Collagen-Binding Domain

The "collagen-binding domain (CBD)" is a polypeptide that binds to collagen. The ability of a polypeptide to bind to collagen can be assessed as described in U.S. Patent Publication No. 2010/0129341 or International Publication No. WO2008/124166, which are incorporated herein by reference in their entirety. Briefly, the polypeptide is incubated with collagen in a buffer, and the mixture is passed through a filter that allows for the passage of the polypeptide but blocks the passage of collagen, such that passage of the polypeptide is blocked by the filter only if it binds to collagen. The filtrate is then assayed for the presence of the polypeptide. Suitably, at least 80%, 85%, 90%, 95%, 98%, or 99% of the collagen-binding domain is retained by the filter in this assay as compared to when the filtration is performed in the absence of collagen.

The collagen-binding domains disclosed herein are segments of collagenase proteins found in bacteria. In some embodiments, the collagen-binding domain is derived from ColG, a class I collagenase from *Clostridium histolyticum* (J. Bacteriol. 181:923-933, 1999), or from ColH, a class II collagenase from *Clostridium histolyticum* (J. Bacteriol. 176: 6489-6496, 1994). Compositions comprising a collagen-binding domain from ColH are described in US Patent Publication No. 2010/0129341; International Publication No. WO2008/124166; International Publication No. WO2018/148573, each of which is hereby incorporated herein by reference in its entirety. In previous work, the inventors demonstrated that the C-terminal collagen-binding domain of the *Clostridium histolyticum* collagenases bind to partially untwisted or undertwisted regions of collagen. This work is described in U.S. Pat. No. 9,579,273, which is hereby incorporated herein by reference in its entirety. This affinity for unwound collagen allows these domains to be used to target the collagen-binding agents of the present invention to lesions, which are characterized by disrupted collagen fibers.

The collagen-binding domain may also be any one of the polypeptides provided as SEQ ID NOs:6-53, which include collagen-binding domains derived from collagenases from various bacterial species, i.e., *Clostridium* and *Bacillus* species. While the collagen-binding domains from different bacteria share a relatively small amount of sequence identity, they all bind to collagen in a similar fashion. Thus, any of the collagen-binding domains disclosed herein, as well as variants and fragments thereof, may be used in the collagen-binding agents of the present invention.

The phrase "derived from" indicates that the collagen-binding domain is a fragment of the full-length collagenase protein, that it contains amino acid changes relative to the wild-type protein, or a combination thereof. A collagen-binding domain may be derived from any collagen-binding protein by selecting a portion of the protein that binds to collagen. It is only required that the collagen-binding domain retains the ability to bind collagen. Suitably, the collagen-binding domains used with the present invention lack collagenase activity. "Collagenase activity" refers to the ability of a polypeptide to degrade or breakdown collagen, which would be harmful to a subject. For example, extensive degradation of collagen in connective tissues results in gas gangrene. The collagenase-derived collagen-binding domains used with the present invention may lack collagenase activity either because they comprise only a portion of a full-length collagenase protein or because they contain a mutation that eliminates collagenase function.

In previous work, the inventors developed "tandem collagen-binding domain" proteins (abbreviated herein as CBD-CBD) that comprises two collagen-binding domains, allowing for tighter binding to collagen via bridging of two collagen fibrils. This work is described in US Patent Publication No. 2019/0376053, which is hereby incorporated herein by reference in its entirety. Because of their increased affinity for collagen, these tandem collagen-binding domain proteins may be more effective than their single-domain counterparts for certain applications, particularly for applications that require highly localized treatment. Thus, in some embodiments, the collagen-binding domain is a tandem collagen-binding domain. The tandem collagen-binding domain may include two collagen-binding domains of the same type or may include two collagen-binding domains of different types (i.e. two collagen-binding domains from two different origins). Furthermore, the two collagen-binding domains may be from the same bacterial species or from two different bacterial species. Each collagen-binding domain may be individually selected from the group consisting of SEQ ID NOs:6-45, a polypeptide having at least 90%, 92%, 94%, 95%, 96%, 97%, 98%, or 99% sequence identity to SEQ ID NOs:6-45, and a fragment of at least 8 consecutive amino acids of SEQ ID NOs:6-45 capable of binding to collagen. In some embodiments, the collagen-binding domain comprises a naturally occurring tandem collagen-binding domain. Suitable naturally occurring tandem collagen-binding domains include those disclosed as SEQ ID NO:46-53. For instance, the collagen-binding domain utilized in the fusion protein tested in the Examples is the tandem collagen-binding domain of SEQ ID NO:46, which comprises the s3a and s3b domains from the *C. histolyticum* collagenase ColG. Thus, in one embodiment, the collagen-binding domain comprises SEQ ID NO:46. The two collagen-binding domains within a tandem collagen-binding domain may be linked by a covalent bond and/or a linker or spacer moiety. In some embodiments, the two domains are linked via a native collagen-binding domain linker. Suitable native collagen-binding domain linkers include, but are not limited to, those disclosed as SEQ ID NO:54-61.

Therapeutic Agent

The collagen-binding agents of the present invention also comprise a therapeutic agent. The term "therapeutic agent" refers to a pharmaceutically active compound. Exemplary therapeutic agents include, without limitation, polypeptides, polynucleotides, small molecules, hormones, carbohydrates, and lipids. In some embodiments, the therapeutic agent is selected from the group consisting of a fibroblast growth factor (FGF) polypeptide, parathyroid hormone (PTH), a PTH/parathyroid hormone-related peptide (PTHrP) receptor agonist, a PTH/PTHrP receptor antagonist, a bone morphogenic protein (BMP), granulocyte colony stimulating factor (G-CSF), an anti-sclerostin antibody, insulin-like growth factor 1 (IGF-1), vascular endothelial growth factor (VEGF), a transforming growth factor beta (TGF-β) protein, a TGF-β receptor, transforming growth factor alpha (TGF-α), a keratinocyte growth factor (KGF) protein, CT, a growth hormone (GH) protein, granulocyte-macrophage colony-stimulating factor (GM-CSF), epidermal growth factor (EGF), a platelet-derived growth factor (PDGF) protein, celiprolol, and connective tissue growth factor (CTGF). See U.S. Pat. Nos. 8,450,273; 9,579,273; and International Publication no. WO2018/148573, which are incorporated herein by reference.

In preferred embodiments, the therapeutic agent is a fibroblast growth factor (FGF) polypeptide. FGF polypeptides are a family of cell signaling proteins produced by macrophages that play an important role in various cellular processes like cell proliferation, migration, and differentiation. They are known to induce processes such as regeneration, morphogenesis, and angiogenesis. For example, FGF polypeptides are known to bind to heparin to increase the efficiency of mitogenic activity. In humans, 23 members of the FGF family have been identified. FGF1 is known to play a crucial role in wound healing and other significant clinical conditions. For example, FGF1 has been shown to promote nerve regeneration and angiogenic activity, which are critical for wound healing. FGF2, which is also referred to herein as basic fibroblast growth factor (bFGF), has been hypothesized to mediate the formation of new blood vessels (i.e., angiogenesis) during wound healing. Further, preliminary animal studies suggest that FGF2 protects the heart from injury associated with a heart attack, reducing tissue death and promoting improved function after reperfusion. Suitable FGF polypeptides for use with the present invention include those disclosed as SEQ ID NOs:2-5. In the Examples, the inventors utilized the wild-type FGF2 polypeptide of SEQ ID NO:4 as the therapeutic agent in their collagen-binding agent. Thus, in some embodiments, the FGF polypeptide comprises SEQ ID NO:4. The FGF1 and FGF2 polypeptides described herein may be full-length polypeptides (i.e., SEQ ID NOs:2-5) or may be functional fragments of a full-length FGF polypeptide.

In some embodiments, the FGF polypeptide is a wild-type FGF1 (SEQ ID NO:2) or FGF2 (SEQ ID NO:4) polypeptide. In other embodiments, the FGF polypeptide is hyper-stable variant FGF1 (SEQ ID NO:3) or FGF2 (SEQ ID NO:5) polypeptide. Although FGF1 and FGF2 polypeptides are promising therapeutics, they have low intrinsic stability and are highly susceptible to proteolytic degradation, especially by thrombin, which is usually present in abundance in the fibrin clots at the site of a wound. In previous work, the inventors developed hyper-stable variants of human FGF1 and FGF2 that are not only resistant to thrombin but also exhibit heparin-independent mitogenic/wound healing activity. This work is described in US Patent Publication No. 2019/0284252, which is hereby incorporated herein by reference in its entirety. Due to the extraordinary physical and bioactivity of these engineered variants, the present inventors have named the engineered human FGF1 variant (which comprises the mutations Q41P, S48L, H94S, K113N, and R123E) "super human acidic fibroblast growth factor 1 (shFGF1)" and have named the engineered human FGF2 variant (which comprises the mutations Q65L, N111S, K128N, and K138E) "super human acidic fibroblast growth factor 2 (shFGF2)." The inventors demonstrated that shFGF1 shows no signs of degradation even when stored at room temperature (25° C.) for over 3 months. Specifically, shFGF1 denatures only at temperatures higher than 80° C., and it exhibits a wider range of pH stability (4.0-10.0) than wild-type human FGF1. shFGF1 shows no binding affinity to heparin but its mitogenic activity is higher than that of wild-type FGF1. Importantly, the inventors have shown that shFGF1 activates pathways involving the anti-apoptotic protein kinases PI3K-Akt and MEK1/2-ERK1/2. Thus, treatment with shFGF1 is expected to attenuate lethal myocardial reperfusion injury and limit myocardial infarct size. Also encompassed are FGF proteins having at least 90%, 92%, 94%, 95%, 96%, 97%, 98%, or 99% sequence identity to the polypeptides of SEQ ID NO: 2-5.

Protease Cleavage Site

The collagen-binding agents of the present invention also comprise a protease cleavage site. In some embodiments, the protease cleavage site is the cleavage site of a matrix metalloproteinase (MMP). MMPs are a family of calcium-dependent, zinc-containing endopeptidases that degrade extracellular matrix proteins. Exemplary MMPs for use with the present invention include MMP-1, MMP-2, MMP-3, MMP-7, MMP-8, MMP-9, MMP-10, MMP-13, MMP-14, and MMP-18, which cleave various forms of collagen. Suitable MMP cleavage sites for inclusion in the collagen-binding agents include, without limitation, GPQGIA (SEQ ID NO:66), GPQGIL (SEQ ID NO:67), GPQGLA (SEQ ID NO:68), GPQGLL (SEQ ID NO:69), GPLGIA (SEQ ID NO:70), GPLGIL (SEQ ID NO:71), GPLGLA (SEQ ID NO:72), GPLGLL (SEQ ID NO:73), GPRGLQ (SEQ ID NO:74), and GPTGLA (SEQ ID NO:75). In the fusion protein tested in the Examples, the inventors utilized the cleavage sequence for MMP-1 (i.e., GPLGIAGP; SEQ ID NO:65). Thus, in some embodiments, the protease cleavage site comprises SEQ ID NO:65.

Wound healing occurs in four phases: hemostasis phase, inflammatory phase, proliferative phase, and maturation phase. At the end of the inflammatory phase, the expression of specific MMPs (i.e., MMP-2, MMP-8, MMP-9, and MMP-13 initially, then MMP-10 and MMP-14) is upregulated. Thus, including a cleavage site for one such MMP between the collagen-binding domain and the therapeutic agent in a collagen-binding agent allows the therapeutic agent to be released during this critical phase of wound healing. Because different MMPs are upregulated at slightly different points in the wound healing process, the MMP cleavage site included in the collagen-binding agent may be selected such that the therapeutic agent is released at the stage in which it will provide the most benefit. A composition comprising more than one fusion protein is also envisioned. The composition may comprise fusion proteins with various cleavage sites to allow for extended release of the therapeutic agent over the different healing phases based on the MMP upregulated at specific phases of healing.

Construction

The collagen-binding agents of the present invention may be constructed in several ways. In some embodiments, the collagen-binding agent is a fusion protein, and the therapeutic agent is a polypeptide that forms one functional segment of the fusion protein. The term "fusion protein" refers to a single polypeptide comprising at least two functional segments. For example, the fusion proteins of the present invention comprise a collagen-binding segment comprising the collagen-binding domain, a protease cleavage site, and a therapeutic segment comprising the therapeutic agent. Each polypeptide segment may comprise a synthetic polypeptide, a naturally occurring polypeptide, a fragment of a naturally occurring polypeptide, or a variant polypeptide comprising one or more mutations. The polypeptide segments of the fusion protein can be linked together directly (e.g., via a peptide bond or chemical cross-linking) or indirectly (e.g., via a polypeptide linker).

In some embodiments, the collagen-binding domain, protease cleavage site, and therapeutic agent are conjugated via polypeptide linkers (i.e., polypeptides that bridge two protein segments). The polypeptide linkers may be any length and may include traditional or non-traditional amino acids. For example, the peptide linker may be 1-100 amino acids long, and is suitably 5, 10, 15, 20, 25 or more amino acids long. The linker may "flexible" such that it has no required fixed structure in solution and the adjacent protein segments are free to move relative to one another, e.g., allowing the collagen-binding segment to bind to collagen without steric hindrance from the therapeutic segment. Preferred amino acid residues for flexible linker sequences include glycine, alanine, serine, threonine, lysine, arginine, glutamine, and glutamic acid, but are not limited thereto. In some embodiments, the linker is a linker that is natively found in a collagen-binding domain, e.g., the linkers of SEQ ID NOs: 54-61. In some embodiments, the polypeptide linker is a polycystic kidney disease domain derived from a bacterial collagenase. "Polycystic kidney disease (PKD)" domains comprise an Ig-like fold consisting of a beta-sandwich of seven strands in two sheets with a Greek key topology. In some embodiments, the PKD domain comprises SEQ ID NO:62 or SEQ ID NO:63.

In other embodiments, the therapeutic agent is linked to a polypeptide comprising the protease cleavage site and the collagen-binding domain via chemical cross-linking. In embodiments in which the therapeutic agent is a polypeptide, it may be cross-linked through an amino group by a reagent such as disuccinimidyl glutarate or glutaraldehyde. It may also be cross-linked through an amino group by derivatizing one polypeptide with SANH (succinimidyl-4-hydrazinonicotinate acetone hydrazone) and the other with SFB (succinimidyl-4-formyl benzoate), and then mixing the two derivatized polypeptides. Two polypeptides can be cross-linked between an amino group of one polypeptide and a carboxyl group of the other polypeptide via reaction with EDC (1-ethyl-3-[3-dimethylaminopropyl]carbodiimide hydrochloride). Other suitable cross-linking methods are described in U.S. Patent Application Publication Nos. 2006/0258569 and 2007/0224119.

In other embodiments, the therapeutic agent is linked to the protease cleavage site and collagen-binding domain using a tag system, i.e., a pair of agents that bind to each other with high affinity. Suitable tag systems include, without limitation, biotin/avidin, biotin/streptavidin, and digoxigenin (DIG) systems.

In some embodiments, the collagen-binding agent is produced as a fusion protein that further comprises a purification tag, i.e., a moiety that facilitates isolation of the fusion protein. Suitable purification tags include, but are not limited to, histidine (His), hemagglutinin (HA), cMyc, glutathione S-transferase (GST), Flag, V5, and NE tags. In preferred embodiments, the purification tag is a His tag or a GST tag. In some embodiments, the purification tag is removed from the collagen-binding agent after it has been purified. This can be accomplished by including a protease cleavage site between the purification tag and the collagen-binding agent within the fusion protein and treating the fusion protein with the cognate protease following purification. For instance, in Example 3, the inventors included a thrombin cleavage site in their fusion protein to allow a GST tag to be removed via treatment with thrombin following affinity purification with glutathione-Sepharose beads. However, any protease cleavage site may be used for this purpose.

In the Examples, the inventors generated a fusion polypeptide comprising, from N-terminus to C-terminus: an FGF polypeptide, an MMP cleavage site, and a collagen-binding domain. Thus, in some embodiments, the C-terminus of the therapeutic agent is linked to the N-terminus of the protease cleavage site, and the C-terminus of the protease cleavage site is linked to the N-terminus of the collagen-binding domain, as depicted in FIG. 1. In certain embodiments in which the collagen-binding agent further comprises a PKD domain, the N-terminus of the PKD is linked to the C-terminus of the protease cleavage site and the C-terminus of the PKD is linked to the N-terminus of the collagen-binding domain.

In some embodiments, the fusion polypeptide is that of SEQ ID NO:1 (i.e., the fusion protein tested in the Examples), which comprises from N-terminus to C-terminus: wild-type FGF2 (SEQ ID NO:4), the cleavage sequence for MMP-1 (SEQ ID NO:65), and a natural tandem collagen-binding domain comprising the s3a and s3b domains of the *C. histolyticum* collagenase ColG (SEQ ID NO:46).

Definitions

The terms "polypeptide," "protein," and "peptide" are used interchangeably herein to refer to a series of amino acid residues connected by peptide bonds between the alpha-amino and carboxy groups of adjacent residues, forming a polymer of amino acids. Polypeptides may include modified amino acids. Suitable polypeptide modifications include, but are not limited to, acylation, acetylation, formylation, lipoylation, myristoylation, palmitoylation, alkylation, isoprenylation, prenylation, amidation at C-terminus, glycosylation, glycation, polysialylation, glypiation, and phosphorylation. Polypeptides may also include amino acid analogs. The terms "protein" and "polypeptide" are often used in reference to relatively large polypeptides, whereas the term "peptide" is often used in reference to small polypeptides, but usage of these terms in the art overlaps.

The polypeptides provided herein include fragments of full-length polypeptides. For example, the collagen-binding domains used with the present invention may comprise fragments of SEQ ID NOs:6-53. As used herein, a "fragment" is a portion of an amino acid sequence which is identical in sequence to, but shorter in length than, a reference polypeptide. A fragment may comprise at least 8, 10, 15, 20, 25, 30, 40, 50, 60, 70, 80, 90, 100, or more contiguous amino acid residues of a reference polypeptide. Thus, the collagen-binding domain fragments of the present invention may comprise or consist essentially of a contiguous portion of a full-length collagen-binding domain (i.e., SEQ ID NOs:6-53). Fragments may be preferentially selected from certain regions of a molecule. A fragment may include an N-terminal truncation, a C-terminal truncation, or both truncations relative to the full-length collagen-binding domain or agent. The N-terminal and/or C-terminal truncations may include removal of 1, 2, 3, 4, 5, 6, 7, 8, 9, or 10 amino acid residues from a reference polypeptide. Suitably, the polypeptide fragments retain at least 20%, 40%, 60%, 80%, or 100% of the biological activity of the reference polypeptide (e.g., collagen-binding, would healing activity).

The polypeptides provided herein also include variant polypeptides, i.e., engineered polypeptides that comprise substitution mutations relative to a wild-type reference polypeptide. For example, the FGF1 variant shFGF1 comprises the mutations Q41P, S48L, H94S, K113N, and R123E relative to the wild-type FGF1 protein, and the FGF2 variant shFGF2 comprises the mutations Q65L, N111S, K128N, and K138E relative to the wild-type FGF2 protein. A variant may comprise one or more insertions, deletions, or substitutions of an amino acid residue relative to a wild-type reference molecule. An "insertion" refers to a change in an amino acid sequence resulting in the addition of one or more amino acid residues. An insertion may add 1, 2, 3, 4, 5, 10, 20, 30, 40, 50, 60, 70, 80, 90, 100, 150, 200, or more amino acid residues. A "deletion" refers to a change in the amino acid sequence that results in the absence of one or more amino acid residues. A deletion may remove 1, 2, 3, 4, 5, 10, 20, 50, 100, 200, or more amino acids residues. A "substitution" refers to a change in an amino acid sequence in which one amino acid is replaced with a different amino acid due to a point mutation. The amino acid substitution may be a conservative replacement (i.e., a replacement with an amino acid that has similar properties) or a radical replacement (i.e., a replacement with an amino acid that has different properties). Suitably, the variant polypeptides retain at least 20%, 40%, 60%, 80%, or 100% of the biological activity of the reference polypeptide (e.g., collagen-binding, would healing activity).

"Percentage of sequence identity"" or "percentage of sequence similarity"" is determined by comparing two optimally aligned sequences over a comparison window. The aligned sequences may comprise additions or deletions (i.e., gaps) relative to each other for optimal alignment. The percentage is calculated by determining the number of matched positions at which an identical nucleic acid base or amino acid residue occurs in both sequences, dividing the number of matched positions by the total number of positions in the window of comparison and multiplying the result by 100 to yield the percentage of sequence identity. Protein and nucleic acid sequence identities are evaluated using the Basic Local Alignment Search Tool ("BLAST"), which is well known in the art (*Proc. Natl. Acad. Sci. USA* (1990) 87: 2267-2268; *Nucl. Acids Res*. (1997) 25: 3389-3402). The BLAST programs identify homologous sequences by identifying similar segments, which are referred to herein as "high-scoring segment pairs", between a query amino acid or nucleic acid sequence and a test sequence which is preferably obtained from a protein or nucleic acid sequence database. Preferably, the statistical significance of a high-scoring segment pair is evaluated using the statistical significance formula (*Proc. Natl. Acad. Sci. USA* (1990) 87: 2267-2268), the disclosure of which is incorporated by reference in its entirety. The BLAST programs can be used with the default parameters or with modified parameters provided by the user. For example, the variant collagen-binding domains used with the present invention may have at least 50%, 55%, 60%, 65%, 70%, 75%, 80%, 85%, 90%, 95% 98%, or 99% sequence identity to any one of SEQ ID NOs:6-53. Similarly, the therapeutic agents used herein may be variants of the wild-type sequences and have at least 50%, 55%, 60%, 65%, 70%, 75%, 80%, 85%, 90%, 95% 98%, or 99% sequence identity to any one of SEQ ID NO: 2-5 or any of the sequences encoding the therapeutic agents described herein.

Pharmaceutical Compositions:

In a second aspect, the present invention provides pharmaceutical compositions comprising a collagen-binding agent disclosed herein. The pharmaceutical compositions may include a pharmaceutically acceptable carrier, excipient, or diluent that is nontoxic to the cell or animal being exposed thereto at the dosages and concentrations employed. Often a pharmaceutical agent is in an aqueous pH buffered solution. Pharmaceutically acceptable carriers are known in the art and include, but are not limited to, diluents (e.g., Tris-HCl, acetate, phosphate), preservatives (e.g., Thimerosal, benzyl alcohol, parabens), solubilizing agents (e.g., glycerol, polyethylene glycerol), emulsifiers, liposomes, nanoparticles, and adjuvants. Pharmaceutically acceptable carriers may be aqueous or non-aqueous solutions, suspensions, or emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions, or suspensions, including saline and buffered media.

In some embodiments, the pharmaceutical compositions are formulated for topical administration. For example, the pharmaceutical compositions may be formulated as gels, creams, or liposome preparations suitable for topical delivery. The pharmaceutical compositions may be formulated for delivery to the lower layers of the skin or facilitate extended release of the pharmaceutical at the site of application.

Biomedical Devices:

In a third aspect, the present invention provides biomedical devices comprising a coating that comprises a collagen-binding agent disclosed herein. The term "biomedical device" refers to a device that is administered to an animal for a medical purpose, e.g., for the diagnosis, treatment, or prevention of a disease or condition. Exemplary biomedical devices include, but are not limited to, stents, artificial ureters, diaphragms, intrauterine devices, heart valves, catheters, denture liners, prosthetic devices, ophthalmic lens applications, and artificial skin. In certain preferred embodiments, the biomedical device is a stent.

The collagen-binding agent may be coated onto the biomedical device using any suitable means known in the art. For example, the biomedical device may be coated with a material to which the collagen-binding agent has an affinity (e.g., collagen) or may be coated with a material to which the collagen-binding agent may be chemically linked (e.g., a biodegradable polymer). The collagen used to coat the biomedical device may be a synthetic collagen or a natural collagen of any type (i.e., type I, type II, type III, or type IV). Suitably, the collagen is from the same species as the subject to which the biomedical device is to be administered. Suitable biodegradable polymers that can be used to coat the biomedical device include, without limitation, polyphosphazenes, polyanhydrides, polyacetals, poly(ortho esters), polyphosphoesters, polycaprolactone, polyurethanes, polylactide, polycarbonates, and polyamides.

Methods:

In a fourth aspect, the present invention provides methods of treating a condition. In a first embodiment, the methods comprise administering a collagen-binding agent or a pharmaceutical composition disclosed herein to a subject in an amount effective to treat the condition. In a second embodiment, the methods comprise administering a biomedical device disclosed herein to subject in need of treatment with the therapeutic agent.

The methods of the present invention can be used to target any therapeutic agent to sites of exposed collagen. Thus, the methods may be useful for the treatment of a variety of conditions including, without limitation, a wound, a bone condition, a spinal fusion, an ischemic heart disease, a peripheral nerve disorder, a spinal cord injury, and a kidney disease.

As used herein, "treating" or "treatment" describes the management and care of a subject for the purpose of combating a disease, condition, or disorder. Treating includes the administration of a collagen-binding agent, pharmaceutical composition, or biomedical device disclosed herein to prevent the onset of the symptoms or complications, to alleviate the symptoms or complications, to decrease recovery time, or to eliminate the disease, condition, or disorder.

The collagen-binding agents, pharmaceutical compositions, and biomedical devices described herein may be administered by any means known to those skilled in the art. As used herein, the terms "administering" and "administration" refer to the introduction of a substance into a subject's body. Such methods include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration, and subcutaneous administration. Administration can be continuous or intermittent.

The biomedical devices should be administered by a method that is appropriate in view of the particular device and condition to be treated. In some embodiments, the biomedical device is implanted into the subject. In particular embodiments, the biomedical device is implanted into an artery of the subject. In other embodiments, the biomedical device is applied to the skin or a tissue of the subject (e.g., to skin or tissue comprising a wound).

The collagen-binding agents and pharmaceutical compositions can be administered as a single dose or as divided doses. For example, the composition may be administered two or more times separated by 4 hours, 6 hours, 8 hours, 12 hours, a day, two days, three days, four days, one week, two weeks, or by three or more weeks. Optionally, such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months.

The term "amount effective to treat the condition" refers to an amount that produces desirable biological or clinical results, e.g., reducing, alleviating, inhibiting, or preventing one or more symptoms of the condition. In some embodiments, the effective amount is an amount suitable to promote wound healing or provide a cardioprotective effect.

It will be appreciated that the specific dosage of the collagen-binding agent that is administered in any given case will be adjusted in accordance with the composition(s) being administered, the condition to be treated, the condition of the subject, and other relevant medical factors that may modify the activity of the compositions or the response of the subject. For example, the specific dose for a particular subject depends on age, body weight, general state of health, diet, the timing and mode of administration, the rate of excretion, medicaments used in combination and the severity of the particular condition to which the therapy is applied. Dosages for a given patient can be determined using a conventional pharmacological protocol. For example, in embodiments that utilize FGF1 or FGF2 polypeptides as a therapeutic agent, suitable dosage ranges may be on the order of several hundred micrograms of effective ingredient with a range from about 0.01 to 10 mg/kg/day, preferably in the range from about 0.1 to 1 mg/kg/day.

In some embodiments, the collagen-binding agent is co-administered with another therapeutic. Suitable therapeutics for co-administration with the collagen-binding agent include, without limitation, anti-platelet therapeutics (e.g., targeting P2Y12, GPIIb/IIIa or COX1), anti-coagulant therapeutics (e.g., enzyme replacement therapy, heparin/heparin mimic), cytotoxic therapeutics to control restenosis, hypertension therapeutics targeting RAS, or stem cell therapeutics.

The "subject" to which the methods are applied may be a mammal or a non-mammalian animal, such as a bird. Suitable mammals include, but are not limited to, humans, cows, horses, sheep, pigs, goats, rabbits, dogs, cats, bats, mice, and rats. In certain embodiments, the methods may be performed on lab animals (e.g., mice and rats) for research purposes. In other embodiments, the methods are used to treat commercially important farm animals (e.g., cows, horses, pigs, rabbits, goats, sheep, and chickens) or companion animals (e.g., cats and dogs). In a preferred embodiment, the subject is a human.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Example 1: Generation of the bFGF-CBD-CBD Fusion Protein

In the following Example, the inventors describe the expression and purification of a collagen-binding fusion protein that comprises a human basic fibroblast growth factor polypeptide (bFGF; also known as FGF2) fused to a tandem collagen-binding domain polypeptide (CBD-CBD) via a linker peptide that comprises the cleavage site of matrix metalloproteinase-1 (MMP-1), such that these the bFGF and CBD-CBD portions of the fusion protein can be cleaved apart by MMP-1. See FIG. 1 and SEQ ID NO: 1.

Strain and Plasmid Construction

BL21(DE3) competent *E. coli* were purchased from New England Biolabs Inc. and used as a host to produce bFGF-CBD-CBD. The pBAD/Myc-His plasmid was purchased from Invitrogen Life Technologies. This plasmid contains the araBAD promoter and the araC gene. The araC gene encodes a protein that regulates the araBAD promoter, resulting in tight, dose-dependent, L-arabinose-inducible regulation of heterologous gene expression. The plasmid also contains a gene encoding lactamase, which provides ampicillin resistance and allows for selection of transformants that harbor the plasmid using this antibiotic. The DNA sequence encoding the bBFGF-CBD-CBD protein (which is 424 amino acids in length) was purchased from IDT and cloned into the pBAD/Myc-His plasmid downstream of a sequence encoding a polyhistidine tag (His-tag).

Protein Expression

A single colony of BL21 *E. coli* comprising the pBAD bFGF-CBD-CBD plasmid was selected from a plate and inoculated into a 50 ml sterile tube containing 10 ml of LB media supplemented with 75 µg/ml ampicillin. The culture was incubated at 37° C. with shaking at 250 rpm overnight. L-arabinose was used to induce expression of His-tagged bFGF-CBD-CBD from the plasmid at the mid-exponential phase of growth.

Cell Lysate Preparation

Cells were collected by centrifugation at 4° C., 4,500 rpm for 45 minutes. The bacterial pellet was suspended by adding 5 ml of 10 mM phosphate buffer supplemented with 0.50 of a protease inhibitor cocktail. Sonication was used to lyse cells.

Protein Purification

Cell lysates were filtered through a 0.20 μm filter. A HiTrap IMAC FF column from GE Healthcare-Bio-Sciences (Uppsala, Sweden) was equilibrated with 0.2 M nickel and 10 mM sodium phosphate buffer (pH 7.3). His-tagged bFGF-CBD-CBD was eluted from the column using 250 mM imidazole in 10 mM sodium phosphate buffer (pH=7.3).

Expression Analysis

Expression of bFGF-CBD-CBD was confirmed by running the purified sample in a polyacrylamide (SDS-PAGE) gel and staining for His-tagged protein using a Pierce™ 6×His Protein Tag Stain Reagent Set purchased from Thermo Fisher Scientific. Expression of bFGF-CBD-CBD was also confirmed by western blot using anti-His-tag antibodies.

Example 2: Assessment of the bFGF-CBD-CBD Fusion Protein

Figure 3:
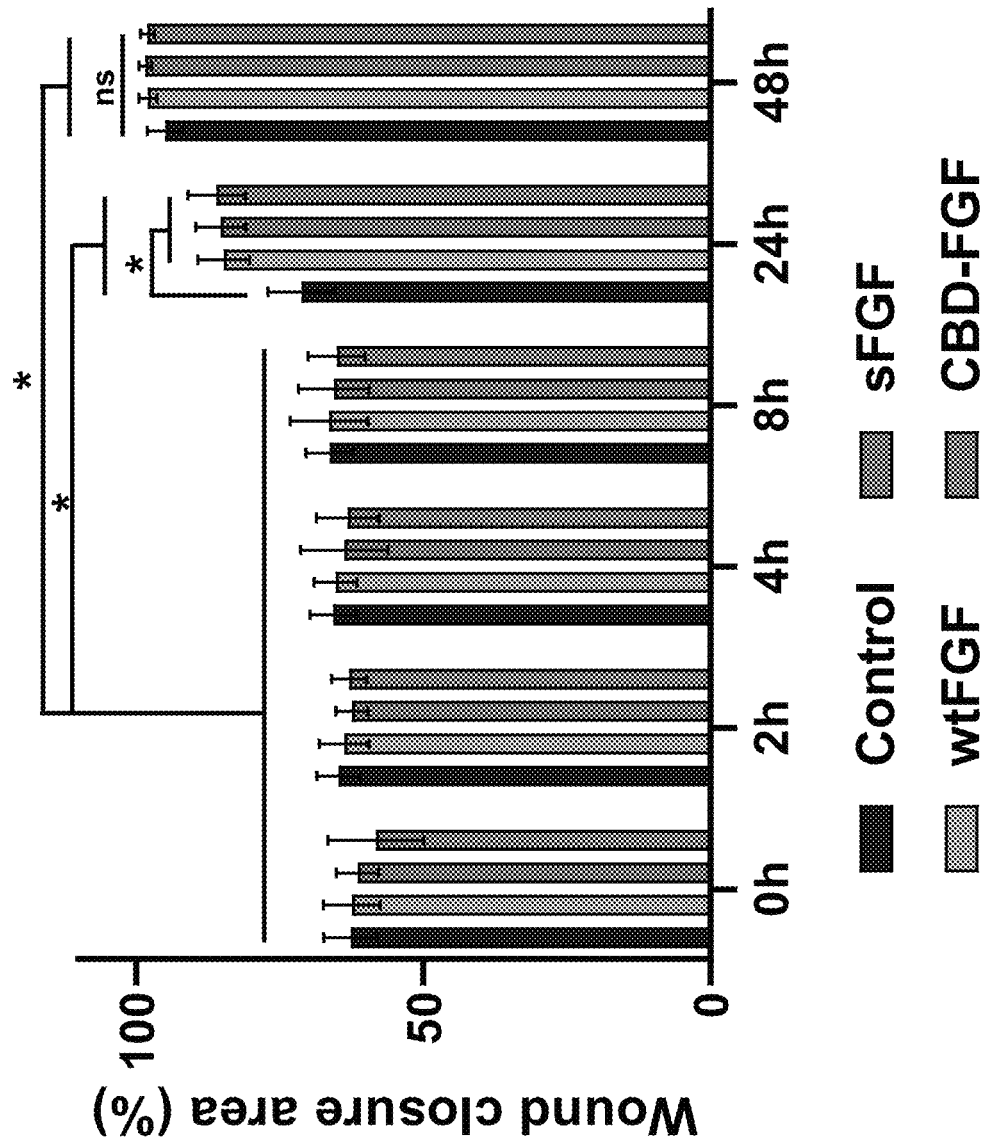
FIG. 3 is a bar graph showing the results of a cardiac fibroblast scratch assay in which the cardioprotective function of the bFGF-CBD-CBD fusion protein (CBD-FGF) was compared to that of wild-type FGF (wtFGF), super FGF (sFGF), and no FGF (control).

The bFGF-CBD-CBD fusion protein was first subjected to efficacy tests in vitro. First, cardioprotective function will be assessed using a cardiac fibroblast scratch assay [1]. Briefly, rat ventricular fibroblasts were isolated from 2-day old neonatal rat pups, seeded in 12-well plates, and grown in 2% serum medium. Two days after seeding, the cell monolayer was scraped in a straight line with a p200 pipet tip. Cell debris was removed by washing the cells once with 1 mL of medium supplemented with bFGF-CBD-CBD, super FGF, or no FGF. Samples were imaged every 6 hours for the next 24 hours and the degree of wound closure stimulated by the various treatments was determined. The results of this analysis revealed that the untreated control cultures healed slower than the cultures treated with bFGF-CBD-CBD (CBD-FGF) or super FGF (sFGF) (FIG. 3). In fact, wound healing was accelerated by 11% in the cultures treated with bFGF-CBD-CBD as compared to the untreated control cells. Notably, the baseline healing response that was observed in the control cultures was expected because the cells were grown in media containing 10% FBS, which contains growth factors that stimulate the recovery cultured cells. These results provide promising evidence that the bFGF-CBD-CBD fusion protein will be effective in vivo.

Figure 4:
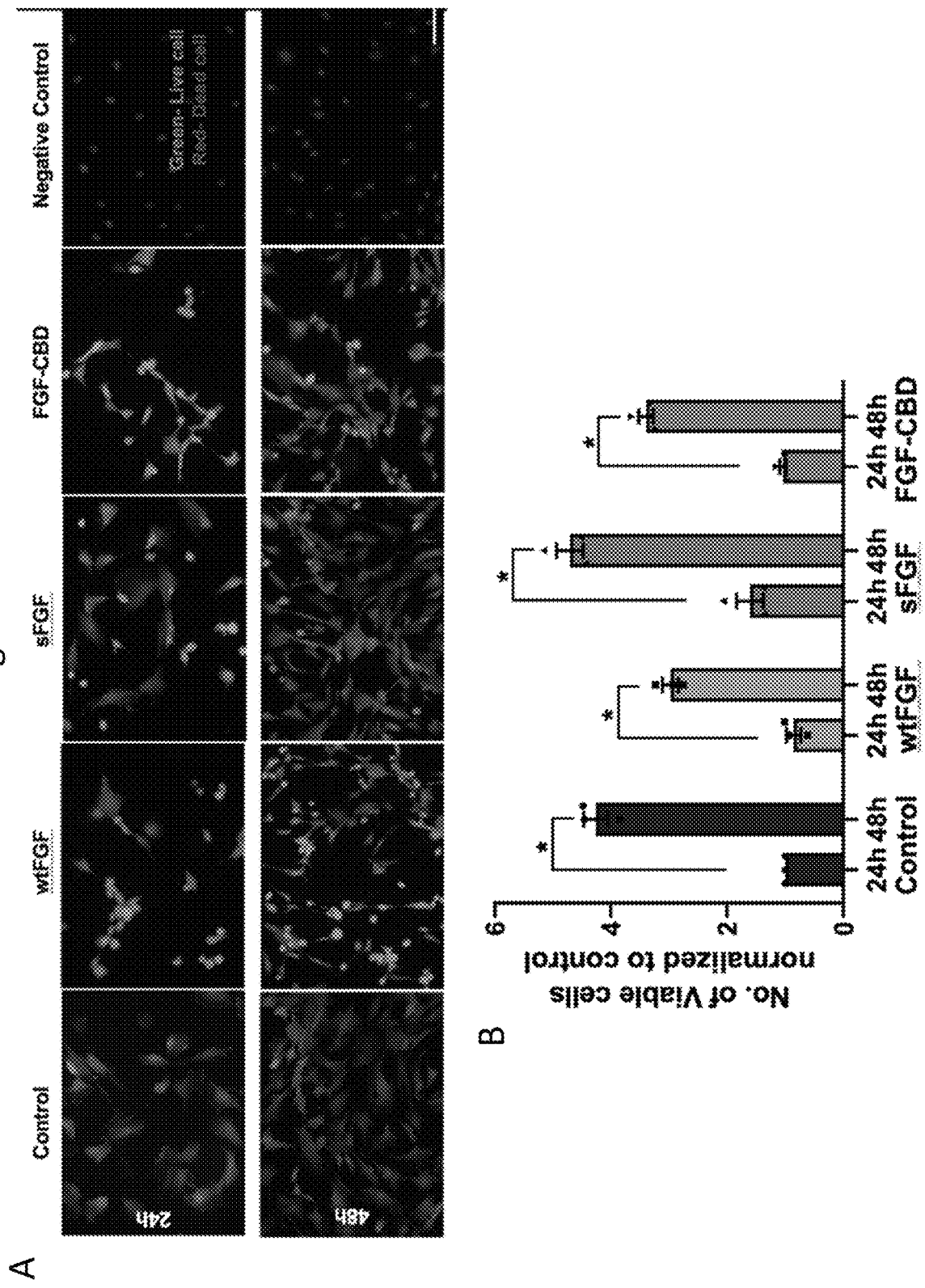
FIG. 4 demonstrates that the bFGF-CBD-CBD fusion protein does not negatively impact cell viability. A live/dead assay kit was used to quantify the percentage of live cells in cultures treated with wild-type FGF (wtFGF), super FGF (sFGF), the bFGF-CBD-CBD fusion protein (FGF-CBD), or no FGF (control) after 24 and 28 hours. Images of the cells were taken using a fluorescence microscope (A) and the number of lives cells was quantified (B).

Second, cell viability of cardiomyocytes and cardiac fibroblasts was determined in the presence of the bFGF-CBD-CBD fusion protein using a live/dead cell viability assay [3]. The cardiac myocytes were obtained at the same time that the fibroblasts were isolated. Human cardiac fibroblasts were seeded onto collagen-coated 25 mm coverslips and placed in a 6-well plate at 200,000 cells per well. After the cells were grown to 80% confluency, they were treated with wild-type FGF (wtFGF), super FGF (sFGF), the bFGF-CBD-CBD fusion protein (FGF-CBD), or no FGF (control). After 24 hours had passed, a live/dead assay kit was used to quantify the percentage of live cells in three samples according to manufacturer's protocol. This assay was repeated after 48 hours using three additional samples. As a negative control, cell-seeded coverslips were treated with methanol for 30 minutes at the 24- and 48-hour timepoints before they were stained. The samples were imaged on a fluorescence microscope to quantify the number of live cells (FIG. 4A). All data points were normalized to the 24-hour control, and a quantitative analysis revealed that the number of cells at 48 hours was significantly increased as compared to at 24 hours in all treatment groups (FIG. 4B; * denotes p<0.001). These results demonstrate that the bFGF-CBD-CBD fusion protein does not negatively impact cell viability.

Additionally, in future work, the ability of bFGF-CBD-CBD to activate cardioprotective signaling mechanisms, namely PI3K-Akt, MEK1/2, and PPARγ signaling, will be assessed via western blotting and ELISA. Relative expression of p-ERK1/2 and p-Akt will be assayed, and PPARγ expression will be determined using commercially available assay kits [2].

Upon successful completion of the in vitro efficacy tests described above, the bFGF-CBD-CBD fusion protein will be tested for in vivo biocompatibility. First, the pro-fibrotic potential and biocompatibility of bFGF-CBD-CBD will be tested in a chronic rat dorsal subcutaneous implantation model. Sterile samples comprising bFGF-CBD-CBD, bFGF, or no FGF will be prepared in a carrier (e.g., collagen powder or poly(lactic-co-glycolic acid) (PLGA)). Sprague Dawley rats will be anesthetized with 3-5% isoflurane in 100% oxygen and maintained at 1-2% isoflurane using a nose cone for the entire duration of the surgery. Adequate depth of anesthesia will be checked with a toe pinch, and the rats will be positioned in a prone position on a warming pad (37° C.). Buprenorphine (0.6 mg/kg) will be administered for analgesia. The dorsal side of the rats will be shaved and treated with a depilatory to remove any traces of hair. The skin will be sterilized with an alcohol wipe followed by a povidone-iodine wipe. Using a scalpel, sterile curved surgical scissors, and tweezers, we will create four ~15 mm diameter sub-dermal pouches for injection of the drug preparations (i.e., one for each of the three preparations and sham (untreated) control) [4, 5]. The incisions will be closed with sterile 4-0 Vicryl sutures, topical tetracycline will be applied, and the wound will be covered with an occlusive dressing (i.e., Tegaderm™). The animals will then be revived from anesthesia with continuous vital sign monitoring. The rats will be closely monitored for the first 1-3 days post-surgery, and 0.3 mg/kg buprenorphine will be administered as needed. The rats will be administered analgesic immediately after surgery, 12 hours post-surgery, and whenever they appear to be in distress/pain. Rats will be sacrificed at 1, 4 and 12 weeks for analysis. The rats will be euthanized and a sterile 10 mm biopsy punch will be used to excise the scaffold and skin tissue around the wound area. This excised tissue will be divided in two. One half of the tissue will be placed in OCT and sectioned for histology, and the other half will be snap frozen for gene and protein analysis [4-7]. Histology sections will be stained with hematoxylin & eosin and Masson's trichrome to assess scar tissue/fibrosis formation and immune cell infiltration. Immunohistochemistry will be used to assess CD68 (a macrophage marker), CD163 (an activated macrophage marker), and α-SMA (an activated fibrogenic cell marker) expression as indicators of inflammation [8].

Second, the hemocompatibility of bFGF-CBD-CBD will be tested on human blood obtained from healthy adult volunteers in a standard static incubation model [9]. Blood will be sampled after 1, 6, 12, and 24 hours of contact with bFGF-CBD-CBD, bFGF, or carrier alone and assessed for platelet activation, complement activation, inflammation, and immune cell activation using commercially available assay kits.

REFERENCES FOR EXAMPLE 2

1. Liang, C. C., A. Y. Park, and J. L. Guan, *In vitro scratch assay: a convenient and inexpensive method for analysis of cell migration in vitro.* Nat Protoc, 2007. 2(2): p. 329-33.

2. Ragab, D., D. M. Abdallah, and H. S. El-Abhar, *Cilostazol renoprotective effect: modulation of PPAR-gamma, NGAL, KIM-1 and IL-18 underlies its novel effect in a model of ischemia-reperfusion.* PLoS One, 2014. 9(5): p. e95313.
3. Perbellini, F., et al., *Investigation of cardiac fibroblasts using myocardial slices.* Cardiovasc Res, 2018. 114(1): p. 77-89.
4. Choi, J. S., K. W. Leong, and H. S. Yoo, *In vivo wound healing of diabetic ulcers using electrospun nanofibers immobilized with human epidermal growth factor (EGF).* Biomaterials, 2008. 29(5): p. 587-96.
5. Dunn, L., et al., *Murine model of wound healing.* J Vis Exp, 2013(75): p. e50265.
6. Galiano, R. D., et al., *Quantitative and reproducible murine model of excisional wound healing. Wound Repair Regen,* 2004. 12(4): p. 485-92.
7. Wong, V. W., et al., *Surgical approaches to create murine models of human wound healing.* J Biomed Biotechnol, 2011. 2011: p. 969618.
8. Duijvelshoff, R., et al., *Host Response and Neo-Tissue Development during Resorption of a Fast Degrading Supramolecular Electrospun Arterial Scaffold.* Bioengineering (Basel), 2018. 5(3).
9. Weber, M., et al., *Blood-Contacting Biomaterials: In Vitro Evaluation of the Hemocompatibility.* Front Bioeng Biotechnol, 2018. 6: p. 99.

Example 3: A Second Plasmid for Expression of the bFGF-CBD-CBD Fusion Protein

The following example describes how the inventors designed and tested a second plasmid for expression of the bFGF-CBC-CBD fusion protein. This second plasmid differs from the plasmid used in Examples 1 and 2 in that (1) it contains a different promoter and regulatory element (i.e., the tac promoter and lacI$^q$ repressor as opposed to the araBAD promoter and araC gene), and (2) it contains a different protein purification tag (i.e., a glutathione-S-transferase (GST) tag as opposed to a His-tag).

While the plasmid used in Examples 1 and 2 offers high yield for protein production solubility of the produced protein was not high. This second plasmid produced higher yield soluble protein. Further, this second plasmid was easy to isolate and contained fewer byproducts.

Construction of the expression system. Two single-stranded oligonucleotides (Collagenase site-Forward: 5'-AATTAGCGGCGGAGGTTCAGGTCCTCTGG-GAATCGCAGGTCCGTCCGGCGGAGGTA GC (SEQ ID NO:76), and Collagenase-site-Reverse: 5'-GC-TACCTCCGCCGGACGGACCTGCGAT-TCCCAGAGGACCTGAACCTCCGCCGCT (SEQ ID NO:77)) were annealed to form a double-stranded DNA fragment encoding the cleavage site of matrix metalloproteinase-1 (MMP-1). The resulting double-stranded DNA fragment was ligated into the pCHG112-bFGF vector, which was digested with EcoRI and SmaI. Insertion of the DNA fragment was confirmed by DNA sequencing. The recombinant plasmid was named pOU693. Competent BL21-CodonPlus-RIL *E. coli* cells (Agilent Technologies Japan) were transformed with pOU693.

Protein purification. Transformed BL21-CodonPlus-RIL were grown in 2×YT medium (16 g Tryptone, 10 g Yeast extract, and 5 g NaCl per liter) supplemented with 2% (wt/vol) glucose, 50 µg/ml ampicillin, and 30 µg/ml chloramphenicol at 37° C. with shaking at 150 rpm to an optical density of 0.5 at 600 nm. Then, the temperature was shifted down to 25° C., and the cells were grown to an optical density of 0.7 at 600 nm. Expression of the GST-tagged fusion protein was induced by the addition of 1 mM isopropyl-β-D-thiogalactopyranoside (IPTG), and the cells were cultured for 5 hours at 25° C. Phenylmethlysulfonyl fluoride (PFSF) was added to the culture to a final concentration of 1 mM, and the cells were harvested by centrifugation at 6,000 rpm for 10 min at 4° C. The cell pellet obtained from 2-liter culture was suspended in 40 ml of 50 mM Tris-HCl (pH 7.5) containing 0.5 M NaCl and 1 mM PMSF and was disrupted in a French pressure cell at 10,000 psi. The lysate was supplemented with 1% Triton X-100, and stirred for 30 min at 4° C., followed by centrifugation at 15,000 rpm for 30 min at 4° C. twice.

Figure 5:
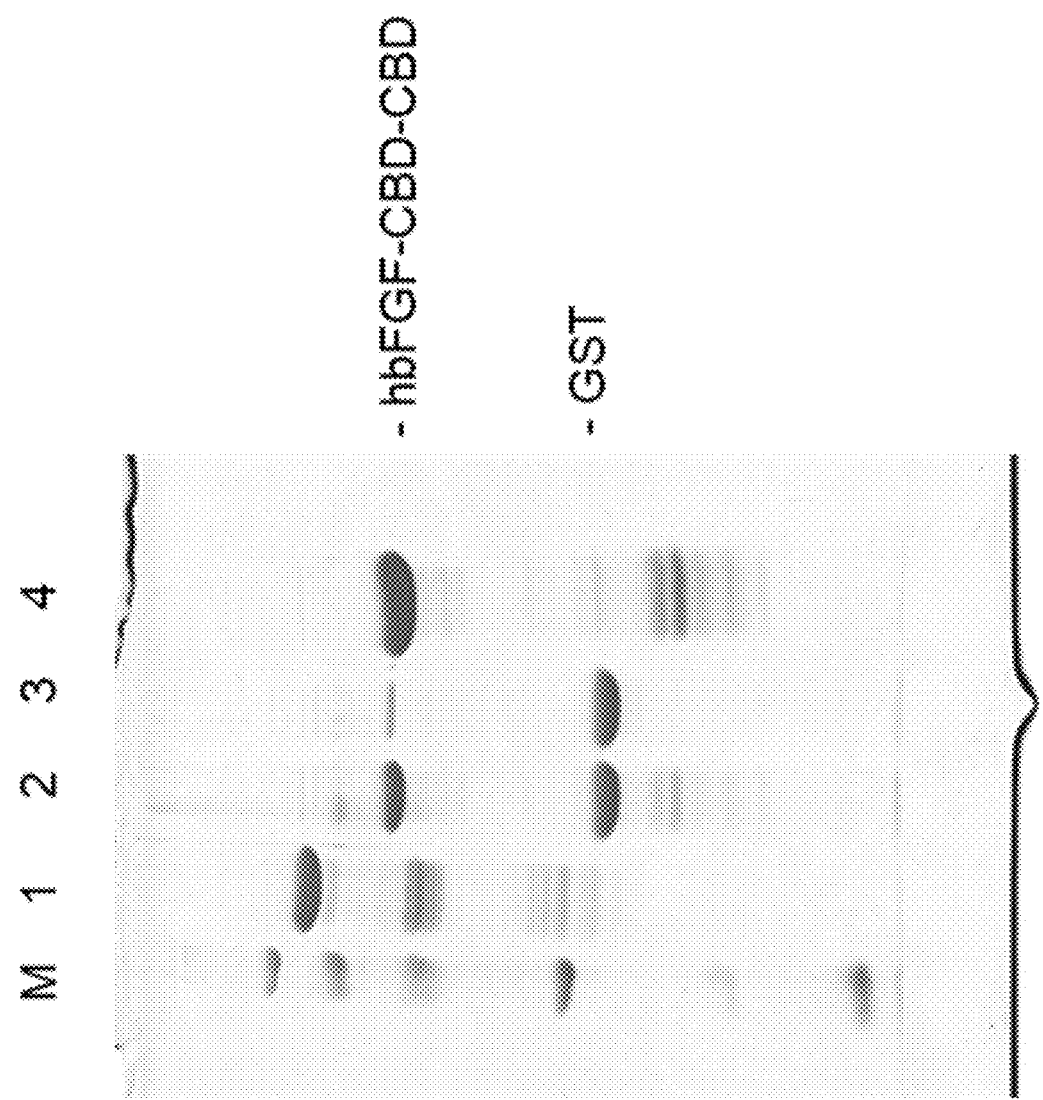
FIG. 5 is a Coomassie-stained SDS-PAGE gel demonstrating the purification of the hbFGF-CBC-CBD fusion protein. The fusion protein was produced as a GST-fusion protein (1). GST-tag was cleaved off using thrombin protease (4). The mixture was then further separated by Heparin-Sepharose column chromatography. Both the unbound (2) and bound (3) fractions were analyzed.

The resulting supernatant was mixed with 10 ml of glutathione-Sepharose (GE Healthcare) beads and stirred for 30 min at 4° C. The beads were washed five times with 10 mM Tris-HCl (pH 7.5), 0.5 M NaCl. The slurry was poured into a column. The fusion protein was eluted with 50 mM Tris-HCl (pH 8.0) containing 0.5 M NaCl and 10 mM reduced glutathione. Fractions containing significant quantities of the fusion protein were combined, and the combined fractions were treated with 10 units of thrombin per mg of eluted protein at 25° C. overnight. The cleavage products were run on an SDS-PAGE gel that was stained with Coomassie blue for protein visualization (FIG. 5). The results of these gels demonstrate that treatment with thrombin resulted in effective removal of the GST tag.

Next, the protein solution was mixed with 2 ml of heparin-Sepharose beads (GE Healthcare) and stirred for 3 hours at 4° C. The beads were washed three times with 10 mM Tris-HCl (pH 7.5), 0.5 M NaCl. The slurry was poured into an EconoColumn, and protein was eluted using a linear gradient of 0.5-2.0 M NaCl in 50 mM Tris-HCl (pH 7.5). Unbound and bound fractions were analyzed by SDS-PAGE (FIG. 5).

Figure 6:
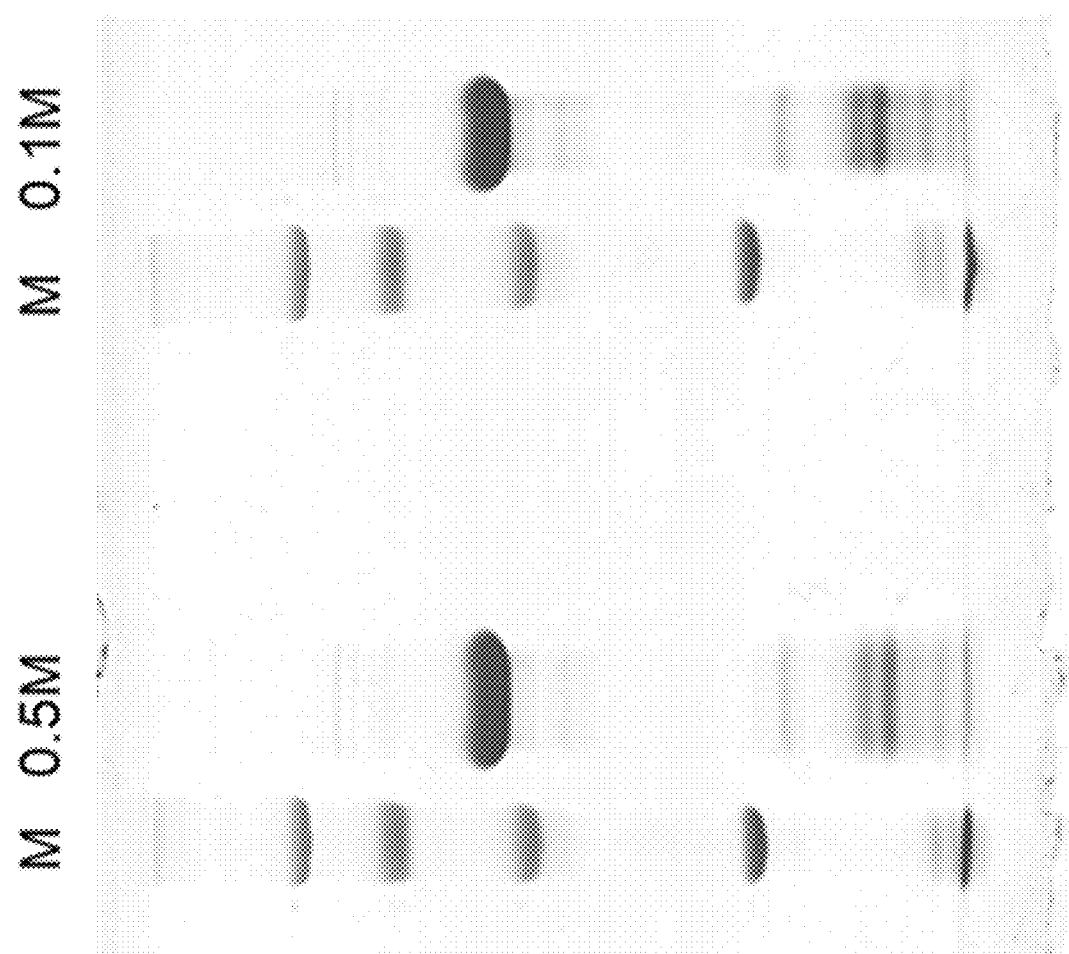
FIG. 6 is a Coomassie-stained 12.5% SDS-PAGE gel demonstrating the solubility of the purified hbFGF-CBC-CBD fusion protein. Following elution from the Heparin-Sepharose column, the fusion protein was first dialyzed against 50 mM TrisHCl (pH7.5), 0.5 M NaCl (7.4 μg, 0.5M), and was then dialyzed against 50 mM TrisHCl (pH7.5), 0.1 M NaCl (7.4 μg, 0.1M). M: 94, 67, 43, 30, 20.1, and 14.4 kDa markers. 0.5M: the fraction dialyzed against the buffer containing 0.5 M NaCl (7.4 µg). 0.1M: the fraction dialyzed against the buffer containing 0.1 M NaCl (7.4 µg).

Fractions containing significant quantities of the fusion protein were pooled and were dialyzed against 50 mM TrisHCl (pH7.5)+0.5 M NaCl three times or against 50 mM TrisHCl (pH7.5)+0.1 M NaCl twice. SDS-PAGE analysis of the dialyzed protein indicates that the bFGF-CBD-CBD fusion protein was soluble in a physiological buffer at concentrations appropriate for purification and storage (FIG. 6). This result was surprising given that previous collagen-binding bFGF fusion proteins precipitated under these conditions. This improved solubility is attributed to the insertion of the MMP cleavage site. The protein concentration of the final pooled sample was measured using a BCA Protein Assay kit (ThermoFisher Scientific). The yield was 2.36 mg per liter of culture.

Figure 7:
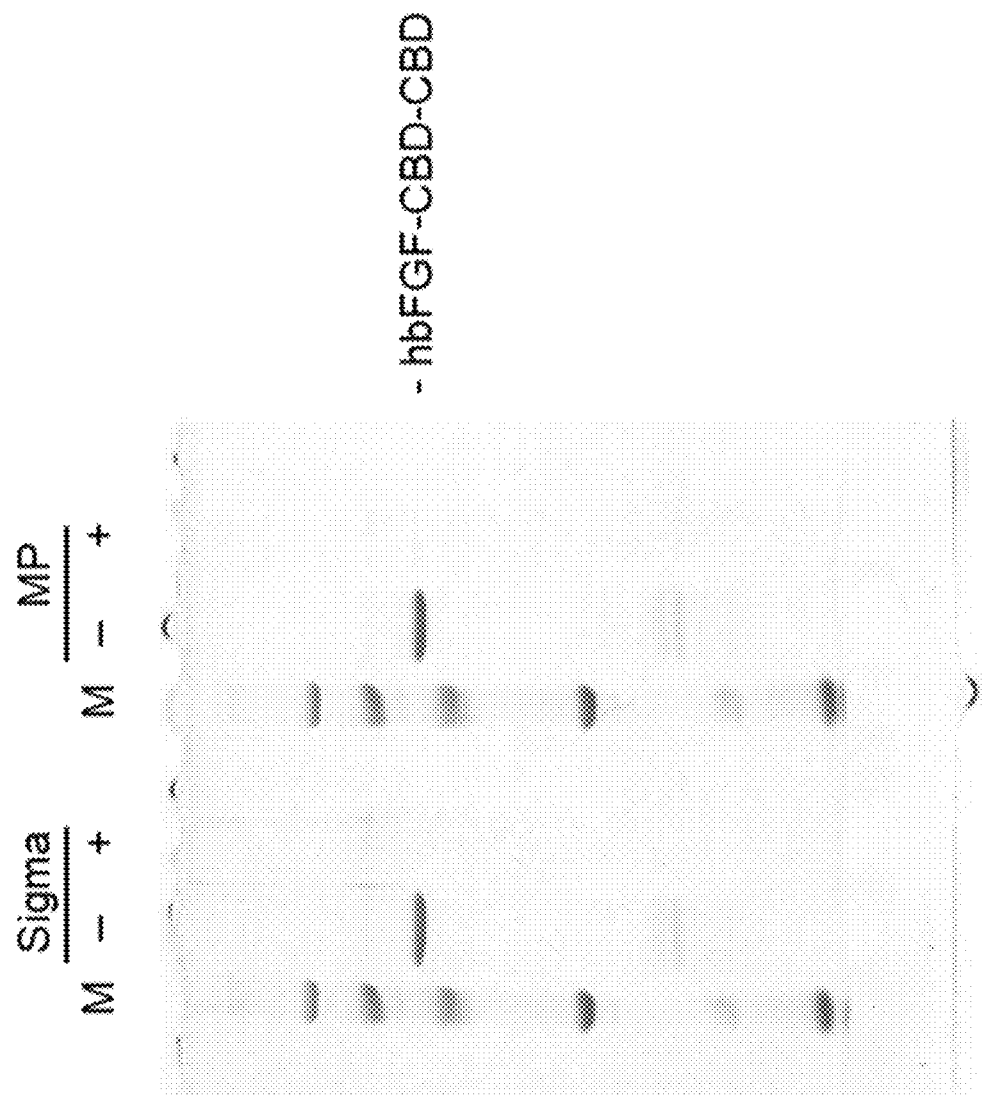
FIG. 7 is a Coomassie-stained 12.5% SDS-PAGE gel demonstrating the ability of the hbFGF-CBC-CBD fusion protein to bind to collagen. 200 pmol of hbFGF-CBC-CBD was dissolved in 100 µl of 50 mM TrisHCl (pH7.5), 0.1 M NaCl, 1 mM $CaCl_2$), and mixed with 10 mg of collagen powder prewashed in the same buffer. After incubation for 30 minutes at 4° C., 15 µl each of the unbound fractions were analyzed. M: 94, 67, 43, 30, 20.1, and 14.4 kDa markers. Sigma: Sigma collagen Type I (C-9879). MP: MP collagen (insoluble, Cat No 160083).

Finally, the ability of the purified bFGF-CBD-CBD fusion protein to bind to collagen was tested. 200 pmol of bFGF-CBC-CBD was dissolved in 100 µl of 50 mM TrisHCl (pH7.5), 0.1 M NaCl, 1 mM CaCl$_2$), and mixed with 10 mg of collagen powder prewashed in the same buffer. Two types of collagen were tested: Sigma collagen Type I (C-9879) and MP collagen (insoluble, Cat No 160083). After incubation for 30 minutes at 4° C., 15 µl each of the unbound fractions were analyzed by SDS-PAGE. The results of this analysis demonstrate that the purified bFGF-CBD-CBD fusion protein binds to collagen (FIG. 7).

What is claimed:

1. A collagen-binding agent comprising SEQ ID NO:1.

2. A pharmaceutical composition comprising the collagen-binding agent of claim 1 and a pharmaceutically acceptable carrier.

3. A method of treating a condition, the method comprising:
   administering the collagen-binding agent of claim 1 to a subject in an amount effective to treat the condition, wherein the condition is a wound.

4. The method of claim 3, wherein the subject is a mammal.

5. A biomedical device comprising a coating that comprises the collagen-binding agent of claim 1, wherein the biomedical device is a stent and wherein the coating further comprises a biodegradable polymer or a collagen.

6. A method of using the biomedical device of claim 5 to treat a condition, the method comprising: administering the device to a subject having the condition, wherein the condition is a wound.

* * * * *

SEQUENCE LISTING

<160> NUMBER OF SEQ ID NOS: 77

<210> SEQ ID NO 1
<211> LENGTH: 414
<212> TYPE: PRT
<213> ORGANISM: Artificial Sequence
<220> FEATURE:
<223> OTHER INFORMATION: Synthetic - FGF2-MMP1 cleavage site-tandem CBD fusion protein

<400> SEQUENCE: 1

```
Gly Ser Met Ala Ala Gly Ser Ile Thr Thr Leu Pro Ala Leu Pro Glu
1               5                   10                  15

Asp Gly Gly Ser Gly Ala Phe Pro Pro Gly His Phe Lys Asp Pro Lys
            20                  25                  30

Arg Leu Tyr Cys Lys Asn Gly Gly Phe Phe Leu Arg Ile His Pro Asp
        35                  40                  45

Gly Arg Val Asp Gly Val Arg Glu Lys Ser Asp Pro His Ile Lys Leu
    50                  55                  60

Gln Leu Gln Ala Glu Glu Arg Gly Val Val Ser Ile Lys Gly Val Cys
65                  70                  75                  80

Ala Asn Arg Tyr Leu Ala Met Lys Glu Asp Gly Arg Leu Leu Ala Ser
                85                  90                  95

Lys Cys Val Thr Asp Glu Cys Phe Phe Phe Glu Arg Leu Glu Ser Asn
            100                 105                 110

Asn Tyr Asn Thr Tyr Arg Ser Arg Lys Tyr Thr Ser Trp Tyr Val Ala
        115                 120                 125

Leu Lys Arg Thr Gly Gln Tyr Lys Leu Gly Ser Lys Thr Gly Pro Gly
    130                 135                 140

Gln Lys Ala Ile Leu Phe Leu Pro Met Ser Ala Lys Ser Gly Ile Ser
145                 150                 155                 160

Gly Gly Gly Ser Gly Pro Leu Gly Ile Ala Gly Pro Ser Gly Gly Gly
                165                 170                 175

Ser Gly Thr Thr Thr Pro Ile Thr Lys Glu Met Glu Pro Asn Asp Asp
            180                 185                 190

Ile Lys Glu Ala Asn Gly Pro Ile Val Glu Gly Val Thr Val Lys Gly
        195                 200                 205

Asp Leu Asn Gly Ser Asp Asp Ala Asp Thr Phe Tyr Phe Asp Val Lys
    210                 215                 220

Glu Asp Gly Asp Val Thr Ile Glu Leu Pro Tyr Ser Gly Ser Ser Asn
225                 230                 235                 240

Phe Thr Trp Leu Val Tyr Lys Glu Gly Asp Asp Gln Asn His Ile Ala
                245                 250                 255

Ser Gly Ile Asp Lys Asn Asn Ser Lys Val Gly Thr Phe Lys Ser Thr
            260                 265                 270

Lys Gly Arg His Tyr Val Phe Ile Tyr Lys His Asp Ser Ala Ser Asn
        275                 280                 285

Ile Ser Tyr Ser Leu Asn Ile Lys Gly Leu Gly Asn Glu Lys Leu Lys
    290                 295                 300

Glu Lys Glu Asn Asn Asp Ser Ser Asp Lys Ala Thr Val Ile Pro Asn
305                 310                 315                 320

Phe Asn Thr Thr Met Gln Gly Ser Leu Leu Gly Asp Asp Ser Arg Asp
                325                 330                 335

Tyr Tyr Ser Phe Glu Val Lys Glu Gly Glu Val Asn Ile Glu Leu
            340                 345                 350
```

```
Asp Lys Lys Asp Glu Phe Gly Val Thr Trp Thr Leu His Pro Glu Ser
            355                 360                 365

Asn Ile Asn Asp Arg Ile Thr Tyr Gly Gln Val Asp Gly Asn Lys Val
        370                 375                 380

Ser Asn Lys Val Lys Leu Arg Pro Gly Lys Tyr Tyr Leu Leu Val Tyr
385                 390                 395                 400

Lys Tyr Ser Gly Ser Gly Asn Tyr Glu Leu Arg Val Asn Lys
                405                 410

<210> SEQ ID NO 2
<211> LENGTH: 141
<212> TYPE: PRT
<213> ORGANISM: Homo sapiens
<220> FEATURE:
<221> NAME/KEY: MISC_FEATURE
<222> LOCATION: (1)..(141)
<223> OTHER INFORMATION: wild-type FGF1

<400> SEQUENCE: 2

Met Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140

<210> SEQ ID NO 3
<211> LENGTH: 141
<212> TYPE: PRT
<213> ORGANISM: Artificial Sequence
<220> FEATURE:
<223> OTHER INFORMATION: Synthetic - shFGF1

<400> SEQUENCE: 3

Met Phe Asn Leu Pro Pro Gly Asn Tyr Lys Lys Pro Lys Leu Leu Tyr
1               5                   10                  15

Cys Ser Asn Gly Gly His Phe Leu Arg Ile Leu Pro Asp Gly Thr Val
            20                  25                  30

Asp Gly Thr Arg Asp Arg Ser Asp Pro His Ile Gln Leu Gln Leu Leu
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn Ser Tyr Asn
                85                  90                  95
```

Thr Tyr Ile Ser Lys Lys His Ala Glu Lys Asn Trp Phe Val Gly Leu
            100                 105                 110

Asn Lys Asn Gly Ser Cys Lys Arg Gly Pro Glu Thr His Tyr Gly Gln
        115                 120                 125

Lys Ala Ile Leu Phe Leu Pro Leu Pro Val Ser Ser Asp
    130                 135                 140

<210> SEQ ID NO 4
<211> LENGTH: 155
<212> TYPE: PRT
<213> ORGANISM: Homo sapiens
<220> FEATURE:
<221> NAME/KEY: MISC_FEATURE
<222> LOCATION: (1)..(155)
<223> OTHER INFORMATION: wild-type FGF2

<400> SEQUENCE: 4

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155

<210> SEQ ID NO 5
<211> LENGTH: 155
<212> TYPE: PRT
<213> ORGANISM: Artificial Sequence
<220> FEATURE:
<223> OTHER INFORMATION: Synthetic - shFGF2

<400> SEQUENCE: 5

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Leu Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

```
Val Thr Asp Glu Cys Phe Phe Glu Arg Leu Glu Ser Asn Ser Tyr
            100                 105                 110

Asn Thr Tyr Arg Ser Arg Lys Tyr Thr Ser Trp Tyr Val Ala Leu Asn
        115                 120                 125

Arg Thr Gly Gln Tyr Lys Leu Gly Ser Glu Thr Gly Pro Gly Gln Lys
        130                 135                 140

Ala Ile Leu Phe Leu Pro Met Ser Ala Lys Ser
145                 150                 155

<210> SEQ ID NO 6
<211> LENGTH: 113
<212> TYPE: PRT
<213> ORGANISM: Clostridium histolyticum
<220> FEATURE:
<221> NAME/KEY: MISC_FEATURE
<222> LOCATION: (1)..(113)
<223> OTHER INFORMATION: ColG s3a domain

<400> SEQUENCE: 6

Thr Lys Glu Met Glu Pro Asn Asp Asp Ile Lys Glu Ala Asn Gly Pro
1               5                   10                  15

Ile Val Glu Gly Val Thr Val Lys Gly Asp Leu Asn Gly Ser Asp Asp
            20                  25                  30

Ala Asp Thr Phe Tyr Phe Asp Val Lys Glu Asp Gly Asp Val Thr Ile
        35                  40                  45

Glu Leu Pro Tyr Ser Gly Ser Ser Asn Phe Thr Trp Leu Val Tyr Lys
    50                  55                  60

Glu Gly Asp Asp Gln Asn His Ile Ala Ser Gly Ile Asp Lys Asn Asn
65                  70                  75                  80

Ser Lys Val Gly Thr Phe Lys Ser Thr Lys Gly Arg His Tyr Val Phe
                85                  90                  95

Ile Tyr Lys His Asp Ser Ala Ser Asn Ile Ser Tyr Ser Leu Asn Ile
            100                 105                 110

Lys

<210> SEQ ID NO 7
<211> LENGTH: 111
<212> TYPE: PRT
<213> ORGANISM: Brevibacillus brevis
<220> FEATURE:
<221> NAME/KEY: MISC_FEATURE
<222> LOCATION: (1)..(111)
<223> OTHER INFORMATION: ColG s3a domain

<400> SEQUENCE: 7

Glu Lys Glu Gln Glu Pro Asn Asn Ser Phe Ser Glu Ala Asn Pro Leu
1               5                   10                  15

Lys Ser Asn Val Glu Leu Ser Gly Gln Thr Ser Lys Gln Asp Asp Lys
            20                  25                  30

Asp Ile Phe Ala Leu Lys Val Leu Gly Asn Gly Thr Val Lys Ile Asn
        35                  40                  45

Val Thr Ser Glu His Asp Thr Gly Leu Asn Trp Val Val His His Glu
    50                  55                  60

Asp Asp Leu Asn Asn Tyr Leu Ala Tyr Pro Lys Thr Ser Gly Lys Thr
65                  70                  75                  80

Leu Ser Gly Glu Phe Glu Ala Thr Pro Gly Thr Tyr Tyr Leu Ser Val
                85                  90                  95

Tyr Asn Phe Asn Gly Glu Thr Ile Pro Tyr Lys Val Thr Ala Glu
            100                 105                 110
```

<210> SEQ ID NO 8
<211> LENGTH: 115
<212> TYPE: PRT
<213> ORGANISM: Clostridium sporogenes
<220> FEATURE:
<221> NAME/KEY: MISC_FEATURE
<222> LOCATION: (1)..(115)
<223> OTHER INFORMATION: ColG s3a domain

<400> SEQUENCE: 8

```
Val Ser Glu Lys Glu Asp Asn Asn Asp Phe Thr Thr Ala Asn Pro Val
1               5                   10                  15

Tyr Tyr Lys Asp Leu Val Asn Gly Ser Val Ser Ser Asp Asn Lys
            20                  25                  30

Asp Thr Phe Tyr Phe Thr Val Thr Lys Pro Ser Asp Ile Thr Ile Thr
            35                  40                  45

Val Glu Lys Thr Asn Asn Asp Lys Ser Glu Phe Asn Trp Leu Leu Phe
50                  55                  60

Ser Asp Glu Asp Lys Ser Asn Tyr Met Ala Phe Pro Asn Lys Glu Leu
65                  70                  75                  80

Gly Asn Gln Leu Ser Asn Thr Val Lys Ile Asn Lys Pro Gly Lys Tyr
                85                  90                  95

Tyr Leu Val Ile Tyr Lys Thr Leu Gly Glu Lys Val Asp Tyr Lys Phe
                100                 105                 110

Ser Ile Glu
        115
```

<210> SEQ ID NO 9
<211> LENGTH: 115
<212> TYPE: PRT
<213> ORGANISM: Clostridium botulinum
<220> FEATURE:
<221> NAME/KEY: MISC_FEATURE
<222> LOCATION: (1)..(115)
<223> OTHER INFORMATION: ColG s3a domain from subtype A3

<400> SEQUENCE: 9

```
Val Ser Glu Lys Glu Asn Asn Asn Asp Tyr Val Asn Ala Asn Pro Val
1               5                   10                  15

Tyr Ser Lys Asp Leu Val Asn Gly Ser Val Ser Ser Asp Asp Arg
            20                  25                  30

Asp Ile Phe Tyr Phe Asn Val Thr Lys Pro Ser Asp Ile Thr Ile Asn
            35                  40                  45

Val Glu Lys Ile Asn Lys Asp Lys Ser Glu Phe Ser Trp Leu Leu Phe
50                  55                  60

Ser Glu Glu Asp Lys Ser Asn Tyr Ile Thr Tyr Pro Asn Lys Glu Leu
65                  70                  75                  80

Glu Asn Leu Phe Tyr Ser Thr Val Lys Ile Asp Lys Pro Gly Lys Tyr
                85                  90                  95

Tyr Leu Val Ile Tyr Lys Val Ser Gly Glu Lys Ser Asp Tyr Arg Phe
                100                 105                 110

Asn Ile Glu
        115
```

<210> SEQ ID NO 10
<211> LENGTH: 113
<212> TYPE: PRT
<213> ORGANISM: Clostridium perfringens
<220> FEATURE:

```
<221> NAME/KEY: MISC_FEATURE
<222> LOCATION: (1)..(113)
<223> OTHER INFORMATION: ColG s3a domain

<400> SEQUENCE: 10
```

Ile Asn Glu Ser Glu Pro Asn Asn Asp Phe Glu Lys Ala Asn Gln Ile
1               5                   10                  15

Ala Lys Ser Asn Met Leu Val Lys Gly Thr Leu Ser Glu Glu Asp Tyr
            20                  25                  30

Ser Asp Lys Tyr Tyr Phe Asp Val Ala Lys Lys Gly Asn Val Lys Ile
        35                  40                  45

Thr Leu Asn Asn Leu Asn Ser Val Gly Ile Thr Trp Thr Leu Tyr Lys
50                  55                  60

Glu Gly Asp Leu Asn Asn Tyr Val Leu Tyr Ala Thr Gly Asn Glu Gly
65                  70                  75                  80

Thr Val Leu Lys Gly Glu Lys Thr Leu Glu Pro Gly Arg Tyr Tyr Leu
                85                  90                  95

Ser Val Tyr Thr Tyr Asp Asn Gln Ser Gly Ala Tyr Thr Val Asn Val
            100                 105                 110

Lys

```
<210> SEQ ID NO 11
<211> LENGTH: 113
<212> TYPE: PRT
<213> ORGANISM: Clostridium sordellii
<220> FEATURE:
<221> NAME/KEY: MISC_FEATURE
<222> LOCATION: (1)..(113)
<223> OTHER INFORMATION: ColG s3a domain

<400> SEQUENCE: 11
```

Ser Gln Glu Val Gly Asn Asp Asp Thr Phe Glu Thr Ala Asn Gly Pro
1               5                   10                  15

Ile Lys Ile Asn Thr Asn Tyr Ser Gly Asp Leu Ser Asp Thr Asp Asn
            20                  25                  30

Lys Asp Tyr Tyr Tyr Phe Asn Leu Asp Asn Pro Ser Asn Ile Asn Ile
        35                  40                  45

Thr Leu Glu Asn Leu Asp Asn Lys Gly Ile Ser Trp Gln Leu Phe His
50                  55                  60

Glu Ser Asp Leu Asn Asn Tyr Val Ala Tyr Pro Thr Thr Ser Gly Ala
65                  70                  75                  80

Ile Leu Asn Gly Asp Tyr Asn Ala Thr Lys Pro Gly Lys Tyr Tyr Ile
                85                  90                  95

Leu Val Tyr Asn His Asp Lys Ser Ile Ala Asn Tyr Asn Leu Lys Val
            100                 105                 110

Asn

```
<210> SEQ ID NO 12
<211> LENGTH: 116
<212> TYPE: PRT
<213> ORGANISM: Clostridium histolyticum
<220> FEATURE:
<221> NAME/KEY: MISC_FEATURE
<222> LOCATION: (1)..(116)
<223> OTHER INFORMATION: ColG s3a domain

<400> SEQUENCE: 12
```

Thr Pro Ile Thr Lys Glu Met Glu Pro Asn Asp Asp Ile Lys Glu Ala
1               5                   10                  15

Asn Gly Pro Ile Val Glu Gly Val Thr Val Lys Gly Asp Leu Asn Gly
            20                  25                  30

Ser Asp Asp Ala Asp Thr Phe Tyr Phe Asp Val Lys Glu Asp Gly Asp
        35                  40                  45

Val Thr Ile Glu Leu Pro Tyr Ser Gly Ser Ser Asn Phe Thr Trp Leu
 50                  55                  60

Val Tyr Lys Glu Gly Asp Asp Gln Asn His Ile Ala Ser Gly Ile Asp
 65                  70                  75                  80

Lys Asn Asn Ser Lys Val Gly Thr Phe Lys Ser Thr Lys Gly Arg His
                85                  90                  95

Tyr Val Phe Ile Tyr Lys His Asp Ser Ala Ser Asn Ile Ser Tyr Ser
            100                 105                 110

Leu Asn Ile Lys
        115

<210> SEQ ID NO 13
<211> LENGTH: 117
<212> TYPE: PRT
<213> ORGANISM: Clostridium sporogenes
<220> FEATURE:
<221> NAME/KEY: MISC_FEATURE
<222> LOCATION: (1)..(117)
<223> OTHER INFORMATION: ColG s3a domain

<400> SEQUENCE: 13

Leu Val Ile Ser Glu Lys Glu Asp Asn Asp Ser Phe Asp Lys Ala Asn
 1               5                  10                  15

Arg Val Cys Lys Asn Gln Ser Val Leu Ala Thr Leu Asp Thr Asn Asp
            20                  25                  30

Asn Arg Asp Thr Tyr Tyr Phe Asp Ala Leu Thr Ala Gly Thr Ile Asp
        35                  40                  45

Val Ile Met Glu Asn Thr Asp Asn Ser Asn Ile Phe Asn Trp Leu
 50                  55                  60

Ala Tyr Ser Ser Asp Asn Thr Asn Asn Tyr Ile Gly Tyr Ser Thr Lys
 65                  70                  75                  80

Lys Glu Gly Asn Lys Leu Leu Gly Ser Phe Lys Val Pro Lys Pro Gly
                85                  90                  95

Arg Tyr Tyr Ile Leu Ala Tyr Lys Asn Ser Ser Asn Lys Ile Asn Tyr
            100                 105                 110

Lys Leu Thr Ile Asn
        115

<210> SEQ ID NO 14
<211> LENGTH: 117
<212> TYPE: PRT
<213> ORGANISM: Clostridium botulinum
<220> FEATURE:
<221> NAME/KEY: MISC_FEATURE
<222> LOCATION: (1)..(117)
<223> OTHER INFORMATION: ColG s3a domain from type B

<400> SEQUENCE: 14

Ile Asn Val Asp Glu Glu Glu Tyr Asn Asp Asp Phe Glu Cys Ala Asn
 1               5                  10                  15

Asn Ile Phe Lys Asn Gln Ile Met Ser Gly Asn Leu Asp Ser Ser Asp
            20                  25                  30

Lys Cys Asp Thr Phe Ser Phe Asn Ala Leu Ser Ala Gly Thr Ile Asn
        35                  40                  45

Val Thr Leu Glu Asn Ser Asn Ser Asp Ser Ser Thr Val Asn Trp Leu 50                  55                  60
Ala Tyr Ser Ser Glu Asp Thr Asp Asn Tyr Ile Gly Tyr Ala Ser Glu
 65                  70                  75                  80

Asn Asp Gly Asn Lys Phe Ser Gly Lys Phe Lys Val Asn Lys Pro Gly
                 85                  90                  95

Lys Tyr Tyr Ile Val Ala Tyr Glu Val Asn Gly Ala Asp Ser Lys Tyr
            100                 105                 110

Lys Leu Lys Val Asp
        115

<210> SEQ ID NO 15
<211> LENGTH: 117
<212> TYPE: PRT
<213> ORGANISM: Clostridium tetani
<220> FEATURE:
<221> NAME/KEY: MISC_FEATURE
<222> LOCATION: (1)..(117)
<223> OTHER INFORMATION: ColG s3a domain from strain E88

<400> SEQUENCE: 15

Asn Val Ile Tyr Glu Lys Glu Asn Asn Asp Ser Phe Asp Lys Ala Asn
1                5                  10                  15

Lys Ile His Lys Asn Gln Ile Val Met Ala Thr Leu Asp Thr Glu Asp
                20                  25                  30

Tyr Arg Asp Thr Phe Tyr Phe Asp Ala Leu Thr Ser Gly Ser Ile Asp
            35                  40                  45

Ile Thr Ile Glu Asn Ile His Gly Asn Ser Asp Ala Phe Asn Trp Leu
        50                  55                  60

Val Tyr Asn Asp Glu Asp Leu Asn Asn Tyr Ile Ala Tyr Pro Thr Lys
 65                  70                  75                  80

Lys Glu Asp Asn Lys Leu Met Gly Ser Phe Lys Val His Lys Pro Gly
                 85                  90                  95

Arg Tyr Tyr Ile Leu Val Tyr Lys Thr Ser Leu Asn Lys Val Asn Tyr
            100                 105                 110

Lys Leu Asn Ile Ser
        115

<210> SEQ ID NO 16
<211> LENGTH: 115
<212> TYPE: PRT
<213> ORGANISM: Clostridium perfringens
<220> FEATURE:
<221> NAME/KEY: MISC_FEATURE
<222> LOCATION: (1)..(115)
<223> OTHER INFORMATION: ColG s3a domain

<400> SEQUENCE: 16

Glu Val Ile Asn Glu Ser Glu Pro Asn Asn Asp Phe Glu Lys Ala Asn
1                5                  10                  15

Gln Ile Ala Lys Ser Asn Met Leu Val Lys Gly Thr Leu Ser Glu Glu
                20                  25                  30

Asp Tyr Ser Asp Lys Tyr Tyr Phe Asp Val Ala Lys Lys Gly Asn Val
            35                  40                  45

Lys Ile Thr Leu Asn Asn Leu Asn Ser Val Gly Ile Thr Trp Thr Leu
        50                  55                  60

Tyr Lys Glu Gly Asp Leu Asn Asn Tyr Val Leu Tyr Ala Thr Gly Asn
 65                  70                  75                  80

Asp Gly Thr Val Leu Lys Gly Glu Lys Thr Leu Glu Pro Gly Arg Tyr
                 85                  90                  95

```
Tyr Leu Ser Val Tyr Thr Tyr Asp Asn Gln Ser Gly Thr Tyr Thr Val
            100                 105                 110

Asn Val Lys
        115

<210> SEQ ID NO 17
<211> LENGTH: 115
<212> TYPE: PRT
<213> ORGANISM: Brevibacillus brevis
<220> FEATURE:
<221> NAME/KEY: MISC_FEATURE
<222> LOCATION: (1)..(115)
<223> OTHER INFORMATION: ColG s3a domain

<400> SEQUENCE: 17

Asp Gly Ser Glu Thr Glu Gln Pro Asn Pro Asn Pro Glu Glu Ser Ser
1               5                   10                  15

Leu Ser Leu Gly Lys Pro Ile Thr Gly Ile Ile His Pro Gln Lys Pro
                20                  25                  30

Ser Gln Glu Phe Arg Leu Asp Val Lys Ser Ala Gln Gln Leu Gln Val
            35                  40                  45

Glu Met Glu Thr Lys Gln Gly Asp Gly Val Ala Trp Leu Val Phe His
    50                  55                  60

Glu Ala Asp Arg Glu Asn Tyr Ile Ser Tyr Pro Thr Lys Arg Glu Gly
65                  70                  75                  80

Asn Lys Leu Ile Gly Ser Phe Asp Ala Lys Pro Gly Thr Tyr Tyr Val
                85                  90                  95

Thr Ala Tyr Thr Tyr Arg Thr Glu Gln Glu Asp Gln Pro Phe Arg Leu
            100                 105                 110

Leu Val Thr
        115

<210> SEQ ID NO 18
<211> LENGTH: 114
<212> TYPE: PRT
<213> ORGANISM: Paenibacillus dendritiformis
<220> FEATURE:
<221> NAME/KEY: MISC_FEATURE
<222> LOCATION: (1)..(114)
<223> OTHER INFORMATION: ColG s3a domain

<400> SEQUENCE: 18

Pro Asn Ala Asp His Glu Pro Asn Asp Ser Trp Glu Gln Ala Val Pro
1               5                   10                  15

Leu Asp Gly Thr Gly Val Pro Val Ser Gly Lys Leu Ser Asp Thr Asp
                20                  25                  30

Arg Val Asp Val Tyr Arg Phe Asp Ala Gly Lys Ala Glu Gln Trp Thr
            35                  40                  45

Ile Glu Leu Glu Thr Glu Gln Ala Gln Ser Val Ala Trp Val Val His
    50                  55                  60

His Glu Ser Asp Leu Asn Asn Tyr Ala Ala Tyr Pro Thr Gln Val Glu
65                  70                  75                  80

Gly Thr Ser Val Ala Gly Ser Val Asp Ala Val Pro Gly Thr Tyr Tyr
                85                  90                  95

Val Tyr Val Tyr Ser Val Gly Asn Gly Glu Gln Ser Tyr Arg Leu Val
            100                 105                 110

Val Gln
```

```
<210> SEQ ID NO 19
<211> LENGTH: 116
<212> TYPE: PRT
<213> ORGANISM: Clostridium sordellii
<220> FEATURE:
<221> NAME/KEY: MISC_FEATURE
<222> LOCATION: (1)..(116)
<223> OTHER INFORMATION: ColG s3a domain

<400> SEQUENCE: 19
```

Pro Lys Gly Ser Gln Glu Val Gly Asn Asp Asp Thr Phe Glu Thr Ala
1               5                   10                  15

Asn Gly Pro Ile Lys Ile Asn Thr Asn Tyr Ser Gly Asp Leu Ser Asp
            20                  25                  30

Thr Asp Asn Lys Asp Tyr Tyr Phe Asn Leu Asp Asn Pro Ser Asn
        35                  40                  45

Ile Asn Ile Thr Leu Gly Asn Leu Asp Asn Lys Gly Ile Ser Trp Gln
    50                  55                  60

Leu Phe His Glu Ser Asp Leu Asn Asn Tyr Val Ala Tyr Pro Thr Thr
65                  70                  75                  80

Ser Gly Ala Ile Leu Asn Gly Asp Tyr Asn Ala Thr Lys Pro Gly Lys
                85                  90                  95

Tyr Tyr Ile Leu Val Tyr Asn His Asp Lys Ser Ile Ala Asn Tyr Asn
            100                 105                 110

Leu Lys Val Asn
        115

```
<210> SEQ ID NO 20
<211> LENGTH: 111
<212> TYPE: PRT
<213> ORGANISM: Clostridium histolyticum
<220> FEATURE:
<221> NAME/KEY: MISC_FEATURE
<222> LOCATION: (1)..(111)
<223> OTHER INFORMATION: ColG s3b domain

<400> SEQUENCE: 20
```

Leu Lys Glu Lys Glu Asn Asn Asp Ser Ser Asp Lys Ala Thr Val Ile
1               5                   10                  15

Pro Asn Phe Asn Thr Thr Met Gln Gly Ser Leu Leu Gly Asp Asp Ser
            20                  25                  30

Arg Asp Tyr Tyr Ser Phe Glu Val Lys Glu Glu Gly Glu Val Asn Ile
            35                  40                  45

Glu Leu Asp Lys Lys Asp Glu Phe Gly Val Thr Trp Thr Leu His Pro
    50                  55                  60

Glu Ser Asn Ile Asn Asp Arg Ile Thr Tyr Gly Gln Val Asp Gly Asn
65                  70                  75                  80

Lys Val Ser Asn Lys Val Lys Leu Arg Pro Gly Lys Tyr Tyr Leu Leu
                85                  90                  95

Val Tyr Lys Tyr Ser Gly Ser Gly Asn Tyr Glu Leu Arg Val Asn
            100                 105                 110

```
<210> SEQ ID NO 21
<211> LENGTH: 111
<212> TYPE: PRT
<213> ORGANISM: Bacillus sp.
<220> FEATURE:
<221> NAME/KEY: MISC_FEATURE
<222> LOCATION: (1)..(111)
<223> OTHER INFORMATION: ColG s3b domain

<400> SEQUENCE: 21
```

Lys Thr Glu Ile Glu Pro Asn Arg Pro Glu Ala Thr Met Leu
1               5                   10                  15

Pro Phe Asn Thr Pro Leu Ser Gly Ser Leu Met Glu Asp His Thr
            20                  25                  30

Asp Val Tyr Glu Phe Asn Val Thr Ser Pro Lys Glu Ile Asp Ile Ser
        35                  40                  45

Val Leu Asn Glu Asn Gln Ile Gly Met Thr Trp Val Leu Tyr His Glu
    50                  55                  60

Ser Asp Ser Gln Asn Tyr Ala Ser Phe Gly Gln Asp Gly Asn Met
65                  70                  75                  80

Ile Asn Gly Lys Trp Asn Ala Lys Pro Gly Lys Tyr Tyr Leu Tyr Val
                85                  90                  95

Tyr Lys Phe Glu Asn Glu Asn Gly Thr Tyr Thr Val His Val Gln
            100                 105                 110

<210> SEQ ID NO 22
<211> LENGTH: 111
<212> TYPE: PRT
<213> ORGANISM: Lysinibacillus sphaericus
<220> FEATURE:
<221> NAME/KEY: MISC_FEATURE
<222> LOCATION: (1)..(111)
<223> OTHER INFORMATION: ColG s3b domain

<400> SEQUENCE: 22

Lys Ala Glu Ile Glu Pro Asn Arg Pro Glu Ala Thr Ile Leu
1               5                   10                  15

Pro Phe Asn Thr Pro Leu Lys Gly Arg Leu Met Asp Asp His Thr
            20                  25                  30

Asp Val Tyr Glu Phe Asn Val Thr Ser Pro Lys Glu Leu Asp Ile Ser
        35                  40                  45

Val Leu Asn Glu Asn Arg Ile Gly Met Thr Trp Val Leu Tyr His Glu
    50                  55                  60

Ser Asp Ser Gln Asn Tyr Ala Ser Phe Gly Gln Glu Gly Asn Met
65                  70                  75                  80

Ile Asn Gly Lys Leu His Ala Gly Pro Gly Lys Tyr Tyr Leu Tyr Val
                85                  90                  95

Tyr Lys Phe Glu Asn Glu Asn Gly Thr Tyr Thr Val Gln Val Gln
            100                 105                 110

<210> SEQ ID NO 23
<211> LENGTH: 111
<212> TYPE: PRT
<213> ORGANISM: Brevibacillus brevis
<220> FEATURE:
<221> NAME/KEY: MISC_FEATURE
<222> LOCATION: (1)..(111)
<223> OTHER INFORMATION: ColG s3b domain

<400> SEQUENCE: 23

Pro Thr Glu Val Glu Pro Asn Asn Ser Phe Asp Asp Ala Asn Thr Leu
1               5                   10                  15

Gln Leu Gly Lys Glu Ile Ser Gly Gln Thr Asp Arg Thr Asp Asp Lys
            20                  25                  30

Asp Thr Tyr Met Ile Gln Val Glu Glu Gly Val Ile Gln Val Thr
        35                  40                  45

Val Ser Ser Glu Lys Asp Glu Gly Leu Asn Trp Val Val Phe His Glu
    50                  55                  60

Asp Asp Leu Lys Thr Tyr Phe Ala Tyr Pro Lys Thr Gly Lys Lys
65                  70                  75                  80

Leu Thr Gly Glu Phe Glu Ala Lys Pro Gly Lys Tyr Tyr Leu Leu Val
                85                  90                  95

Tyr Asn Thr Asn Asn Thr Lys Ile Pro Tyr Lys Ala Ile Val Asn
            100                 105                 110

<210> SEQ ID NO 24
<211> LENGTH: 112
<212> TYPE: PRT
<213> ORGANISM: Clostridium perfringens
<220> FEATURE:
<221> NAME/KEY: MISC_FEATURE
<222> LOCATION: (1)..(112)
<223> OTHER INFORMATION: ColG s3b domain

<400> SEQUENCE: 24

Ile Lys Glu Val Glu Asn Asn Asp Phe Asp Lys Ala Met Lys Val
1               5                   10                  15

Asp Ser Asn Ser Lys Ile Val Gly Thr Leu Ser Asn Asp Leu Lys
            20                  25                  30

Asp Ile Tyr Ser Ile Asp Ile Lys Asn Pro Ser Asp Leu Asn Ile Val
            35                  40                  45

Val Glu Asn Leu Asp Asn Ile Lys Met Asn Trp Leu Leu Tyr Ser Ala
50                  55                  60

Asp Asp Leu Ser Asn Tyr Val Asp Tyr Ala Asn Ala Asp Gly Asn Lys
65                  70                  75                  80

Leu Ser Asn Thr Cys Lys Leu Asn Pro Gly Lys Tyr Tyr Leu Cys Val
                85                  90                  95

Tyr Gln Phe Glu Asn Ser Gly Thr Gly Asn Tyr Thr Val Asn Leu Gln
            100                 105                 110

<210> SEQ ID NO 25
<211> LENGTH: 115
<212> TYPE: PRT
<213> ORGANISM: Clostridium sporogenes
<220> FEATURE:
<221> NAME/KEY: MISC_FEATURE
<222> LOCATION: (1)..(115)
<223> OTHER INFORMATION: ColG s3b domain

<400> SEQUENCE: 25

Ile Ser Glu Lys Glu Asp Asn Asp Ser Phe Asp Lys Ala Asn Arg Val
1               5                   10                  15

Gly Lys Asn Gln Thr Val Leu Ala Thr Leu Asp Thr Lys Asp Asn Arg
            20                  25                  30

Asp Thr Tyr Tyr Phe Asp Ala Leu Ala Ala Arg Thr Ile Asp Ile Val
            35                  40                  45

Met Glu Asn Thr Asp Asn Asn Ser Thr Ile Phe Asn Trp Leu Ala Tyr
50                  55                  60

Ser Ser Asp Asn Thr Asn Asn Tyr Ile Gly Tyr Pro Thr Lys Lys Glu
65                  70                  75                  80

Gly Asn Lys Leu Met Gly Ser Phe Lys Val Pro Lys Pro Gly Arg Tyr
                85                  90                  95

Tyr Ile Leu Ala Tyr Lys Asn Ser Ser Asn Lys Ile Asn Tyr Lys Leu
            100                 105                 110

Thr Ile Asn
        115

<210> SEQ ID NO 26
<211> LENGTH: 115
<212> TYPE: PRT
<213> ORGANISM: Clostridium botulinum
<220> FEATURE:
<221> NAME/KEY: MISC_FEATURE
<222> LOCATION: (1)..(115)
<223> OTHER INFORMATION: ColG s3b domain from strain A3

<400> SEQUENCE: 26

Ile Ser Glu Lys Glu Asp Asn Asn Ser Phe Asp Lys Ala Asn Arg Val
1               5                   10                  15

Cys Lys Asn Gln Ser Val Ile Ala Thr Leu Asp Thr Asn Asp Pro Arg
            20                  25                  30

Asp Thr Tyr Tyr Phe Asp Ala Leu Thr Ala Gly Asn Ile Glu Val Thr
        35                  40                  45

Met Gly Asn Thr Asp Asn Ser Ser Asn Glu Phe Asn Trp Leu Ala Tyr
    50                  55                  60

Ser Ser Asp Asn Thr Asn Asn Tyr Ile Gly Tyr Ala Thr Lys Arg Glu
65                  70                  75                  80

Gly Asn Lys Ile Thr Gly Asn Phe Lys Val Asp Lys Pro Gly Arg Tyr
                85                  90                  95

Tyr Ile Val Ala Tyr Lys Thr Ser Ser Asn Lys Ile Asn Tyr Lys Leu
            100                 105                 110

Asn Ile Lys
        115

<210> SEQ ID NO 27
<211> LENGTH: 113
<212> TYPE: PRT
<213> ORGANISM: Clostridium sordellii
<220> FEATURE:
<221> NAME/KEY: MISC_FEATURE
<222> LOCATION: (1)..(113)
<223> OTHER INFORMATION: ColG s3b domain

<400> SEQUENCE: 27

Gly Val Glu Gln Glu Asp Asn Asn Ser Phe Glu Lys Ala Asn Pro Phe
1               5                   10                  15

Ser Ile Asn Gln Leu Val Lys Gly Glu Leu Asp Asn Asn Lys Asp Thr
            20                  25                  30

Ser Asp Tyr Phe Lys Phe Glu Val Lys Glu Asp Ala Gln Leu Asn Ile
        35                  40                  45

Ser Leu Glu Lys Thr Glu Gly Asp Gly Val Asn Trp Leu Leu Phe Lys
    50                  55                  60

Asp Ser Asp Leu Glu Asn Tyr Ile Ala Ser Pro Thr Glu Ser Ile Asp
65                  70                  75                  80

Asn Lys Leu Asn Gly Lys Val Asp Leu Lys Val Gly Thr Tyr Tyr Leu
                85                  90                  95

Glu Val Tyr Gly Tyr Gly Ser Ser Pro Val Lys Tyr Asn Phe Lys Val
            100                 105                 110

Thr

<210> SEQ ID NO 28
<211> LENGTH: 112
<212> TYPE: PRT
<213> ORGANISM: Clostridium histolyticum
<220> FEATURE:
<221> NAME/KEY: MISC_FEATURE
<222> LOCATION: (1)..(112)
<223> OTHER INFORMATION: ColG s3b domain -continued

<400> SEQUENCE: 28

Leu Lys Glu Lys Glu Asn Asn Asp Ser Ser Asp Lys Ala Thr Val Ile
1               5                   10                  15

Pro Asn Phe Asn Thr Thr Met Gln Gly Ser Leu Leu Gly Asp Asp Ser
            20                  25                  30

Arg Asp Tyr Tyr Ser Phe Glu Val Lys Glu Glu Gly Glu Val Asn Ile
        35                  40                  45

Glu Leu Asp Lys Lys Asp Glu Phe Gly Val Thr Trp Thr Leu His Pro
50                  55                  60

Glu Ser Asn Ile Asn Asp Arg Ile Thr Tyr Gly Gln Val Asp Gly Asn
65                  70                  75                  80

Lys Val Ser Asn Lys Val Lys Leu Arg Pro Gly Lys Tyr Tyr Leu Leu
                85                  90                  95

Val Tyr Lys Tyr Ser Gly Ser Gly Asn Tyr Glu Leu Arg Val Asn Lys
            100                 105                 110

<210> SEQ ID NO 29
<211> LENGTH: 111
<212> TYPE: PRT
<213> ORGANISM: Clostridium sporogenes
<220> FEATURE:
<221> NAME/KEY: MISC_FEATURE
<222> LOCATION: (1)..(111)
<223> OTHER INFORMATION: ColG s3b domain

<400> SEQUENCE: 29

Ile His Glu Lys Glu Asn Asn Asp Ser Phe Glu Ser Ala Asn Lys Ile
1               5                   10                  15

Val Pro Asp Ala Pro Val Leu Gly Ser Leu Asn Gly Glu Asp Leu Arg
            20                  25                  30

Asp Ile Tyr Ser Phe Asp Ile Lys Glu Thr Lys Asp Leu Asn Ile Lys
        35                  40                  45

Leu Thr Asn Leu Asn Asn Leu Gly Leu Thr Trp Thr Leu Tyr Lys Glu
50                  55                  60

Ser Asp Leu Thr Asn Tyr Ile Ala Tyr Gly Ser Lys Leu Gly Asn Thr
65                  70                  75                  80

Ile Val Gly Asn Cys His Val Thr Pro Gly Lys Tyr Tyr Leu Tyr Val
            85                  90                  95

Tyr Lys Tyr Ser Gly Asn Ser Gly Asn Tyr Ser Leu Ile Ile Lys
            100                 105                 110

<210> SEQ ID NO 30
<211> LENGTH: 111
<212> TYPE: PRT
<213> ORGANISM: Clostridium botulinum
<220> FEATURE:
<221> NAME/KEY: MISC_FEATURE
<222> LOCATION: (1)..(111)
<223> OTHER INFORMATION: ColG s3b domain from type B

<400> SEQUENCE: 30

Ile Lys Glu Glu Ile Asn Asp Asp Ser Phe Asp Ser Ala Thr Lys Ile
1               5                   10                  15

Lys Ala Asn Ser Thr Ile Thr Asp Thr Leu Asn Gly Glu Asp Asn Lys
            20                  25                  30

Asp Ile Cys Tyr Phe Asn Val Asn Asn Ser Asp Leu Asn Ile Glu
        35                  40                  45

Leu Asn Ser Leu Thr Asn Leu Gly Val Ala Trp Gln Leu Phe Ser Glu

```
                    50                  55                  60
Glu Asp Leu Asp Asn Tyr Ile Ala Tyr Gly Ser Gln Ser Gly Asp Ser
 65                  70                  75                  80

Ile Val Gly Thr Ala Asn Val Gln Pro Gly Lys Tyr Tyr Leu Leu Ile
                     85                  90                  95

Tyr Lys Tyr Thr Gln Ala Asp Gly Ser Tyr Thr Phe Thr Ile Lys
                100                 105                 110

<210> SEQ ID NO 31
<211> LENGTH: 111
<212> TYPE: PRT
<213> ORGANISM: Clostridium tetani
<220> FEATURE:
<221> NAME/KEY: MISC_FEATURE
<222> LOCATION: (1)..(111)
<223> OTHER INFORMATION: ColG s3b domain from strain E88

<400> SEQUENCE: 31

Ile His Glu Lys Glu Asn Asn Asp Ser Phe Glu Thr Ala Asn Lys Ile
 1               5                  10                  15

Thr Leu Asp Thr Leu Val Leu Gly Asn Leu Asp Tyr Lys Asp Val Ser
                 20                  25                  30

Asp Ile Tyr Ser Phe Asp Ile Glu Asn Thr Lys Asp Leu Asn Ile Lys
             35                  40                  45

Leu Thr Asn Leu Asn Asn Leu Gly Ile Ala Trp Asn Leu Tyr Lys Glu
 50                  55                  60

Ser Asp Leu Asn Asn Tyr Ile Ala Tyr Gly Ala Lys Ser Asp Asn Ala
 65                  70                  75                  80

Ile Val Gly Lys Cys Asn Leu Ser Pro Gly Lys Tyr Tyr Leu Tyr Val
                 85                  90                  95

Tyr Lys Tyr Ser Gly Asp Lys Gly Asn Tyr Ser Val Ile Ile Asn
                100                 105                 110

<210> SEQ ID NO 32
<211> LENGTH: 114
<212> TYPE: PRT
<213> ORGANISM: Clostridium perfringens
<220> FEATURE:
<221> NAME/KEY: MISC_FEATURE
<222> LOCATION: (1)..(114)
<223> OTHER INFORMATION: ColG s3b domain

<400> SEQUENCE: 32

Ile Lys Glu Val Glu Asn Asn Asp Phe Asp Lys Ala Met Lys Val
 1               5                  10                  15

Asp Ser Asn Ser Lys Ile Val Gly Thr Leu Ser Asn Asp Leu Lys
                 20                  25                  30

Asp Ile Tyr Ser Ile Asp Ile Gln Asn Pro Ser Asp Leu Asn Ile Val
             35                  40                  45

Val Glu Asn Leu Asp Asn Ile Lys Met Asn Trp Leu Leu Tyr Ser Ala
 50                  55                  60

Asp Asp Leu Ser Asn Tyr Val Asp Tyr Ala Asn Ala Asp Gly Asn Lys
 65                  70                  75                  80

Leu Ser Asn Thr Cys Lys Leu Asn Pro Gly Lys Tyr Tyr Leu Cys Val
                 85                  90                  95

Tyr Gln Phe Glu Asn Ser Gly Thr Gly Asn Tyr Ile Val Asn Leu Gln
                100                 105                 110

Asn Lys
```

<210> SEQ ID NO 33
<211> LENGTH: 115
<212> TYPE: PRT
<213> ORGANISM: Brevibacillus brevis
<220> FEATURE:
<221> NAME/KEY: MISC_FEATURE
<222> LOCATION: (1)..(115)
<223> OTHER INFORMATION: ColG s3b domain

<400> SEQUENCE: 33

Tyr Gln Glu Asn Glu Ser Asn Asp Ser Thr Glu Gln Ala Asn Gly Pro
1               5                   10                  15

Leu Lys Ile Gly Thr Thr Val Ser Gly Asp Met Lys Gly Asn Asp Trp
            20                  25                  30

Gln Asp Ile Phe Ala Phe Gln Val Asp Lys Pro Glu Glu Ile Arg Ile
        35                  40                  45

Ser Leu Asn Pro Gln Glu Gly Gln Gly Val Thr Trp Met Leu Phe His
    50                  55                  60

Glu Gly Asn Leu Asp Gln Pro Val Thr Tyr Pro Gln Glu Arg Glu Gly
65                  70                  75                  80

Asn Leu Gln Ser Ala His Tyr Gln Val Lys Pro Gly Arg Tyr Phe Leu
                85                  90                  95

Tyr Val Tyr Lys Tyr Gln Asn Glu Asp Ile Val Tyr Thr Val Glu Thr
            100                 105                 110

Lys Gln Arg
        115

<210> SEQ ID NO 34
<211> LENGTH: 114
<212> TYPE: PRT
<213> ORGANISM: Paenibacillus dendritiformis
<220> FEATURE:
<221> NAME/KEY: MISC_FEATURE
<222> LOCATION: (1)..(114)
<223> OTHER INFORMATION: ColG s3b domain

<400> SEQUENCE: 34

Phe Glu Glu Thr Glu Pro Asn Asp Thr Pro Glu Thr Ala Asn Gly Pro
1               5                   10                  15

Ile Pro Ala Gly Arg Pro Val Val Gly Thr Leu Asn Gly Ser Asp Lys
            20                  25                  30

Gln Asp Val Phe Ile Ile Asp Val Asp Gln Pro Ala Glu Leu Gln Ile
        35                  40                  45

Glu Leu Glu Arg Arg Leu Gly Ser Gly Val Asn Trp Ile Leu Tyr Arg
    50                  55                  60

Glu Gly Asp Thr Asp Arg Pro Leu Leu Tyr Pro Ser Glu Val Glu Gly
65                  70                  75                  80

Asn Arg Met Ser Gly Gly Phe Ala Ala Glu Ala Gly Arg Tyr His Leu
                85                  90                  95

Tyr Val Tyr Lys Tyr Thr Asp Glu Asp Ile His Tyr Thr Leu Gln Val
            100                 105                 110

Gln His

<210> SEQ ID NO 35
<211> LENGTH: 115
<212> TYPE: PRT
<213> ORGANISM: Clostridium sordellii
<220> FEATURE:
<221> NAME/KEY: MISC_FEATURE
<222> LOCATION: (1)..(115)

<223> OTHER INFORMATION: ColG s3b domain

<400> SEQUENCE: 35

Gly Val Glu Gln Glu Asp Asn Asn Ser Phe Glu Lys Ala Asn Pro Phe
1               5                   10                  15

Ser Ile Asn Gln Leu Val Lys Gly Glu Leu Asp Asn Asn Lys Asp Thr
            20                  25                  30

Ser Asp Tyr Phe Lys Phe Glu Val Lys Glu Asp Ala Gln Leu Asn Ile
        35                  40                  45

Ser Leu Glu Lys Thr Glu Gly Asp Gly Val Asn Trp Leu Leu Phe Lys
    50                  55                  60

Asp Ser Asp Leu Glu Asn Tyr Ile Ala Ser Pro Thr Glu Ser Ile Asp
65                  70                  75                  80

Asn Lys Leu Asn Gly Lys Val Asp Leu Lys Val Gly Thr Tyr Tyr Leu
                85                  90                  95

Glu Val Tyr Gly Tyr Gly Ser Ser Pro Val Lys Tyr Asn Phe Lys Val
            100                 105                 110

Thr Pro Asn
        115

<210> SEQ ID NO 36
<211> LENGTH: 111
<212> TYPE: PRT
<213> ORGANISM: Clostridium sporogenes
<220> FEATURE:
<221> NAME/KEY: MISC_FEATURE
<222> LOCATION: (1)..(111)
<223> OTHER INFORMATION: ColG s3c domain

<400> SEQUENCE: 36

Ile His Glu Lys Glu Asn Asn Asp Ser Phe Glu Ser Ala Asn Lys Ile
1               5                   10                  15

Val Leu Asn Ala Pro Ile Leu Gly Ser Leu Asn Gly Glu Asp Leu Arg
            20                  25                  30

Asp Ile Tyr Ser Phe Glu Ile Lys Glu Thr Lys Asp Leu Asn Ile Lys
        35                  40                  45

Leu Thr Asn Leu Asn Asn Leu Gly Leu Thr Trp Thr Leu Tyr Lys Glu
    50                  55                  60

Ser Asp Leu Asn Asn Tyr Ile Ala Tyr Gly Ser Lys Leu Gly Ser Thr
65                  70                  75                  80

Ile Val Gly Asn Cys His Val Thr Pro Gly Lys Tyr Tyr Leu Tyr Val
                85                  90                  95

Tyr Lys Tyr Ser Gly Asn Asn Gly Asn Tyr Ser Leu Ile Ile Lys
            100                 105                 110

<210> SEQ ID NO 37
<211> LENGTH: 111
<212> TYPE: PRT
<213> ORGANISM: Clostridium botulinum
<220> FEATURE:
<221> NAME/KEY: MISC_FEATURE
<222> LOCATION: (1)..(111)
<223> OTHER INFORMATION: ColG s3c domain from strain A3

<400> SEQUENCE: 37

Ile Tyr Glu Lys Glu Asn Asn Asp Ser Phe Glu Thr Ala Asn Lys Ile
1               5                   10                  15

Met Leu Asn Thr Thr Val Leu Gly Asn Leu Asn Gly Lys Asp Val Arg
            20                  25                  30

```
Asp Ile Tyr Ser Phe Asp Ile Lys Glu Ala Lys Asp Leu Asp Ile Lys
             35                  40                  45

Leu Asn Asn Leu Asn Asn Leu Gly Leu Ala Trp Asn Leu Tyr Lys Glu
 50                  55                  60

Ser Asp Leu Asn Asn Tyr Ile Ala Tyr Gly Ser Val Ser Gly Asn Thr
 65                  70                  75                  80

Ile Lys Gly Lys Cys Asn Val Ala Pro Gly Lys Tyr Tyr Leu Tyr Val
                 85                  90                  95

Tyr Lys Tyr Ser Gly Asp Asn Gly Asn Tyr Ser Leu Ala Ile Lys
            100                 105                 110
```

```
<210> SEQ ID NO 38
<211> LENGTH: 111
<212> TYPE: PRT
<213> ORGANISM: Bacillus cereus
<220> FEATURE:
<221> NAME/KEY: MISC_FEATURE
<222> LOCATION: (1)..(111)
<223> OTHER INFORMATION: AH603 domain

<400> SEQUENCE: 38

Leu Thr Glu Ser Glu Pro Asn Asn Arg Pro Glu Glu Ala Asn Arg Ile
 1               5                  10                  15

Gly Leu Asn Thr Thr Ile Lys Gly Ser Leu Ile Gly Gly Asp His Thr
             20                  25                  30

Asp Val Tyr Thr Phe Asn Val Ala Ser Ala Lys Asn Ile Asn Ile Ser
             35                  40                  45

Val Leu Asn Glu Tyr Gly Ile Gly Met Thr Trp Val Leu His His Glu
 50                  55                  60

Ser Asp Met Gln Asn Tyr Ala Ala Tyr Gly Gln Val Asn Gly Asn His
 65                  70                  75                  80

Ile Glu Ala Asn Phe Asn Ala Lys Pro Gly Lys Tyr Tyr Leu Tyr Val
                 85                  90                  95

Tyr Lys Tyr Asp Asn Gly Asp Gly Thr Tyr Glu Leu Ser Val Lys
            100                 105                 110
```

```
<210> SEQ ID NO 39
<211> LENGTH: 111
<212> TYPE: PRT
<213> ORGANISM: Bacillus anthracis
<220> FEATURE:
<221> NAME/KEY: MISC_FEATURE
<222> LOCATION: (1)..(111)
<223> OTHER INFORMATION: ColG domain

<400> SEQUENCE: 39

Leu Thr Glu Ser Glu Pro Asn Asn Arg Pro Glu Glu Ala Asn Arg Ile
 1               5                  10                  15

Gly Leu Asn Thr Thr Ile Lys Gly Ser Leu Ile Gly Gly Asp His Thr
             20                  25                  30

Asp Val Tyr Thr Phe Asn Val Ala Ser Ala Lys Asn Ile Asp Ile Ser
             35                  40                  45

Val Leu Asn Glu Tyr Gly Ile Gly Met Thr Trp Val Leu His His Glu
 50                  55                  60

Ser Asp Met Gln Asn Tyr Ala Ala Tyr Gly Gln Ala Asn Gly Asn His
 65                  70                  75                  80

Ile Glu Ala Asn Phe Asn Ala Lys Pro Gly Lys Tyr Tyr Leu Tyr Val
                 85                  90                  95

Tyr Lys Tyr Asp Asn Gly Asp Gly Thr Tyr Glu Leu Ser Val Lys
```

```
            100                 105                 110

<210> SEQ ID NO 40
<211> LENGTH: 111
<212> TYPE: PRT
<213> ORGANISM: Bacillus cereus
<220> FEATURE:
<221> NAME/KEY: MISC_FEATURE
<222> LOCATION: (1)..(111)
<223> OTHER INFORMATION: G9842 domain

<400> SEQUENCE: 40

Val Thr Glu Asn Glu Pro Asn Asn Glu Pro Arg Gln Ala Asn Lys Val
1               5                   10                  15

Asn Phe His Thr Pro Val Lys Gly Thr Leu His Asn Ser Asp Arg Val
            20                  25                  30

Asp Val Phe Thr Phe Gln Ile Asp Ser Pro Glu Asn Ile Asn Ile Ser
        35                  40                  45

Leu Leu Asn Glu Gln Asn Ile Gly Met Thr Trp Val Leu His His Glu
    50                  55                  60

Ser Asp Leu Asn Asn Tyr Val Ala Tyr Gly Glu Asn Glu Gly Asn Val
65                  70                  75                  80

Val Lys Gly Thr Tyr Asn Ala Lys Pro Gly Lys Tyr Tyr Leu Tyr Val
                85                  90                  95

Tyr Lys Tyr Glu Asn Lys Asp Gly Ser Tyr Val Leu Asn Ile Lys
            100                 105                 110

<210> SEQ ID NO 41
<211> LENGTH: 111
<212> TYPE: PRT
<213> ORGANISM: Bacillus mycoides
<220> FEATURE:
<221> NAME/KEY: MISC_FEATURE
<222> LOCATION: (1)..(111)
<223> OTHER INFORMATION: ColG domain

<400> SEQUENCE: 41

Ser Val Glu Lys Glu Pro Asn Asn Ser Phe Gln Thr Ala Asn Lys Leu
1               5                   10                  15

Gln Leu Asn Gln Leu Leu Arg Ala Ser Leu Gly Asn Gly Asp Thr Ser
            20                  25                  30

Asp Tyr Phe Glu Ile Asn Val Glu Thr Ala Arg Asn Leu Gln Ile Asn
        35                  40                  45

Val Thr Lys Glu Asn Asn Ile Gly Val Asn Trp Val Leu Tyr Ser Ala
    50                  55                  60

Ala Asp Leu Asn Asn Tyr Val Thr Tyr Ala Gln Thr Gln Gly Asn Lys
65                  70                  75                  80

Leu Val Gly Ser Tyr Asn Ala His Pro Gly Lys Tyr Tyr Leu His Val
                85                  90                  95

Tyr Gln Tyr Gly Gly Gly Thr Gly Asn Tyr Thr Val Glu Val Lys
            100                 105                 110

<210> SEQ ID NO 42
<211> LENGTH: 112
<212> TYPE: PRT
<213> ORGANISM: Bacillus weihensteph
<220> FEATURE:
<221> NAME/KEY: MISC_FEATURE
<222> LOCATION: (1)..(112)
<223> OTHER INFORMATION: ColG domain

<400> SEQUENCE: 42
```

```
Ala Val Glu Lys Glu Pro Asn Ser Phe Asp Ala Ala Asn Pro Leu
1               5                   10                  15

Ser Leu Asn Ala Leu Leu Arg Gly Asn Leu Ser Asp Gln Asp Gln Val
                20                  25                  30

Asp Arg Phe Val Ile Asp Val Lys Asp Pro Lys Asp Leu Gln Ile Thr
            35                  40                  45

Val Thr Asn Glu Gln Asn Leu Gly Leu Asn Trp Val Leu Tyr Ser Glu
    50                  55                  60

Ser Asp Leu Asn Asn Tyr Val Thr Tyr Ala Thr Lys Arg Asp Gly Asn
65                  70                  75                  80

Lys Leu Leu Gly Asn Tyr Asn Ala Lys Pro Gly Lys Tyr Tyr Leu Ser
                85                  90                  95

Val Tyr Lys Tyr Gly Gly Gly Thr Gly Asn Phe Thr Val Glu Val Lys
            100                 105                 110
```

<210> SEQ ID NO 43
<211> LENGTH: 125
<212> TYPE: PRT
<213> ORGANISM: Clostridium histolyticum
<220> FEATURE:
<221> NAME/KEY: MISC_FEATURE
<222> LOCATION: (1)..(125)
<223> OTHER INFORMATION: ColH s3 domain

<400> SEQUENCE: 43

```
Gly Ile Asn Ser Pro Val Tyr Pro Ile Gly Thr Glu Lys Glu Pro Asn
1               5                   10                  15

Asn Ser Lys Glu Thr Ala Ser Gly Pro Ile Val Pro Gly Ile Pro Val
                20                  25                  30

Ser Gly Thr Ile Glu Asn Thr Ser Asp Gln Asp Tyr Phe Tyr Phe Asp
            35                  40                  45

Val Ile Thr Pro Gly Glu Val Lys Ile Asp Ile Asn Lys Leu Gly Tyr
    50                  55                  60

Gly Gly Ala Thr Trp Val Val Tyr Asp Glu Asn Asn Asn Ala Val Ser
65                  70                  75                  80

Tyr Ala Thr Asp Asp Gly Gln Asn Leu Ser Gly Lys Phe Lys Ala Asp
                85                  90                  95

Lys Pro Gly Arg Tyr Tyr Ile His Leu Tyr Met Phe Asn Gly Ser Tyr
            100                 105                 110

Met Pro Tyr Arg Ile Asn Ile Glu Gly Ser Val Gly Arg
            115                 120                 125
```

<210> SEQ ID NO 44
<211> LENGTH: 111
<212> TYPE: PRT
<213> ORGANISM: Clostridium histolyticum
<220> FEATURE:
<221> NAME/KEY: MISC_FEATURE
<222> LOCATION: (1)..(111)
<223> OTHER INFORMATION: ColH s3 domain

<400> SEQUENCE: 44

```
Gly Thr Glu Lys Glu Pro Asn Asn Ser Lys Glu Thr Ala Ser Gly Pro
1               5                   10                  15

Ile Val Pro Gly Ile Pro Val Ser Gly Thr Ile Glu Asn Thr Ser Asp
                20                  25                  30

Gln Asp Tyr Phe Tyr Phe Asp Val Ile Thr Pro Gly Glu Val Lys Ile
            35                  40                  45
```

```
Asp Ile Asn Lys Leu Gly Tyr Gly Gly Ala Thr Trp Val Val Tyr Asp
         50                  55                  60

Glu Asn Asn Ala Val Ser Tyr Ala Thr Asp Asp Gly Gln Asn Leu
 65                  70                  75                  80

Ser Gly Lys Phe Lys Ala Asp Lys Pro Gly Arg Tyr Tyr Ile His Leu
                 85                  90                  95

Tyr Met Phe Asn Gly Ser Tyr Met Pro Tyr Arg Ile Asn Ile Glu
             100                 105                 110
```

<210> SEQ ID NO 45
<211> LENGTH: 121
<212> TYPE: PRT
<213> ORGANISM: Clostridium histolyticum
<220> FEATURE:
<221> NAME/KEY: MISC_FEATURE
<222> LOCATION: (1)..(121)
<223> OTHER INFORMATION: ColH domain

<400> SEQUENCE: 45

```
Pro Val Tyr Pro Ile Gly Thr Glu Lys Glu Pro Asn Asn Ser Lys Glu
  1               5                  10                  15

Thr Ala Ser Gly Pro Ile Val Pro Gly Ile Pro Val Ser Gly Thr Ile
                 20                  25                  30

Glu Asn Thr Ser Asp Gln Asp Tyr Phe Tyr Phe Asp Val Ile Thr Pro
             35                  40                  45

Gly Glu Val Lys Ile Asp Ile Asn Lys Leu Gly Tyr Gly Gly Ala Thr
 50                  55                  60

Trp Val Val Tyr Asp Glu Asn Asn Ala Val Ser Tyr Ala Thr Asp
 65                  70                  75                  80

Asp Gly Gln Asn Leu Ser Gly Lys Phe Lys Ala Asp Lys Pro Gly Arg
                 85                  90                  95

Tyr Tyr Ile His Leu Tyr Met Phe Asn Gly Ser Tyr Met Pro Tyr Arg
             100                 105                 110

Ile Asn Ile Glu Gly Ser Val Gly Arg
             115                 120
```

<210> SEQ ID NO 46
<211> LENGTH: 234
<212> TYPE: PRT
<213> ORGANISM: Clostridium histolyticum
<220> FEATURE:
<221> NAME/KEY: MISC_FEATURE
<222> LOCATION: (1)..(234)
<223> OTHER INFORMATION: ColG s3a + s3b domains

<400> SEQUENCE: 46

```
Thr Pro Ile Thr Lys Glu Met Glu Pro Asn Asp Asp Ile Lys Glu Ala
  1               5                  10                  15

Asn Gly Pro Ile Val Glu Gly Val Thr Val Lys Gly Asp Leu Asn Gly
                 20                  25                  30

Ser Asp Asp Ala Asp Thr Phe Tyr Phe Asp Val Lys Glu Asp Gly Asp
             35                  40                  45

Val Thr Ile Glu Leu Pro Tyr Ser Gly Ser Ser Asn Phe Thr Trp Leu
 50                  55                  60

Val Tyr Lys Glu Gly Asp Asp Gln Asn His Ile Ala Ser Gly Ile Asp
 65                  70                  75                  80

Lys Asn Asn Ser Lys Val Gly Thr Phe Lys Ser Thr Lys Gly Arg His
                 85                  90                  95

Tyr Val Phe Ile Tyr Lys His Asp Ser Ala Ser Asn Ile Ser Tyr Ser
```

```
                100             105             110
Leu Asn Ile Lys Gly Leu Gly Asn Glu Lys Leu Lys Glu Lys Glu Asn
            115                 120                 125

Asn Asp Ser Ser Asp Lys Ala Thr Val Ile Pro Asn Phe Asn Thr Thr
            130                 135                 140

Met Gln Gly Ser Leu Leu Gly Asp Asp Ser Arg Asp Tyr Tyr Ser Phe
145                 150                 155                 160

Glu Val Lys Glu Gly Glu Val Asn Ile Glu Leu Asp Lys Lys Asp
                165                 170                 175

Glu Phe Gly Val Thr Trp Thr Leu His Pro Glu Ser Asn Ile Asn Asp
                180                 185                 190

Arg Ile Thr Tyr Gly Gln Val Asp Gly Asn Lys Val Ser Asn Lys Val
                195                 200                 205

Lys Leu Arg Pro Gly Lys Tyr Tyr Leu Val Tyr Lys Tyr Ser Gly
            210                 215                 220

Ser Gly Asn Tyr Glu Leu Arg Val Asn Lys
225                 230

<210> SEQ ID NO 47
<211> LENGTH: 239
<212> TYPE: PRT
<213> ORGANISM: Clostridium sporogenes
<220> FEATURE:
<221> NAME/KEY: MISC_FEATURE
<222> LOCATION: (1)..(239)
<223> OTHER INFORMATION: ColG s3a + s3b domains

<400> SEQUENCE: 47

Leu Val Ile Ser Glu Lys Glu Asp Asn Asp Ser Phe Asp Lys Ala Asn
1               5                   10                  15

Arg Val Cys Lys Asn Gln Ser Val Leu Ala Thr Leu Thr Asn Asp
            20                  25                  30

Asn Arg Asp Thr Tyr Tyr Phe Asp Ala Leu Thr Ala Gly Thr Ile Asp
            35                  40                  45

Val Ile Met Glu Asn Thr Asp Asn Ser Asn Ile Phe Asn Trp Leu
50                  55                  60

Ala Tyr Ser Ser Asp Asn Thr Asn Tyr Ile Gly Tyr Ser Thr Lys
65              70                  75                  80

Lys Glu Gly Asn Lys Leu Leu Gly Ser Phe Lys Val Pro Lys Pro Gly
                85                  90                  95

Arg Tyr Tyr Ile Leu Ala Tyr Lys Asn Ser Ser Asn Lys Ile Asn Tyr
            100                 105                 110

Lys Leu Thr Ile Asn Gly Asp Ile Asp Lys Ala Pro Leu Lys Asn Glu
            115                 120                 125

Ile His Glu Lys Glu Asn Asn Asp Ser Phe Glu Ser Ala Asn Lys Ile
130                 135                 140

Val Pro Asp Ala Pro Val Leu Gly Ser Leu Asn Gly Glu Asp Leu Arg
145                 150                 155                 160

Asp Ile Tyr Ser Phe Asp Ile Lys Glu Thr Lys Asp Leu Asn Ile Lys
                165                 170                 175

Leu Thr Asn Leu Asn Asn Leu Gly Leu Thr Trp Thr Leu Tyr Lys Glu
            180                 185                 190

Ser Asp Leu Thr Asn Tyr Ile Ala Tyr Gly Ser Lys Leu Gly Asn Thr
            195                 200                 205

Ile Val Gly Asn Cys His Val Thr Pro Gly Lys Tyr Tyr Leu Tyr Val
            210                 215                 220
```

Tyr Lys Tyr Ser Gly Asn Ser Gly Asn Tyr Ser Leu Ile Ile Lys
225                 230                 235

<210> SEQ ID NO 48
<211> LENGTH: 244
<212> TYPE: PRT
<213> ORGANISM: Clostridium botulinum
<220> FEATURE:
<221> NAME/KEY: MISC_FEATURE
<222> LOCATION: (1)..(244)
<223> OTHER INFORMATION: ColG s3a + s3b domains from type B

<400> SEQUENCE: 48

Ile Asn Val Asp Glu Glu Glu Tyr Asn Asp Asp Phe Glu Cys Ala Asn
1               5                   10                  15

Asn Ile Phe Lys Asn Gln Ile Met Ser Gly Asn Leu Asp Ser Ser Asp
            20                  25                  30

Lys Cys Asp Thr Phe Ser Phe Asn Ala Leu Ser Ala Gly Thr Ile Asn
        35                  40                  45

Val Thr Leu Glu Asn Ser Asn Ser Asp Ser Ser Thr Val Asn Trp Leu
    50                  55                  60

Ala Tyr Ser Ser Glu Asp Thr Asp Asn Tyr Ile Gly Tyr Ala Ser Glu
65                  70                  75                  80

Asn Asp Gly Asn Lys Phe Ser Gly Lys Phe Lys Val Asn Lys Pro Gly
                85                  90                  95

Lys Tyr Tyr Ile Val Ala Tyr Glu Val Asn Gly Ala Asp Ser Lys Tyr
            100                 105                 110

Lys Leu Lys Val Asp Gly Asp Ile Glu Asn Thr Ser Glu Ser Lys Pro
        115                 120                 125

Glu Asp Lys Glu Glu Ile Lys Glu Glu Ile Asn Asp Asp Ser Phe Asp
130                 135                 140

Ser Ala Thr Lys Ile Lys Ala Asn Ser Thr Ile Thr Asp Thr Leu Asn
145                 150                 155                 160

Gly Glu Asp Asn Lys Asp Ile Cys Tyr Phe Asn Val Asn Asn Asn Ser
                165                 170                 175

Asp Leu Asn Ile Glu Leu Asn Ser Leu Thr Asn Leu Gly Val Ala Trp
            180                 185                 190

Gln Leu Phe Ser Glu Glu Asp Leu Asp Asn Tyr Ile Ala Tyr Gly Ser
        195                 200                 205

Gln Ser Gly Asp Ser Ile Val Gly Thr Ala Asn Val Gln Pro Gly Lys
210                 215                 220

Tyr Tyr Leu Leu Ile Tyr Lys Tyr Thr Gln Ala Asp Gly Ser Tyr Thr
225                 230                 235                 240

Phe Thr Ile Lys

<210> SEQ ID NO 49
<211> LENGTH: 239
<212> TYPE: PRT
<213> ORGANISM: Clostridium tetani
<220> FEATURE:
<221> NAME/KEY: MISC_FEATURE
<222> LOCATION: (1)..(239)
<223> OTHER INFORMATION: ColG s3a + s3b domains from strain E88

<400> SEQUENCE: 49

Asn Val Ile Tyr Glu Lys Glu Asn Asn Asp Ser Phe Asp Lys Ala Asn
1               5                   10                  15

Lys Ile His Lys Asn Gln Ile Val Met Ala Thr Leu Asp Thr Glu Asp

```
                  20                  25                  30
Tyr Arg Asp Thr Phe Tyr Phe Asp Ala Leu Thr Ser Gly Ser Ile Asp
            35                  40                  45

Ile Thr Ile Glu Asn Ile His Gly Asn Ser Asp Ala Phe Asn Trp Leu
 50                  55                  60

Val Tyr Asn Asp Glu Asp Leu Asn Asn Tyr Ile Ala Tyr Pro Thr Lys
 65                  70                  75                  80

Lys Glu Asp Asn Lys Leu Met Gly Ser Phe Lys Val His Lys Pro Gly
                85                  90                  95

Arg Tyr Tyr Ile Leu Val Tyr Lys Thr Ser Leu Asn Lys Val Asn Tyr
            100                 105                 110

Lys Leu Asn Ile Ser Asp Ala Thr Asn Met Ala Pro Val Ile Lys Lys
        115                 120                 125

Ile His Glu Lys Glu Asn Asn Asp Ser Phe Glu Thr Ala Asn Lys Ile
    130                 135                 140

Thr Leu Asp Thr Leu Val Leu Gly Asn Leu Asp Tyr Lys Asp Val Ser
145                 150                 155                 160

Asp Ile Tyr Ser Phe Asp Ile Glu Asn Thr Lys Asp Leu Asn Ile Lys
                165                 170                 175

Leu Thr Asn Leu Asn Asn Leu Gly Ile Ala Trp Asn Leu Tyr Lys Glu
            180                 185                 190

Ser Asp Leu Asn Asn Tyr Ile Ala Tyr Gly Ala Lys Ser Asp Asn Ala
        195                 200                 205

Ile Val Gly Lys Cys Asn Leu Ser Pro Gly Lys Tyr Tyr Leu Tyr Val
    210                 215                 220

Tyr Lys Tyr Ser Gly Asp Lys Gly Asn Tyr Ser Val Ile Ile Asn
225                 230                 235

<210> SEQ ID NO 50
<211> LENGTH: 243
<212> TYPE: PRT
<213> ORGANISM: Clostridium perfringens
<220> FEATURE:
<221> NAME/KEY: MISC_FEATURE
<222> LOCATION: (1)..(243)
<223> OTHER INFORMATION: ColG s3a + s3b domains

<400> SEQUENCE: 50

Glu Val Ile Asn Glu Ser Glu Pro Asn Asn Asp Phe Glu Lys Ala Asn
 1               5                  10                  15

Gln Ile Ala Lys Ser Asn Met Leu Val Lys Gly Thr Leu Ser Glu Glu
            20                  25                  30

Asp Tyr Ser Asp Lys Tyr Tyr Phe Asp Val Ala Lys Lys Gly Asn Val
        35                  40                  45

Lys Ile Thr Leu Asn Asn Leu Asn Ser Val Gly Ile Thr Trp Thr Leu
    50                  55                  60

Tyr Lys Glu Gly Asp Leu Asn Asn Tyr Val Leu Tyr Ala Thr Gly Asn
 65                  70                  75                  80

Asp Gly Thr Val Leu Lys Gly Glu Lys Thr Leu Glu Pro Gly Arg Tyr
                85                  90                  95

Tyr Leu Ser Val Tyr Thr Tyr Asp Asn Gln Ser Gly Tyr Thr Val
            100                 105                 110

Asn Val Lys Gly Asn Leu Lys Asn Glu Val Lys Glu Thr Ala Lys Asp
        115                 120                 125

Ala Ile Lys Glu Val Glu Asn Asn Asn Asp Phe Asp Lys Ala Met Lys
    130                 135                 140
```

```
Val Asp Ser Asn Ser Lys Ile Val Gly Thr Leu Ser Asn Asp Asp Leu
145                 150                 155                 160

Lys Asp Ile Tyr Ser Ile Asp Ile Gln Asn Pro Ser Asp Leu Asn Ile
            165                 170                 175

Val Val Glu Asn Leu Asp Asn Ile Lys Met Asn Trp Leu Leu Tyr Ser
        180                 185                 190

Ala Asp Asp Leu Ser Asn Tyr Val Asp Tyr Ala Asn Ala Asp Gly Asn
        195                 200                 205

Lys Leu Ser Asn Thr Cys Lys Leu Asn Pro Gly Lys Tyr Tyr Leu Cys
210                 215                 220

Val Tyr Gln Phe Glu Asn Ser Gly Thr Gly Asn Tyr Ile Val Asn Leu
225                 230                 235                 240

Gln Asn Lys
```

<210> SEQ ID NO 51
<211> LENGTH: 239
<212> TYPE: PRT
<213> ORGANISM: Brevibacillus brevis
<220> FEATURE:
<221> NAME/KEY: MISC_FEATURE
<222> LOCATION: (1)..(239)
<223> OTHER INFORMATION: ColG s3a + s3b domains

<400> SEQUENCE: 51

```
Asp Gly Ser Glu Thr Glu Gln Pro Asn Pro Asn Glu Glu Ser Ser
1               5                   10                  15

Leu Ser Leu Gly Lys Pro Ile Thr Gly Ile Ile His Pro Gln Lys Pro
            20                  25                  30

Ser Gln Glu Phe Arg Leu Asp Val Lys Ser Ala Gln Gln Leu Gln Val
        35                  40                  45

Glu Met Glu Thr Lys Gln Gly Asp Gly Val Ala Trp Leu Val Phe His
50                  55                  60

Glu Ala Asp Arg Glu Asn Tyr Ile Ser Tyr Pro Thr Lys Arg Glu Gly
65                  70                  75                  80

Asn Lys Leu Ile Gly Ser Phe Asp Ala Lys Pro Gly Thr Tyr Tyr Val
            85                  90                  95

Thr Ala Tyr Thr Tyr Arg Thr Glu Gln Glu Asp Gln Pro Phe Arg Leu
            100                 105                 110

Leu Val Thr Gly Glu Asp Arg Pro Gln Glu Leu Tyr Gln Glu Asn
            115                 120                 125

Glu Ser Asn Asp Ser Thr Glu Gln Ala Asn Gly Pro Leu Lys Ile Gly
    130                 135                 140

Thr Thr Val Ser Gly Asp Met Lys Gly Asn Asp Trp Gln Asp Ile Phe
145                 150                 155                 160

Ala Phe Gln Val Asp Lys Pro Glu Glu Ile Arg Ile Ser Leu Asn Pro
            165                 170                 175

Gln Glu Gly Gln Gly Val Thr Trp Met Leu Phe His Glu Gly Asn Leu
        180                 185                 190

Asp Gln Pro Val Thr Tyr Pro Gln Glu Arg Glu Gly Asn Leu Gln Ser
    195                 200                 205

Ala His Tyr Gln Val Lys Pro Gly Arg Tyr Phe Leu Tyr Val Tyr Lys
    210                 215                 220

Tyr Gln Asn Glu Asp Ile Val Tyr Thr Val Glu Thr Lys Gln Arg
225                 230                 235
```

-continued

<210> SEQ ID NO 52
<211> LENGTH: 242
<212> TYPE: PRT
<213> ORGANISM: Paenibacillus dendritiformis
<220> FEATURE:
<221> NAME/KEY: MISC_FEATURE
<222> LOCATION: (1)..(242)
<223> OTHER INFORMATION: ColG s3a + s3b domains

<400> SEQUENCE: 52

```
Pro Asn Ala Asp His Glu Pro Asn Asp Ser Trp Glu Gln Ala Val Pro
1               5                   10                  15

Leu Asp Gly Thr Gly Val Pro Val Ser Gly Lys Leu Ser Asp Thr Asp
            20                  25                  30

Arg Val Asp Val Tyr Arg Phe Asp Ala Gly Lys Ala Glu Gln Trp Thr
        35                  40                  45

Ile Glu Leu Glu Thr Glu Gln Ala Gln Ser Val Ala Trp Val Val His
    50                  55                  60

His Glu Ser Asp Leu Asn Asn Tyr Ala Ala Tyr Pro Thr Gln Val Glu
65                  70                  75                  80

Gly Thr Ser Val Ala Gly Ser Val Asp Ala Val Pro Gly Thr Tyr Tyr
                85                  90                  95

Val Tyr Val Tyr Ser Val Gly Asn Gly Glu Gln Ser Tyr Arg Leu Val
            100                 105                 110

Val Gln Pro Gly Thr Thr Gly Gln Glu Gln Glu Pro Glu Leu Pro Pro
        115                 120                 125

Phe Glu Glu Thr Glu Pro Asn Asp Thr Pro Glu Thr Ala Asn Gly Pro
    130                 135                 140

Ile Pro Ala Gly Arg Pro Val Val Gly Thr Leu Asn Gly Ser Asp Lys
145                 150                 155                 160

Gln Asp Val Phe Ile Ile Asp Val Asp Gln Pro Ala Glu Leu Gln Ile
                165                 170                 175

Glu Leu Glu Arg Arg Leu Gly Ser Gly Val Asn Trp Ile Leu Tyr Arg
            180                 185                 190

Glu Gly Asp Thr Asp Arg Pro Leu Leu Tyr Pro Ser Glu Val Glu Gly
        195                 200                 205

Asn Arg Met Ser Gly Gly Phe Ala Ala Glu Ala Gly Arg Tyr His Leu
    210                 215                 220

Tyr Val Tyr Lys Tyr Thr Asp Glu Asp Ile His Tyr Thr Leu Gln Val
225                 230                 235                 240

Gln His
```

<210> SEQ ID NO 53
<211> LENGTH: 238
<212> TYPE: PRT
<213> ORGANISM: Clostridium sordellii
<220> FEATURE:
<221> NAME/KEY: MISC_FEATURE
<222> LOCATION: (1)..(238)
<223> OTHER INFORMATION: ColG s3a + s3b domains

<400> SEQUENCE: 53

```
Pro Lys Gly Ser Gln Glu Val Gly Asn Asp Asp Thr Phe Glu Thr Ala
1               5                   10                  15

Asn Gly Pro Ile Lys Ile Asn Thr Asn Tyr Ser Gly Asp Leu Ser Asp
            20                  25                  30

Thr Asp Asn Lys Asp Tyr Tyr Tyr Phe Asn Leu Asp Asn Pro Ser Asn
        35                  40                  45
```

```
Ile Asn Ile Thr Leu Glu Asn Leu Asp Asn Lys Gly Ile Ser Trp Gln
 50                  55                  60

Leu Phe His Glu Ser Asp Leu Asn Asn Tyr Val Ala Tyr Pro Thr Thr
 65                  70                  75                  80

Ser Gly Ala Ile Leu Asn Gly Asp Tyr Asn Ala Thr Lys Pro Gly Lys
                 85                  90                  95

Tyr Tyr Ile Leu Val Tyr Asn His Asp Lys Ser Ile Ala Asn Tyr Asn
                100                 105                 110

Leu Lys Val Asn Phe Gly Asn Asn Asp Asp Gly Val Glu Gln Glu
                115                 120                 125

Asp Asn Asn Ser Phe Glu Lys Ala Asn Pro Phe Ser Ile Asn Gln Leu
130                 135                 140

Val Lys Gly Glu Leu Asp Asn Asn Lys Asp Thr Ser Asp Tyr Phe Lys
145                 150                 155                 160

Phe Glu Val Lys Glu Asp Ala Gln Leu Asn Ile Ser Leu Glu Lys Thr
                165                 170                 175

Glu Gly Asp Gly Val Asn Trp Leu Leu Phe Lys Asp Ser Asp Leu Glu
                180                 185                 190

Asn Tyr Ile Ala Ser Pro Thr Glu Ser Ile Asp Asn Lys Leu Asn Gly
                195                 200                 205

Lys Val Asp Leu Lys Val Gly Thr Tyr Tyr Leu Glu Val Tyr Gly Tyr
210                 215                 220

Gly Ser Ser Pro Val Lys Tyr Asn Phe Lys Val Thr Pro Asn
225                 230                 235
```

<210> SEQ ID NO 54
<211> LENGTH: 6
<212> TYPE: PRT
<213> ORGANISM: Clostridium histolyticum
<220> FEATURE:
<221> NAME/KEY: MISC_FEATURE
<222> LOCATION: (1)..(6)
<223> OTHER INFORMATION: ColG domain linker

<400> SEQUENCE: 54

```
Gly Leu Gly Asn Glu Lys
1               5
```

<210> SEQ ID NO 55
<211> LENGTH: 11
<212> TYPE: PRT
<213> ORGANISM: Clostridium sporogenes
<220> FEATURE:
<221> NAME/KEY: MISC_FEATURE
<222> LOCATION: (1)..(11)
<223> OTHER INFORMATION: ColG domain linker

<400> SEQUENCE: 55

```
Gly Asp Ile Asp Lys Ala Pro Leu Lys Asn Glu
1               5                   10
```

<210> SEQ ID NO 56
<211> LENGTH: 16
<212> TYPE: PRT
<213> ORGANISM: Clostridium botulinum
<220> FEATURE:
<221> NAME/KEY: MISC_FEATURE
<222> LOCATION: (1)..(16)
<223> OTHER INFORMATION: ColG domain linker from type B

<400> SEQUENCE: 56

```
Gly Asp Ile Glu Asn Thr Ser Glu Ser Lys Pro Glu Asp Lys Glu Glu
```

```
1               5                  10                 15
```

<210> SEQ ID NO 57
<211> LENGTH: 11
<212> TYPE: PRT
<213> ORGANISM: Clostridium tetani
<220> FEATURE:
<221> NAME/KEY: MISC_FEATURE
<222> LOCATION: (1)..(11)
<223> OTHER INFORMATION: ColG domain linker from strain E88

<400> SEQUENCE: 57

```
Asp Ala Thr Asn Met Ala Pro Val Ile Lys Lys
1               5                  10
```

<210> SEQ ID NO 58
<211> LENGTH: 14
<212> TYPE: PRT
<213> ORGANISM: Clostridium perfringens
<220> FEATURE:
<221> NAME/KEY: MISC_FEATURE
<222> LOCATION: (1)..(14)
<223> OTHER INFORMATION: ColG domain linker

<400> SEQUENCE: 58

```
Gly Asn Leu Lys Asn Glu Val Lys Glu Thr Ala Lys Asp Ala
1               5                  10
```

<210> SEQ ID NO 59
<211> LENGTH: 9
<212> TYPE: PRT
<213> ORGANISM: Brevibacillus brevis
<220> FEATURE:
<221> NAME/KEY: MISC_FEATURE
<222> LOCATION: (1)..(9)
<223> OTHER INFORMATION: ColG domain linker

<400> SEQUENCE: 59

```
Gly Glu Asp Arg Pro Gln Glu Gln Leu
1               5
```

<210> SEQ ID NO 60
<211> LENGTH: 14
<212> TYPE: PRT
<213> ORGANISM: Paenibacillus dendritiformis
<220> FEATURE:
<221> NAME/KEY: MISC_FEATURE
<222> LOCATION: (1)..(14)
<223> OTHER INFORMATION: ColG domain linker

<400> SEQUENCE: 60

```
Pro Gly Thr Thr Gly Gln Glu Gln Glu Pro Glu Leu Pro Pro
1               5                  10
```

<210> SEQ ID NO 61
<211> LENGTH: 7
<212> TYPE: PRT
<213> ORGANISM: Clostridium sordellii
<220> FEATURE:
<221> NAME/KEY: MISC_FEATURE
<222> LOCATION: (1)..(7)
<223> OTHER INFORMATION: ColG domain linker

<400> SEQUENCE: 61

```
Phe Gly Asn Asn Asn Asp Asp
1               5
```

<210> SEQ ID NO 62

```
<211> LENGTH: 95
<212> TYPE: PRT
<213> ORGANISM: Clostridium histolyticum
<220> FEATURE:
<221> NAME/KEY: MISC_FEATURE
<222> LOCATION: (1)..(95)
<223> OTHER INFORMATION: PKD domain (s2b) of ColH

<400> SEQUENCE: 62

Pro Glu Ile Lys Asp Leu Ser Glu Asn Lys Leu Pro Val Ile Tyr Met
1               5                   10                  15

His Val Pro Lys Ser Gly Ala Leu Asn Gln Lys Val Val Phe Tyr Gly
            20                  25                  30

Lys Gly Thr Tyr Asp Pro Asp Gly Ser Ile Ala Gly Tyr Gln Trp Asp
        35                  40                  45

Phe Gly Asp Gly Ser Asp Phe Ser Ser Glu Gln Asn Pro Ser His Val
    50                  55                  60

Tyr Thr Lys Lys Gly Glu Tyr Thr Val Thr Leu Arg Val Met Asp Ser
65                  70                  75                  80

Ser Gly Gln Met Ser Glu Lys Thr Met Lys Ile Lys Ile Thr Asp
                85                  90                  95

<210> SEQ ID NO 63
<211> LENGTH: 95
<212> TYPE: PRT
<213> ORGANISM: Clostridium histolyticum
<220> FEATURE:
<221> NAME/KEY: MISC_FEATURE
<222> LOCATION: (1)..(95)
<223> OTHER INFORMATION: PKD domain (s2b) of ColH

<400> SEQUENCE: 63

Glu Ile Lys Asp Leu Ser Glu Asn Lys Leu Pro Val Ile Tyr Met His
1               5                   10                  15

Val Pro Lys Ser Gly Ala Leu Asn Gln Lys Val Val Phe Tyr Gly Lys
            20                  25                  30

Gly Thr Tyr Asp Pro Asp Gly Ser Ile Ala Gly Tyr Gln Trp Asp Phe
        35                  40                  45

Gly Asp Gly Ser Asp Phe Ser Ser Glu Gln Asn Pro Ser His Val Tyr
    50                  55                  60

Thr Lys Lys Gly Glu Tyr Thr Val Thr Leu Arg Val Met Asp Ser Ser
65                  70                  75                  80

Gly Gln Met Ser Glu Lys Thr Met Lys Ile Lys Ile Thr Asp Pro
                85                  90                  95

<210> SEQ ID NO 64
<211> LENGTH: 215
<212> TYPE: PRT
<213> ORGANISM: Artificial Sequence
<220> FEATURE:
<223> OTHER INFORMATION: Synthetic - PKD-CBD fusion protein

<400> SEQUENCE: 64

Glu Ile Lys Asp Leu Ser Glu Asn Lys Leu Pro Val Ile Tyr Met His
1               5                   10                  15

Val Pro Lys Ser Gly Ala Leu Asn Gln Lys Val Val Phe Tyr Gly Lys
            20                  25                  30

Gly Thr Tyr Asp Pro Asp Gly Ser Ile Ala Gly Tyr Gln Trp Asp Phe
        35                  40                  45

Gly Asp Gly Ser Asp Phe Ser Ser Glu Gln Asn Pro Ser His Val Tyr
    50                  55                  60
```

```
Thr Lys Lys Gly Glu Tyr Thr Val Thr Leu Arg Val Met Asp Ser Ser
 65                  70                  75                  80

Gly Gln Met Ser Glu Lys Thr Met Lys Ile Lys Ile Thr Asp Pro Val
                 85                  90                  95

Tyr Pro Ile Gly Thr Glu Lys Glu Pro Asn Asn Ser Lys Glu Thr Ala
            100                 105                 110

Ser Gly Pro Ile Val Pro Gly Ile Pro Val Ser Gly Thr Ile Glu Asn
        115                 120                 125

Thr Ser Asp Gln Asp Tyr Phe Tyr Phe Asp Val Ile Thr Pro Gly Glu
    130                 135                 140

Val Lys Ile Asp Ile Asn Lys Leu Gly Tyr Gly Gly Ala Thr Trp Val
145                 150                 155                 160

Val Tyr Asp Glu Asn Asn Asn Ala Val Ser Tyr Ala Thr Asp Asp Gly
                165                 170                 175

Gln Asn Leu Ser Gly Lys Phe Lys Ala Asp Lys Pro Gly Arg Tyr Tyr
            180                 185                 190

Ile His Leu Tyr Met Phe Asn Gly Ser Tyr Met Pro Tyr Arg Ile Asn
        195                 200                 205

Ile Glu Gly Ser Val Gly Arg
    210                 215

<210> SEQ ID NO 65
<211> LENGTH: 8
<212> TYPE: PRT
<213> ORGANISM: Artificial Sequence
<220> FEATURE:
<223> OTHER INFORMATION: Synthetic - MMP cleavage sequence

<400> SEQUENCE: 65

Gly Pro Leu Gly Ile Ala Gly Pro
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 66

Gly Pro Gln Gly Ile Ala
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 67

Gly Pro Gln Gly Ile Leu
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 68
```

Gly Pro Gln Gly Leu Ala
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 69

Gly Pro Gln Gly Leu Leu
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 70

Gly Pro Leu Gly Ile Ala
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 71

Gly Pro Leu Gly Ile Leu
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 72

Gly Pro Leu Gly Leu Ala
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 73

Gly Pro Leu Gly Leu Leu
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 74

```
Gly Pro Arg Gly Leu Gln
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic - MMP cleavage sequence

<400> SEQUENCE: 75

Gly Pro Thr Gly Leu Ala
1               5

<210> SEQ ID NO 76
<211> LENGTH: 58
<212> TYPE: DNA
<213> ORGANISM: Artificial Sequence
<220> FEATURE:
<223> OTHER INFORMATION: Synthetic - single-stranded oligonucleotide
      encoding collagenase cleavage site

<400> SEQUENCE: 76
aattagcggc ggaggttcag gtcctctggg aatcgcaggt ccgtccggcg gaggtagc         58

<210> SEQ ID NO 77
<211> LENGTH: 54
<212> TYPE: DNA
<213> ORGANISM: Artificial Sequence
<220> FEATURE:
<223> OTHER INFORMATION: Synthetic - single-stranded oligonucleotide
      encoding collagenase cleavage site

<400> SEQUENCE: 77
gctacctccg ccggacggac ctgcgattcc cagaggacct gaacctccgc cgct             54
```